United States Patent [19]
Kilama

[11] Patent Number: 5,700,761
[45] Date of Patent: Dec. 23, 1997

[54] HERBICIDAL TRICYCLIC HETEROCYCLES

[75] Inventor: John Jolly Kilama, Wilmington, Del.

[73] Assignees: E. I. Du Pont de Nemours and Company, Wilmington, Del.; Degussa Aktiengesellschaft, Frankfurt, Germany

[21] Appl. No.: 693,107

[22] PCT Filed: Feb. 10, 1995

[86] PCT No.: PCT/US95/01502

§ 371 Date: Aug. 15, 1996

§ 102(e) Date: Aug. 15, 1996

[87] PCT Pub. No.: WO95/22547

PCT Pub. Date: Aug. 24, 1995

Related U.S. Application Data

[63] Continuation-in-part of Ser. No. 197,085, Feb. 16, 1994, abandoned.

[51] Int. Cl.⁶ .............. C07D 265/36; C07D 279/16; C07D 295/104; C07D 471/02
[52] U.S. Cl. .............. 504/221; 504/225; 504/245; 544/58.2; 544/173; 544/175; 546/81; 546/86
[58] Field of Search .............. 546/81, 86; 544/58.2, 544/173, 175; 504/221, 225, 245

[56] References Cited

U.S. PATENT DOCUMENTS 4,213,773  7/1980  Wolf ............................. 71/92
5,073,186  12/1991  Los ............................. 71/92

FOREIGN PATENT DOCUMENTS 0 493 323 A1  12/1991  European Pat. Off.
WO 93/15074  8/1993  WIPO
WO 94/14817  7/1994  WIPO

*Primary Examiner*—José G. Dees
*Assistant Examiner*—Jane C. Osweckі

[57] ABSTRACT

Compounds of Formula I having herbicidal utility are disclosed:

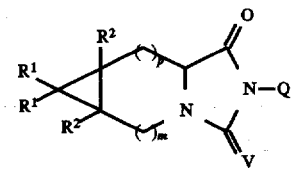

wherein Q, $R^1$, $R^2$, V, m and p are defined in the text, including compositions containing such compounds, and a method for controlling weeds employing such compounds.

7 Claims, No Drawings

HERBICIDAL TRICYCLIC HETEROCYCLES

This is a national filing of PCT/US Ser. No. 95/01502, filed 10 Feb., 1995, which is a continuation-in-part of U.S. Ser. No. 08/197,085, filed 16 Feb., 1994, now abandoned.

BACKGROUND OF THE INVENTION

This invention comprises tricyclic imides, pyrazoles, and triazolones, and bicyclic ureas wherein one of the rings is a fused cyclopropane, and their agriculturally-suitable salts, for weed control in crops.

EP-A-493,323 discloses bicyclic imide herbicides, WO 93/15074 discloses bicyclic pyrazole herbicides, and U.S. Pat. No. 4,213,773 discloses bicyclic triazolone herbicides, but they lack the fused cyclopropane ring present in the compounds of this invention.

SUMMARY OF THE INVENTION

The compounds of this invention are compounds of Formulae I–IV:

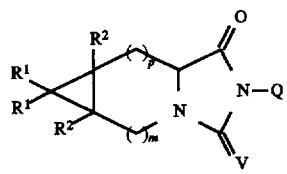  I

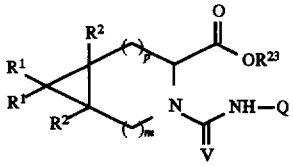  II

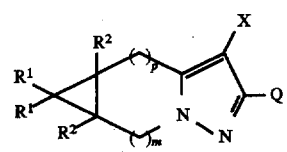  III

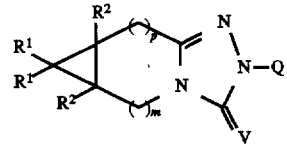  IV wherein

Q is

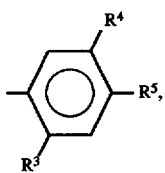  Q-1

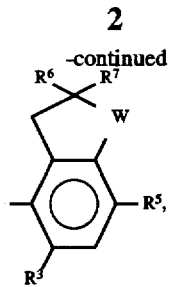  Q-2

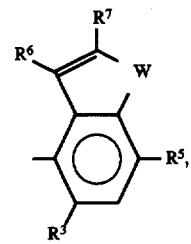  Q-3

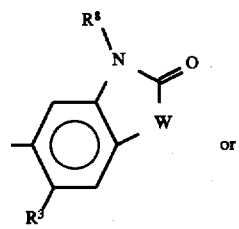  Q-4 or

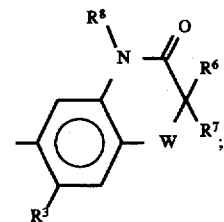  Q-5

$R^1$ is independently hydrogen; halogen or $C_1$–$C_3$ alkyl;
$R^2$ is independently hydrogen; fluorine; chlorine; or bromine;
V is O or S;
X is halogen or cyano;
m is 1 or 2;
p is 0 or 1 provided that when m is 2, then p is 0;
W is O or S;
$R^3$ is halogen;
$R^4$ is H; $C_1$–$C_8$ alkyl; $C_1$–$C_8$ haloalkyl; halogen; OH; $OR^9$; SH; $S(O)_nR^9$; $COR^9$; $CO_2R^9$; $C(O)SR^9$; $C(O)NR^{11}R^{12}$; CHO; $CR^{11}=NOR^{18}$; $CH=CR^{19}CO_2R^9$; $CH_2CHR^{19}CO_2R^9$; $CO_2N=CR^{13}R^{14}$; $NO_2$; CN; $NHSO_2R^{15}$; $NHSO_2NHR^{15}$; $NR^9R^{20}$; $NH_2$ or phenyl optionally substituted with $R^{21}$;
n is 0, 1 or 2;
$R^5$ is $C_1$–$C_2$ alkyl; $C_1$–$C_2$ haloalkyl; $OCH_3$; $SCH_3$; $OCHF_2$; halogen; CN or $NO_2$;
$R^6$ is H; $C_1$–$C_3$ alkyl or halogen;
$R^7$ is H; $C_1$–$C_3$ alkyl; halogen; $C_1$–$C_3$ haloalkyl; cyclopropyl; vinyl; $C_2$ alkynyl; CN; $C(O)R^{20}$; $CO_2R^{20}$; $C(O)NR^{20}R^{22}$; $CR^{16}R^{17}CN$; $CR^{16}R^{17}C(O)R^{20}$; $CR^{16}R^{17}CO_2R^{20}$; $CR^{16}R^{17}C(O)NR^{20}R^{22}$; $CHR^{16}OH$; $CHR^{16}OC(O)R^{20}$ or $OCHR^{16}OC(O)NR^{20}R^{22}$; or when Q is Q-2, $R^6$ and $R^7$ can be taken together with the carbon to which they are attached to form C=O;
$R^8$ is H; $C_1$–$C_6$ alkyl; $C_1$–$C_6$ haloalkyl; $C_2$–$C_6$ alkoxyalkyl; $C_3$–$C_6$ alkenyl; $C_3$–$C_6$ alkynyl; $C_4$–$C_7$ cycloalkyalkyl;

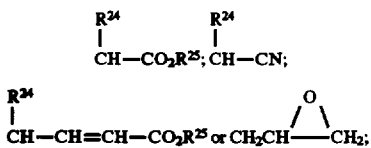

$R^9$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ alkoxyalkoxyalkyl; $C_4$–$C_8$ cycloalkylalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenyloxyalkyl; $C_4$–$C_8$ haloalkynyloxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with halogen, $C_1$–$C_3$ alkyl or $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkylcarbonyl; benzyl optionally substituted with halogen, $C_1$–$C_3$ alkyl or $C_1$–$C_3$ haloalkyl; $CHR^{16}COR^{10}$; $CHR^{16}P(O)(OR^{10})_2$; $CHR^{16}P(S)(OR^{10})_2$; $P(O)(OR^{10})_2$; $P(S)(OR^{10})_2$; $CHR^{16}C(O)NR^{11}R^{12}$; $CHR^{16}C(O)NH_2$; $CHR^{16}CO_2R^{10}$; $CO_2R^{10}$; $SO_2R^{10}$; phenyl optionally substituted with $R^{21}$;

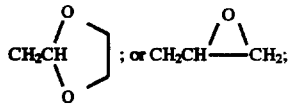

$R^{10}$ is $C_1$–$C_6$ alkyl; $C_1$–$C_6$ haloalkyl; $C_3$–$C_6$ alkenyl or $C_3$–$C_6$ alkynyl;

$R^{11}$ and $R^{13}$ are independently H or $C_1$–$C_4$ alkyl;

$R^{12}$ and $R^{14}$ are independently $C_1$–$C_4$ alkyl or phenyl optionally substituted with halogen, $C_1$–$C_3$ alkyl or $C_1$–$C_3$ haloalkyl; or $R^{11}$ and $R^{12}$ are taken together along with the nitrogen to which they are attached to form a piperidinyl, pyrrolidinyl or morpholinyl ring, each ring optionally substituted with $C_1$–$C_3$ alkyl, phenyl or benzyl; or $R^{13}$ and $R^{14}$ are taken together with the carbon to which they are attached to form $C_3$–$C_8$ cycloalkyl;

$R^{15}$ is $C_1$–$C_4$ alkyl or $C_1$–$C_4$ haloalkyl;

$R^{16}$ and $R^{17}$ are independently H or $C_1$–$C_5$ alkyl;

$R^{18}$ is H, $C_1$–$C_6$ alkyl, $C_3$–$C_6$ alkenyl or $C_3$–$C_6$ alkynyl;

$R^{19}$ and $R^{24}$ are independently H, $C_1$–$C_4$ alkyl or halogen; or $R^9$ and $R^{19}$ are taken together as $C_2$–$C_3$ alkylene;

$R^{20}$, $R^{21}$, and $R^{25}$ are independently H or $C_1$–$C_4$ alkyl;

$R^{22}$ is $C_1$–$C_2$ alkyl; $C_1$–$C_2$ haloalkyl; $OCH_3$; $SCH_3$; $OCHF_2$; halogen; CN or $NO_2$; and $R^{23}$ is H; $C_1$–$C_5$ alkyl; $C_1$–$C_5$ haloalkyl; $C_3$–$C_6$ cycloalkyl; $C_3$–$C_6$ halocycloalkyl; and phenyl optionally substituted with up to three substituents independently selected from the group halogen, $NO_2$, cyano, $C_1$–$C_2$ alkyl, $C_1$–$C_2$ haloalkyl, $C_1$–$C_2$ alkoxy, and $C_1$–$C_2$ haloalkoxy;

and their corresponding N-oxides and agriculturally suitable salts.

Preferred compounds of Formulae I–IV for reasons including ease of synthesis and/or greater herbicidal efficacy are:

1. A compound of Formulae I–IV wherein
    $R^1$ is hydrogen or halogen;
    $R^2$ is hydrogen; chlorine; or fluorine;
    $R^4$ is H; $C_1$–$C_8$ alkyl; $C_1$–$C_8$ haloalkyl; halogen; OH; $OR^9$; SH; $S(O)_nR^9$; $COR^9$; $CO_2R^9$; $C(O)SR^9$; $C(O)NR^{11}R^{12}$; CHO; $CH=CHCO_2R^9$; $CO_2N=CR^{13}R^{14}$; $NO_2$; CN; $NHSO_2R^{15}$; or $NHSO_2NHR^{15}$; and
    $R^{23}$ is $C_1$–$C_2$ alkyl.

2. Compounds of Preferred 1 wherein
    $R^2$ is hydrogen or fluorine; and
    $R^9$ is $C_1$–$C_4$ alkyl; $C_3$–$C_4$ alkenyl; $C_3$–$C_4$ alkynyl; $C_2$–$C_4$ alkoxyalkyl; $C_1$–$C_4$ haloalkyl; $C_3$–$C_4$ haloalkenyl or $C_3$–$C_4$ haloalkynyl.

3. Compounds of Preferred 2 wherein
    Q is Q-1 or Q-5;
    $R^1$ and $R^2$ are each hydrogen; and
    $R^5$ is halogen; CN; or $NO_2$.

Specifically preferred is a compound of Preferred 3 selected from the group:

(±)-2-[4-chloro-2-fluoro-5-(2-propynyloxy)phenyl] tetrahydrocyclopropa[3,4]-pyrrolo[1,2-c]imidazole-1,3(2H, 3aH)-dione and (±)-2-[4-chloro-2-fluoro-5-[(1-methyl-2-propynyl)oxy]phenyl]tetrahydrocyclopropa[3,4]-pyrrolo[1, 2-c]imidazole-1,3(2H,3aH)-dione.

Another embodiment of the invention is an agriculturally suitable composition for controlling the growth of undesired vegetation comprising an effective amount of a compound of Formulae I–IV with the substituents as defined above.

A further embodiment of the invention is a method for controlling the growth of undesired vegetation which comprises applying to the locus to be protected an effective amount of a compound of Formulae I–IV with the substituents as defined above.

DETAILS OF THE INVENTION

Compounds of Formulae I–IV may exist as one or more stereoisomers. The various stereoisomers include enantiomers, diastereomers and geometric isomers. One skilled in the art will appreciate that one stereoisomer may be the more active. One skilled in the art knows how to separate said enantiomers, diastereomers and geometric isomers. Accordingly, the present invention comprises racemic mixtures, individual stereoisomers, and optically active mixtures.

In the above recitations, the term "alkyl" used either alone or in compound words such as "alkylthio" includes straight or branched alkyl such as methyl, ethyl, n-propyl, isopropyl and the different butyl, pentyl and hexyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. Alkoxy includes methoxy, ethoxy, n-propyloxy, isopropyloxy and the different butoxy, pentoxy and hexyloxy isomers. Alkenyl includes straight or branched chain alkenes such as vinyl, 1-propenyl, 2-propenyl and the different butenyl, pentenyl and hexenyl isomers. "Alkenyloxy" includes straight-chain or branched alkenyloxy moieties, examples include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2C_2O$. "Alkynyloxy" includes straight-chain or branched alkynyloxy moieties, examples include $HC\equiv CCH_2O$, $CH_3C\equiv CCH_2O$ and $CH_3C\equiv CCH_2CH_2O$.

Cycloalkyl includes cyclopropyl, cyclobutyl, cyclopentyl and cyclohexyl.

The term "halogen", either alone or in a compound word such as "haloalkyl", denotes fluorine, chlorine, bromine or iodine. Further, when used in compound words such as "haloalkyl", said alkyl can be partially or fully substituted with independently selected halogen atoms. Examples of haloalkyl include $CH_2CH_2F$, $CF_2CF_3$ and $CH_2CHFCl$.

The total number of carbon atoms in a substituent group is indicated by the "$C_i$–$C_j$" prefix where i and j are numbers from 1 to 8. For example, $C_4$ alkoxy designates the various isomers of an alkoxy group containing a total of 4 carbon atoms, examples including $OCH_2CH_2CH_2CH_3$, $OCH_2CH(CH_3)_2$, $OC(CH_3)_3$.

The compounds represented by Formulae I–IV can be prepared according to the methods illustrated below in Schemes 1–13. The definitions of Q, X, m, p, W, n, and $R^1$ through $R^{25}$ in the compounds of Formulae 1–15 below are as defined above in the Summary of the Invention.

As illustrated in Scheme 1, treatment of the cis-cyclopropane dicarboxylic acid of Formula 1 with urea and heating to 175°–185° C. affords the cis-dicarboximide of Formula 2 as described by G. C. Crockett et al. in *Synth. Commun.* (1981), 11, 447–454.

Scheme 1

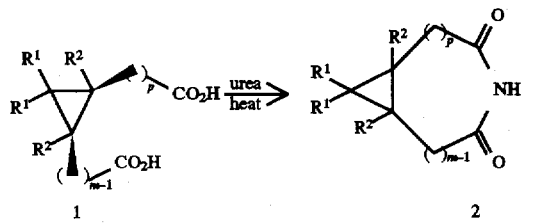

The diester of the diacid of Formula 1 is prepared by the method described by L. L. McCoy in *J. Am. Chem. Soc.*, (1958), 80, 65–68. A mixture of cis- and trans-diesters are obtained and the desired cis-isomer can be isolated by chromatography. The cis-diacid can be obtained by saponification of the diester using well-known methods.

Reduction of the cis-dicarboximide of Formula 2 with borane in an inert solvent, such as tetrahydrofuran (THF), followed by work-up with aqueous hydrochloric acid affords the azabicyclo[3.1.0]hexane hydrochloride of Formula 3 (Scheme 2). The reduction is preferably conducted with heating, for example in THF at reflux, as described by H. C. Brown and P. Heim in *J. Org. Chem.*, (1973), 38, 912–916.

Scheme 2

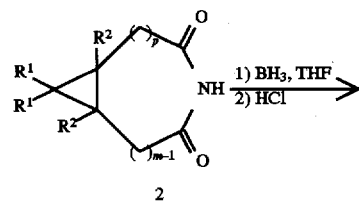

-continued
Scheme 2

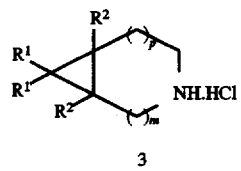

Alternatively, compounds of Formula 3 can be obtained by the cyclopropanation method (Scheme 3) described by B. Withop et al; in *J. Am. Chem. Soc.* (1971) 94, 3471–3477.

Scheme 3

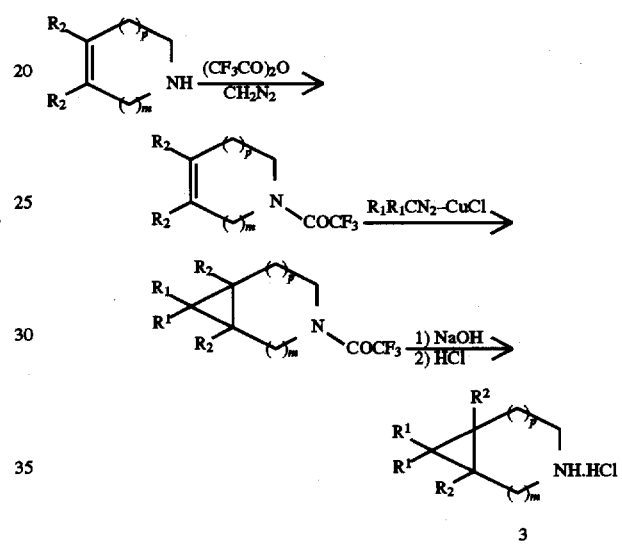

The amine hydrochloride of Formula 3 is converted via a five step sequence to the α-aminoacid of Formula 7 as illustrated in Scheme 4. Purification of the intermediates is not necessary.

Scheme 4

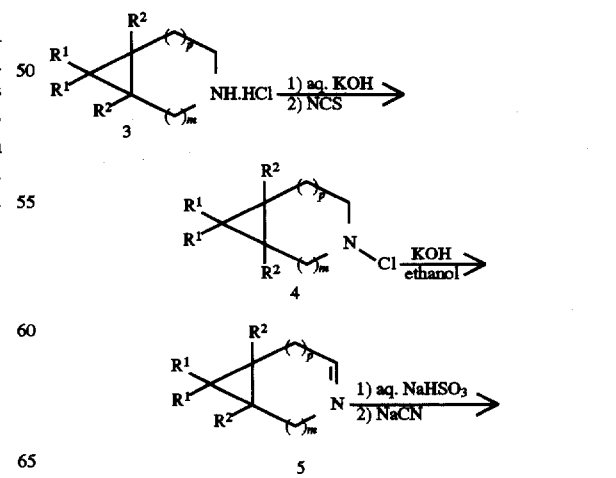

Scheme 4

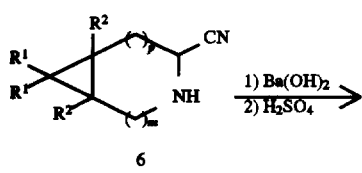

6

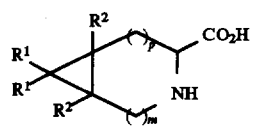

7

Scheme 5

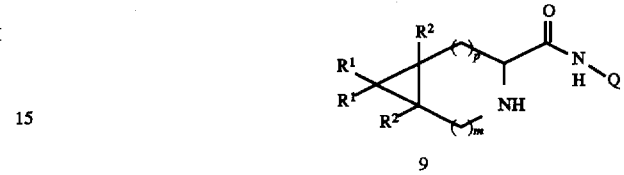

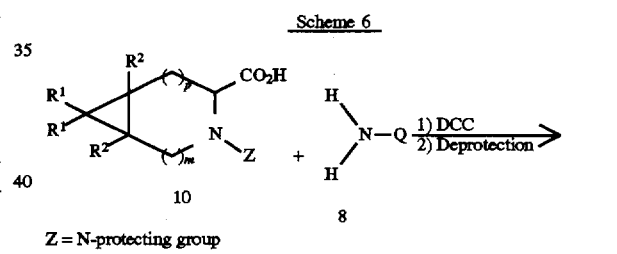

9

Neutralization of the amine hydrochloride with a base, such as concentrated aqueous potassium hydroxide, liberates the free amine. Dissolution of the amine in an inert solvent, such as diethyl ether, and treatment with a solution of N-chlorosuccinimide (NCS) in an inert solvent such as ether, produces the chloramine of Formula 4. The solution of the chloramine is then treated with ethanolic potassium hydroxide to effect dehydrochlorination and give the imine of Formula 5. Once again, the imine is not purified but treated directly first with aqueous sodium bisulfite, and then with solid sodium cyanide to afford the aminonitrile of Formula 6. The reaction mixture is poured into water and extracted with a water-immiscible solvent such as ether. The organic layers are dried and evaporated under reduced pressure to afford the aminonitrile. No additional purification is necessary. The aminonitrile of Formula 6 can be converted to the aminoacid of Formula 7 by hydrolysis with aqueous barium hydroxide followed by neutralization with sulfuric acid. A mixture of epimers at the carboxylic acid centers is obtained, and the individual diastereomers can be separated by chromatography.

Amides of Formula 9 can be prepared as outlined in Scheme 5. The acid of Formula 7 is reacted with an aniline of Formula 8 and a trialkylaluminum reagent (e.g., trimethylaluminum), in a non-coordinating solvent such as an aromatic hydrocarbon (e.g., benzene and toluene) or halogenated hydrocarbon (e.g., methylene chloride, chloroform, carbon tetrachloride, and dichlorobutane) to obtain the amide. Generally, the reaction requires 0.1 to 48 hours at a temperature of 0° C. to 25° C. to proceed to completion. The amides of Formula 9 are isolated by extraction into an organic solvent, aqueous wash, and removal of the solvent under reduced pressure. Purification can be accomplished by chromatography or recrystallization. Anilines of Formula 8 are known or can be prepared by known methods. For example, the synthesis of anilines of Formula 9 wherein Q is Q-1, Q-4, and Q-5 is described in U.S. Pat. No. 4,902,335. The anilines wherein Q is Q-2 and Q-3 can be prepared as described in U.S. Pat. No. 5,053,071 or by well known modifications thereof.

The reaction illustrated in Scheme 5 can also be performed starting with the ester of the acid of Formula 7.

In addition, amides of Formula 9 can be generated using conventional 1,3-dicyclohexylcarbodiimide (DCC) procedures for coupling N-protected compounds of Formula 10 with amines of Formula 8 followed by removal of the protecting group according to the procedures outlined by Bodanszky, M. in *Principles of Peptide Synthesis*, Volume 16, Springer-Verlag, New York, (1984) (Scheme 6).

Scheme 6

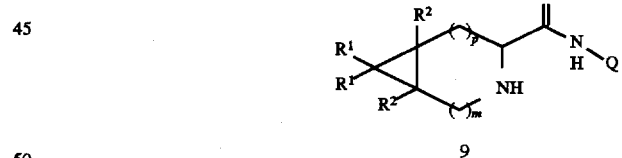

Z = N-protecting group

9

The tricyclic imide of Formula I can be prepared from the α-aminoamide of Formula 9 by condensation with thiophosgene, phosgene (U=Cl) or a phosgene equivalent as illustrated in Scheme 7. Treatment of the α-aminoamide with (thio)phosgene is preferably carried out in the presence of a tertiary-amine base such as triethylamine, pyridine, or N,N-diisopropylethylamine, in an inert solvent such as dichloromethane or 1-chlorobutane. The phosgene can be added as a gas or as a solution in an inert solvent such as toluene. Suitable temperatures range from about 0° C. to the reflux temperature of the solvent. Diphosgene (ClC(=O)OCCl$_3$) and triphosgene (Cl$_3$COC(=O)OCCl$_3$) can also be used in a similar manner.

Scheme 7

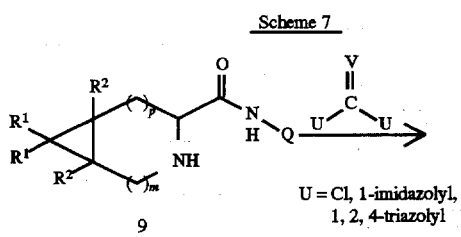

U = Cl, 1-imidazolyl, 1,2,4-triazolyl

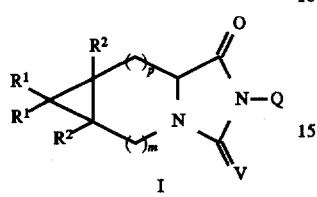

Alternatively, the imides of Formula I where V=O can be prepared using 1,1'-carbonyldiimidazole (U=1-imidazolyl, CDI). The amide of Formula 9 is dissolved in an inert solvent in which the CDI has sufficient solubility at the reaction temperature. Methylene chloride, 1-chlorobutane and toluene are three of many suitable inert solvents. The CDI is added as a solid or as a solution in an inert solvent at temperatures from 0° C. to 100° C. When the reaction is complete, the resulting mixture is poured into a water-immiscible solvent and washed successively with dilute mineral acid, water, and brine. The organic liquid phase is separated, dried, and evaporated to isolate the product.

Compounds of Formula I can also be prepared by treating amides of Formula 9 with 1,1'-carbonylditriazole (U=1,2,4-triazolyl, CDT) as described above for CDI. Additional base can be added to accelerate the reaction. Suitable bases include a trialkylamine, imidazole, pyridine, picoline or other substituted pyridine, or mixtures thereof. For both CDI and CDT, the carbonylating agent can be added as a pure compound, or as a solution of the pure compound in an inert solvent. For example, CDI can be first prepared by treatment of a solution of imidazole in an inert solvent with phosgene as described by Staab and Wendel (*Org. Syntheses*, Coll. Vol. 5, 201, (1973)), and then treated in situ with the amide of Formula 9 to afford I.

Compounds of Formula I can also be prepared from compounds of Formula II when $R^{23}$=H as shown in Scheme 8.

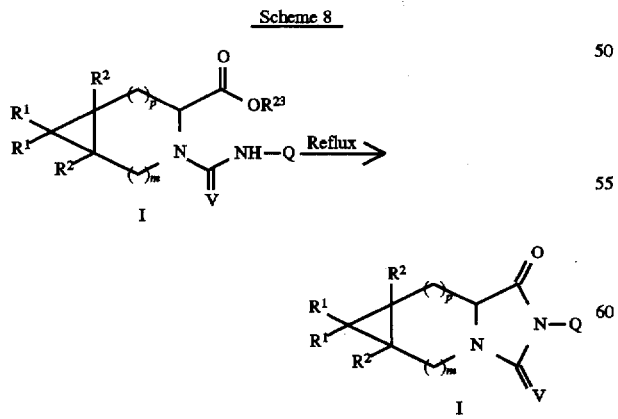

Intramolecular cyclization of II to give compounds in Formula I can be effected by heating II at elevated temperature between 5° C. to 200° C. in suitable inert organic solvents, e.g., an aromatic hydrocarbon such as benzene or toluene.

Compounds of Formula II can be prepared by first converting amines of Formula 8 to isocyanates or thiocyanates of Formula 10 using conventional diphosgene, triphosgene, or thiophosgene reaction with amines (Scheme 9). Generally, the triphosgene or the thiophosgene is contacted with amines as compound 8 at low temperature 0°–25° C. in the presence of a suitable base such as a tertiary amine, e.g., pyridine or triethylamine (with hydrocarbon solvents, e.g., toluene, chlorinated alkane such as chloroform or methylene chloride).

Scheme 9

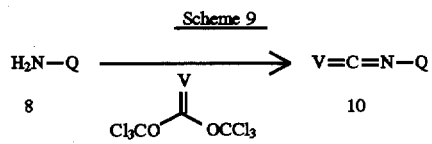

Compounds of Formula II can be obtained by contacting compounds of Formula 10 with compounds of Formula 3 (Scheme 10)

Scheme 10

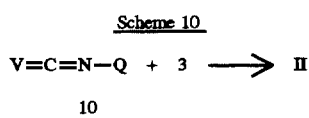

The reaction is run in a suitable organic solvent, e.g., chlorinated alkane such as chloroform or methylene chloride, an aromatic hydrocarbon such as benzene or toluene, or an ether type solvent such as THF. For completion of the reaction, it is sometimes necessary to heat the reaction mixture to reflux.

The tricyclic imides of Formula I and bicyclic ureas of Formula II can be isolated by extraction into an organic solvent, aqueous wash, and removal of the solvent under reduced pressure. Additional purification can be accomplished by chromatography or recrystallization.

Compounds of Formula III can be made by the reaction of sydnones of Formula 11 with appropriately substituted alkynes 12 (Scheme 11).

Scheme 11

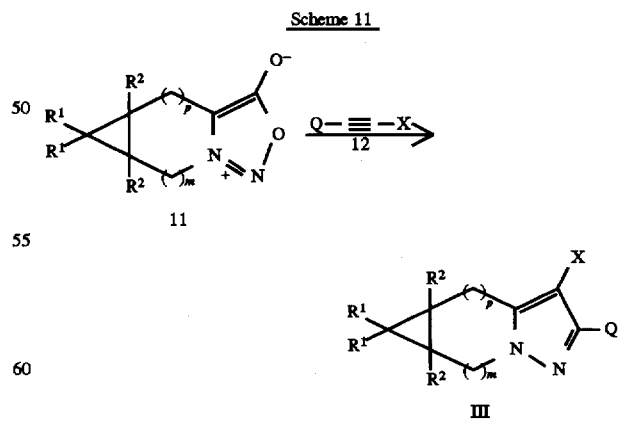

The reaction takes place at elevated temperatures generally between 80° C. and 200° C. The reaction may be performed in a variety of solvents with aromatic hydrocarbons such as xylenes preferred.

The sydnones of Formula 11 can be made using procedures known in the art (see S. D. Larsen and E. Martinsorough, *Tetrahedron Lett.* 1989, 4625 and D. Ranganathan and S. Bamezai, *Tetrahedron Lett.* 1983, 1067).

Scheme 12 shows how compounds of Formula III can also be prepared by coupling compounds of Formula 13, with aryl halides or sulfonates 14 in the presence of palladium catalysts as described by Yamanoka et al., *Heterocycles*, 33, 813–818 (1992). Compounds of Formula 13, can be made by sydnone cycloaddition as described in Scheme 11 using stannylated acetylenes.

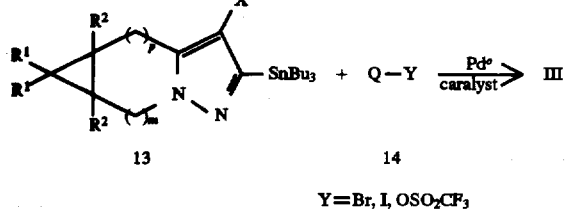

Scheme 12

Y=Br, I, OSO₂CF₃

The compounds in Formula IV may be made as shown in Scheme 13.

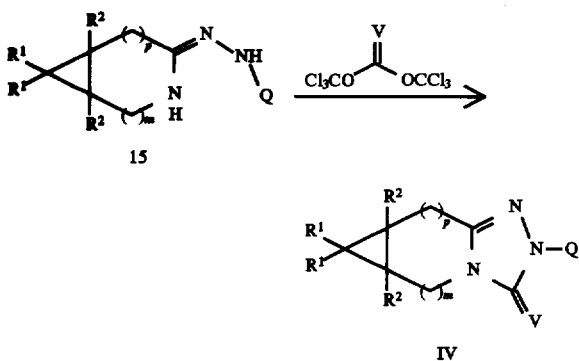

Scheme 13

The conversion of the amidrazones 15, or their acid salts (e.g., hydrochlorides), to the compounds of Formula IV is accomplished by reaction with either diphosgene, triphosgene or thiophosgene. The reaction is run in a suitable inert organic solvent, e.g., benzene, toluene, $CHCl_3$ or $CH_2Cl_2$ with a suitable base such as pyridine or a tertiary amine, e.g., $Et_3N$. The product of the reaction can be isolated by extraction into organic solvent, aqueous wash, and removal of the solvent under reduced pressure. Purification of the crude material is accomplished by standard techniques, e.g., crystallization, chromatography or distillation.

The amidrazones 15, may be prepared by methods similar to those described in U.S. Pat. No. 4,213,773.

It is recognized that some reagents and reaction conditions described above for preparing compounds of Formulae I–IV may not be compatible with certain functionalities present in the intermediates. In these instances, the incorporation of protection/deprotection sequences into the synthesis will aid in obtaining the desired products. The use and choice of the protecting group will be apparent to one skilled in chemical synthesis.

In the following Examples, all ¹H NMR spectra were measured in $CDCl_3$ solution at 300 MHz unless otherwise indicated.

EXAMPLE 1

Preparation of (±)-2-[4-chloro-2-fluoro-5-(2-propynyloxy)phenyl]tetrahydrocyclopropa[3,4]pyrrolo[1,2-c]imidazole-1,3(2H,3aH)-dione Step A Preparation of diethyl cis-1,2-cyclopropanedicarboxylate To a stirred suspension of 32.8 g (818.8 mmol) of 60% sodium hydride mineral oil dispersion in 200 mL of toluene under nitrogen, was added between 10 to 20 mL of a blend of ethyl acrylate (81.2 g, 810.7 mmol) and ethyl chloroacetate (99.4 g, 810.7 mmol) followed by several drops of ethanol. After an induction period of about 1 h, steady gas and heat evolution began with the reaction mixture temperature reaching 35° C. The remaining mixed ester reagent was carefully added dropwise with ice-bath cooling so as to maintain a reaction temperature of 30°–80° C. After the addition was complete (4 h), the mixture was cooled to room temperature and carefully poured into water (300 mL). The organic layer was separated and dried ($MgSO_4$) and evaporated to a dry residue. The dry residue was chromatographed on silica gel using 10% ethyl acetate in hexane as the eluant. The fractions containing the desired compound were combined and evaporated to dryness under reduced pressure to give 53.0 g of the title compound of Step A as a clear oil (35% yield). IR (neat, cm⁻¹): 1728.9 (C=O);

¹H NMR: δ4.20–4.12 (m,4H), 2.14–2.05 (t,2H), 1.71–1.62 (q,1H), 1.31–1.20 (m,7H).

Step B

Preparation of cis-1,2-cyclopropanedicarboxylic acid

A stirred mixture of diethyl cis-1,2-cyclopropanedicarboxylate (53.0 g, 284.6 mmol) and sodium hydroxide (32.4 g, 809.1 mmol) in water (200 mL) was heated at reflux for 5 h. The mixture was then allowed to stir at room temperature overnight. The ethanol formed was evaporated under reduced pressure and the remaining aqueous solution was acidified with a slight excess of concentrated aqueous HCl (74.8 mL, 92.8 mmol). The mixture was evaporated to dryness under reduced pressure, and the residue was washed with hot ethyl acetate (3 times with 200 mL). The ethyl acetate layer was separated, dried ($MgSO_4$) and evaporated to dryness under reduced pressure to give 35.5 g of the title compound of Step B as a white solid (96% yield); m.p. 122°–124° C. IR (mineral oil, cm⁻¹), 1691.0 (C=O); 2600–3100, broad (OH).

Step C preparation of cis-1,2-cyclopropanedicarboximide

A well-blended mixture of cis-1,2-cyclopropanedicarboxylic acid (5.0 g, 38.4 mmol) and urea (2.54 g, 42.24 mmol) in a round-bottom flask fitted with a condenser and magnetic stir bar, was immersed in a preheated oil bath (180° C.) and heated at 180° C. for 35 min with stirring. Gas evolution was observed during heating. The reaction mixture was then allowed to cool to room temperature. The mixture was then chromatographed on silica gel using 5% methanol in methylene chloride to obtain 2.4 g of the title compound of Step C as a white solid (56% yield); m.p. 93°–94° C.;

IR (mineral oil, cm⁻¹) 1678.9, 1758.3 (C=O).

Step D

Preparation of 3-azabicyclo[3.1.0]hexene hydrochloride salt

To a stirred solution of borane-tetrahydrofuran complex (1.0M, 35 mL, 135.0 mmol) under nitrogen and cooled to 0° C., was added cis-1,2-cyclopropanedicarboximide (5.0 g, 45.05 mmol) portionwise via solid addition funnel. The mixture was heated at reflux for 6 h. The reaction mixture was allowed to cool to 0° C., and then 6N aqueous HCl was added dropwise until the pH was approximately 3. The resultant mixture was stirred for an additional 1 h. The mixture was then made basic to pH 9 with 50% aqueous NaOH. Ethyl acetate (300 mL) and water (100 mL) were then added. The organic layer was separated and added to ethanol (100 mL). The solution was acidified to pH 6 with concentrated aqueous HCl and then evaporated to dryness under reduced pressure. The residue was triturated with cold 2-propanol. Evaporation of the 2-propanol under reduced pressure yielded 3.59 g of the title compound of Step D as a white solid (67% yield); m.p. 125°–127° C.

Step E

Preparation of (±)-3-azabicyclo[3.1.0]hexane-2-carboxylic acid

The compound, 3-azabicyclo[3.1.0]hexene hydrochloride salt (15.0 g, 125.43 mmol), was added to a saturated aqueous solution of potassium hydroxide (40 mL). The mixture was stirred at room temperature for 10 min and then washed with diethyl ether (3 times with 100 mL). The ether layer was dried ($MgSO_4$) and then added dropwise to a solution of N-chlorosuccinimide (29.7 g, 221.9 mmol) in diethyl ether (200 mL). The resultant mixture was stirred at ambient temperature for 3 h. Then, the mixture was filtered and the filtrate was washed with $H_2O$ (2 times with 50 mL), brine (50 mL) and dried ($MgSO_4$). The dried filtrate was added dropwise over a 30 min period to a solution of potassium hydroxide (8.28 g, 125.43 mmol) in absolute ethanol (300 mL). The resultant mixture was stirred at room temperature overnight. Filtration removed the inorganic salts, which were washed with ether. The combined filtrate and ether washings, which contained the imine, were treated with 13.05 g (125.4 mmol) of sodium bisulfite in 100 mL of water. After stirring vigorously for 15 min at room temperature, the two-phase mixture was treated with 6.48 g (125.43 mmol) of solid sodium cyanide. After stirring 2 h more at room temperature, the upper organic layer was decanted away and the aqueous layer was extracted with diethyl ether (2 times with 300 mL). The combined organic layer and ether extracts were dried ($MgSO_4$) and evaporated to dryness under reduced pressure to afford 12.1 g of 3-azabicyclo[3.1.0]hexane-2-carbonitrile. IR (neat, $cm^{-1}$): 2245.9 (CN). This crude product was used in the next reaction without further purification. A stirred solution of 12.1 g (112.0 mmol) of the crude carbonitrile and barium hydroxide hydrate (35.9 g, 114 mmol) in water (300 mL) was heated at reflux for 7 h. The reaction mixture was cooled to room temperature and acidified to pH 6 with concentrated sulfuric acid. The resulting white suspension was filtered through a CELITE (siliceous earth) bed, and the filtrate was allowed to settle for 30 min. The clear solution was decanted and evaporated under reduced pressure to dryness to give 9.8 g of the title compound of Step E as a white solid (69% yield). m.p. 211°–213° C.; IR (mineral oil, $cm^{-1}$): 1629.5 (C=O), 2600–3200 broad (OH).

Step F

Preparation of N-[4-chloro-2-fluoro-5-(2-propynyloxy) phenyl]-3-azabicyclo-[3.1.0]hexane-2-carboxamide To a mixture of 2.36 g (11.79 mmol) of 4-chloro-2-fluoro-5-(2-propynyl)oxyaniline and 1.5 g (11.79 mmol) of (±)-3-azabicyclo[3.1.0]hexane-2-carboxylic acid in methylene chloride (150 mL) stirred under nitrogen and cooled to 5° C. was added trimethylaluminum dropwise (2.0M, 11.8 mL, 23.58 mmol). The resultant mixture was stirred at room temperature for 48 h. Water (100 mL) was added dropwise at ice-bath temperature. The solid inorganic material which formed was filtered, and the filtrate was dried ($MgSO_4$) and evaporated under reduced pressure to dryness. Flash chromatography on silica gel yielded 1.3 g of the product of Step F as a tan solid; m.p. 113°–115° C. IR (mineral oil, $cm^{-1}$): 1687.1 (C=O); 2123.5 (C≡C).

Step G

Preparation of (±)-2-[4-chloro-2-fluoro-5-(2-propynyloxy) phenyl]tetrahydrocyclopropa[3.4]pyrrolo[1,2-c]imidazole-1,3(2H,3aH)-dione Triphosgene (256 mg, 0.86 mmol) in 10 mL of dioxane was added dropwise at 0° C. to a stirred mixture of 80 mg, (2.59 mmol) of the product of Step F and triethylamine (1.8 mL, 12.95 mmol). The mixture was stirred at room temperature for 30 min. Evaporation of the mixture under reduced pressure gave a dry residue. Flash chromatography of the residue on silica gel gave 0.4 g of the title compound of Step G, a compound of the invention; m.p. 52°–54° C.; IR (mineral oil, $cm^{-1}$): 1784, 1722 (C=O); 2120 (C≡C); $^1H$ NMR: δ 0.60–0.64 (m,1H), 1.20–1.31 (m,1H), 2.00–2.09 (m,1H), 2.10–2.20 (m,1H), 2.60 (s,1H), 3.11–3.19 (dd,1H), 4.18–4.23 (m,2H), 4.76–4.77 (d,2H), 7.02–7.06 (d,1H), 7.29–7.32 (d,1H).

EXAMPLE 2

Preparation of Ethyl 3-[2-chloro-4-fluoro-5-(hexahydro-1,3-dioxocyclopropa[3,4]pyrrolo[1,2-c] imidazol-2(3H)-yl)phenyl]-2-propenoate Step A Preparation of 2-chloro-4-fluoro-5-nitrobenzoic acid A blend of 70% nitric acid (64.5 gm) and concentrated sulfuric acid (65 mL) was added dropwise over an hour period to a suspension of 2-chloro-4-fluoro-benzoic acid (125.0 gm, 716 mL). The white suspension was stirred mechanically for 30 minutes at ambient temperature. The thick white suspension was carefully poured into ice-water (100 mL). Ethyl acetate (800 mL) was added. The organic layer was separated, dried ($MgSO_4$) and evaporated to dryness under vacuum to give the title compound of Step A as a white solid (156.0 gm, 99%); m.p. 134°–136° C.; IR ($cm^{-1}$), C=O (1719.8). This intermediate was used without further purification.

Step B

Preparation of 2-chloro-4-fluoro-5-nitrobenzenemethanol

To a stirred solution of compound in Step A, Example 2 (120.0 gm, 546.45 mmol, in THF (400 mL), under $N_2$, at room temperature was slowly added Borane—THF complex 1.0M (726.8 mL, 726.8 mmol, Aldrich) over a 2-hour period (ice-bath used to keep temperature at 20°–25° C.). The resultant solution was stirred at room temperature for 3 hours followed by the solution being heated to reflux for 1 hour. $H_2O$ (30 mL) was added very slowly dropwise at 5° C. (ice-bath). The solution turned dark and $H_2O$ (1 L) and ethyl acetate (1 L) were added. The light yellow organic layer was separated, dried ($MgSO_4$) and evaporated to dryness under vacuum. The residue was chromatographed on silica gel using 20% ethyl acetate in hexane. The desired fractions were combined and evaporated under vacuum to obtain the title compound of Step B as a soft-yellow solid (91.3 gm, 81%); m.p. 39°–41° C., IR (nujol, $cm^{-1}$): 3321.2 (OH);

$^1H$ NMR δ: 2.18–2.22 (t,1H), 4.81–4.83 (d,2H), 7.34–7.36 (d,1H), 8.30–8.33 (d,1H).

Step C

Preparation of 2-chloro-4-fluoro-5-nitrobenzaldehyde

To a suspension of pyridinium chlorochromate (PCC) (48.46 gm, 224.0 mmol, Aldrich) under $N_2$, at room temperature, was rapidly added a solution of the compound of Step B, Example 2, (30.82 gm, 1.49.9 mmol) in methylene chloride (100 mL). The mixture turned dark and slowly became homogeneous. The dark mixture was stirred at room temperature for 3.5 hours.

The mixture was added to diethyl ether (800 mL) and filtered through FLORISIL (activated magnesium silicate). The remaining black residue was washed with $Et_2O$ (2×200 mL) and filtered through FLORISIL (activated magnesium silicate). The diethyl ether portions were combined, dried over magnesium sulfate and evaporated to dryness. The dry residue was chromatographed on silica gel using 10% ethyl acetate in hexane. Fractions of desired product were combined and evaporated under vacuum to give the title compound of Step C (20.2 gm, 66%) as a yellow oil. IR (neat, $cm^{-1}$): 1703.3 (C=O); $^1H$ NMR δ: 7.47–7.51 (d,1H), 8.65–8.68 (d,1H), 10.41 (s,1H).

Step D
Preparation of Ethyl 3-(2-chloro-4-fluoro-5-nitrophenyl)-2-propenoate

A stirred mixture of the compound of Step C, Example 2, (11.5 gm, 56.51 mmol), (carbethoxymethyl)triphenylphosphonium bromide (24.2 gm, 56.51 mmol) and triethylamine (50 mL) in benzene (200 mL), under $N_2$, was heated to reflux for 1 hour. Water (200 mL) and ethyl acetate (200 mL) were added. The organic layer was separated, dried over magnesium sulfate and evaporated under reduce pressure to dryness. The residue was chromatographed on silica gel using hexane:EtOAc (15:5) mixture as eluent. The fractions were combined and evaporated under reduce pressure to obtain the title compound of Step D (9.3 gm, 60%) as a yellow solid; m.p. 86°–88° C., IR (nujol, $cm^{-1}$): 1716.8 (C=O); $^1H$ NMR δ: 1.33–1.38 (t,3H), 4.29–4.31 (q,2H), 6.44–6.54 (d,1H), 7.40–7.44 (d,1H), 7.93–7.99 (d,1H), 8.34–8.38 (d,1H).

Step E
Preparation of Ethyl 3-(5-amino-2-chloro-4-fluoro-2-propenoate

A stirred solution of the compound of Step D, Example 2, (3.5 gm, 12.8 mmol) in acetic acid (30 mL) was heated to reflux under $N_2$. The heat source was removed and iron powder (2.2 gm) was added portionwise. The dark mixture was heated to reflux for 10 minutes and a thick precipitate formed. Water (100 mL) and ethyl acetate (100 mL) were added. The organic layer was separated, dried over magnesium sulfate, filtered through 0.5 cm of silica gel and evaporated to dryness under vacuum. The residue was chromatographed on silica gel using 10% ethyl acetate in hexane. Fractions containing the desired compound were combined and evaporated under reduce pressure to yield the title compound of Step E as a yellow solid (2.79 gm, 89%); m.p. 123°–124° C.; IR (nujol, $cm^{-1}$): 1704 (C=O), 3212 and 3388 ($NH_2$); $^1H$ NMR δ: 1.31–1.36 (t,3H), 3.79 (broad s,2H), 4.26–4.28 (q,2H), 6.26–6.31 (d,1H), 6.99–7.02 (d,1H), 7.05–7.08 (d,1 H), 7.93–7.99 (d,1H).

Step F
Preparation of Phenylmethyl 2-[[[4-chloro-5-(3-ethoxy-3-oxo-1-propenyl)-2-fluorophenyl]amine]carbonyl]-3-azabicyclo[3.1.0]hexane-3-carboxylate A mixture of the compound of Step D, Example 2, (2.7 gm, 11.09 mmol), carbobenzoyloxy (CBZ) protected (±)-3-azabicyclo[3.1.0]hexane-2-carboxylic acid (3.76 gm, 14.41 mmol), DCC (2.97 gm, 14.41 mmol), and 4-dimethylaminopyridine DMAP (39 mg, 1.4 mmol) in methylene chloride (100 mL) was stirred at room temperature for 24 hours. The mixture was filtered and the filtrate was evaporated to dryness. The residue was chromatographed on silica gel using 25% of ethyl acetate in hexane as eluent. The combined desired fractions were evaporated under vacuum to yield the title compound of Step F as a white solid 1.52 gm, 63%; m.p. 58°–60° C. IR (nujol, $cm^{-1}$): 1710 (C=O); $^1H$ NMR δ: 0.22–0.28 (m,1H), 0.75–0.89 (m,2H), 1.19–1.38 (m,5H), 3.43–3.79 (m,3H), 4.21–4.28 (m,2H), 5.01–5.13 (m,2H), 6.42–6.48 (d,1H), 7.18–7.37 (m,7H), 7.95–8.00 (d,1H).

Step G
Preparation of Ethyl 3-[5-[[(3-azabicyclo[3.1.0]hexan-2-yl)carbonyl]amino]-2-chloro-4-fluorophenyl]-2-propenoate To a stirred solution of borontrifluoride etherate (2.27 mL, 2.62 gm, 18.5 mmol) and ethanethiol (4.1 mL, 3.44 gm, 55.5 mmol) under $N_2$, at room temperature was added dropwise a solution of the compound of Step F, Example 2, (900.0 mg, 1.85 mmol) in $CH_2Cl_2$ (1 mL). The resultant solution was stirred at room temperature for 4 hours. Water (100 mL) and $CH_2Cl_2$ (200 mL) were added and the mixture was basified to pH-10 with solution of sodium hydroxide. The organic layer was separated, dried over $MgSO_4$ and evaporated to dryness under reduced pressure. The residue was chromatographed on silica gel using hexane:EtOAc (7:3) as eluent to give the title compound of step G as a white semi-solid 313 mg, 48%. IR (nujol, $cm^{-1}$): 1671.3 and 1723.0 (C=O) and 3364.4 (NH); $^1H$ NMR δ: 0.05–0.07 (q,1H), 0.70–85 (m,1H), 1.31–1.36 (t,3H), 2.02–2.09 (m,2H), 3.01–3.08 (broad s,2H), 3.72–3.76 (s,1H), 4.08–4.18 (q,1H), 4.25–4.28 (m,2H), 6.45–6.52 (d,1H), 7.18–7.20 (d,1H), 7.97–8.02 (d,1H), 8.82–8.85 (d,1H), 9.98 (s,1H).

Step H
Preparation of Ethyl 3-[2-chloro-4-fluoro-5-(hexahydro-1,3-dioxocyclopropa[3,4]-pyrrolo[1,2-c]imidazol-2(3H)-yl]phenyl]-2-propenoate To a stirred solution of the compound of Step G, Example 2, (300.0 mg, 0.85 mmol) and triethylamine (1.18 mL, 8.5 mmol) in $CH_2Cl_2$ (50 mL), under $N_2$, at room temperature, was added dropwise a solution of triphosgene (84.0 mg, 0.28 mmol) in $CH_2Cl_2$ (10 mL) over a period of 15 minutes. The solution was stirred at room temperature for 10 minutes. A mixture of $CH_2Cl_2$ (100 mL) and $H_2O$ (50 mL) was added. The organic layer was separated, dried over $MgSO_4$ and concentrated under reduced pressure to dryness. The residue was chromatographed on silica gel using 25% ethyl acetate in hexane as eluent. Fractions containing the title compound were combined and evaporated under reduce pressure to yield the title compound, a compound of the invention, as a white solid (84.0 mg), 26%; m.p. 154°–156° C., IR (nujol, $cm^{-1}$): 1720.4 (C=O); $^1H$ NMR δ: 0.61–0.63 (q,1H), 1.32–1.36 (m,4H), 2.01–2.03 (m,1H), 2.11–2.18 (m,1H), 3.12–3.18 (d,1H), 4.18–4.28 (m,4H), 6.37–6.41 (d,1H), 7.32–7.35 (d,1H), 7.59–7.62 (d,1H), 7.94–7.99 (d,1H).

EXAMPLE 3

Preparation of 2-[7-fluoro-3,4-dihydro-3-oxo-4-(2-propynyl)-2H-1,4-benzoxazin-6-yl]tetrahydrocyclopropa-[3,4]pyrrolo[1,2-c]imidazole-1,3(2H,5H)-dione Step A
Preparation of Ethyl (5-fluoro-2-nitrophenoxy)acetate A stirred mixture of 5-fluoro-2-nitrophenol (100.0 gm, 0.64 mol), ethyl bromoacetate (77.6 mL, 116.9 gm, 0.78 mol) and $K_2CO_3$ (175.9 gm, 1.27 mol) in acetonitrile (800 mL), under $N_2$, was heated to reflux for 1 hour. The reaction mixture was filtered and the filtrate was washed with brine (200 mL), dried ($MgSO_4$) and evaporated to dryness to give the title compound of Step A, Example 3, as an orange solid (150.0 gm), 97%; m.p. 37°–39° C.; $^1H$ NMR δ: 1.28–1.32 (t,3H), 4.23–4.29 (m,2H), 4.77 (s,2H), 6.64–6.68 (d,1H), 6.79–6.83 (t,1H), 7.96–8.01 (q,1H).

Step B
Preparation of 7-fluoro-2H-1,4-benzoxazin-3(4H)-one

To a solution of the compound of Step A, Example 3, (50.0 gm) in THF (100 mL), under $N_2$, was carefully added 10% Palladium on carbon (catalytic amount). The reaction vessel was pressurized with $H_2$ (45 psi) and shaken on a Parr hydrogenator for 4 hours. The reaction mixture was filtered through a CELITE (siliceous earth) bed and the filtrate was evaporated to dryness under vacuum. The residue was triturated with $Et_2O$ to obtain the title compound of Step B as a white solid (32.0 gm), 93%; m.p. 200°–202° C.; $^1$H NMR δ: 4.58 (s,2H), 6.79–6.90 (m,3H), 10.72 (s,1H).

Step C
Preparation of 7-fluoro-6-nitro-2H-1,4-benzoxazin-3(4H)-one

To a stirred solution of the compound of Step B, Example 3, (48.9 gm, 292.8 mmol) and concentrated $H_2SO_4$ (100 mL), under $N_2$, was added a 26 mL mixture of $HNO_3$ (69–71%) and concentrated $H_2SO_4$ dropwise at 25°–35° C. (ice-bath). The resultant solution was stirred at room temperature for 10 minutes. 400 mL of ice water was added portionwise to the solution at 0° C. (ice-bath) followed by the addition of EtOAc (1.5 L). The organic layer was separated, dried ($MgSO_4$) and evaporated to dryness to give the title compound of Step C as a tan solid (60.0 gm), 96%; m.p. 200°–202° C.; IR (nujol, cm$^{-1}$): 1703.5 (C=O); $^1$H NMR δ: 4.79 (s,2H), 7.26–7.29 (d,1H), 7.63–7.64 (d,1H), 11.05 (s,1H).

Step D
Preparation of 7-fluoro-6-nitro-4-(2-propynyl)-2H-1,4-benzoxazin-3(4H)-one To a stirred solution of the compound of Step C, Example 3, (4.0 gm, 18.86 mmol) in DMF (100 mL), under $N_2$, at 5° C. (ice-bath) was added sodium hydride (60% in mineral oil, 753.0 mg, 18.86 mmol) portionwise. When gas evolution stopped, propargyl bromide (80%, 2.24 gm, 18.86 mmol) was added dropwise. The dark solution was stirred at room temperature for 17 hours. The reaction was carefully poured into water (150 mL) and EtOAc (600 mL) was added. The organic layer was separated and evaporated to dryness. The residue was chromatographed on silica gel using 25% of ethyl acetate in hexane as eluent. Fractions of compound of interest were combined and evaporated to dryness to yield the title compound of Step D, Example 3, as a yellow solid (2.7 gm), 57%; m.p. 105°–107° C.; IR (nujol, cm$^{-1}$): 1695.3 (C=O) and 2120.6 (C≡C); $^1$H NMR δ: 4.76–4.81 (m,4H), 6.91–6.94 (d,1H), 7.97–7.98 (d,1H), 2.35 (s,1H).

Step E
Preparation of 6-amino-7-fluoro-4-(2-propynyl)-2H-1,4-benzoxazin-3(4H)-one Iron powder (6.0 gm, 107.9 mmol) was added portionwise over a 1.5 hour period under $N_2$, at room temperature, to a stirred solution of the compound of Step D, Example 3, (2.7 gm, 10.8 mmol) in methanol (100 mL). NaOAc (1.67 gm) was added and the mixture was filtered. The filtrate was basified to pH 9 using 50% NaOH. The mixture was filtered and the filtrate was evaporated to dryness. Flash chromatography yielded the title compound as a tan solid (300 mg), 13%; m.p. 132°–134° C.; IR (nujol, cm$^{-1}$): 3342 and 3287.8 ($NH_2$) and 2100 (C≡C).

Step F
Preparation of phenylmethyl 2-[[[7-fluoro-3,4-dihydro-3-oxo-4-(2-propynyl)-2H-1,4-benzoxazin-6-yl]amino]carbonyl]-1-pyrrolidinecarboxylate A mixture of the compound of Step E, Example 3, (1.3 gm), CBZ protected (±)-3-azabicyclo[3.1.0]hexane-2-carboxylic acid (2.3 gm), DCC (1.8 gm), DMAP (2.6 mg) in $CH_2Cl_2$ (75 mL) was stirred at room temperature for 3 days. The reaction mixture was filtered and the filtrate was evaporated to dryness. Flash chromatography yielded the title compound of Step F as a white solid (1.41 gm), 51%; m.p. 72°–74° C.; IR (nujol, cm$^{-1}$): 1691 (C=O) and 3285.9 (NH); $^1$H NMR δ: 0.21–0.25 (m,1H), 0.83–0.85 (m,1H), 1.62–1.68 (m,2H), 2.01–2.04 (m,1H), 3.50–3.54 (m,1H), 3.75–3.79 (d,1H), 4.57–4.68 (m,3H), 5.07–5.09 (m,2H), 6.68–7.02 (d,1H), 7.26–7.36 (m,7H), 8.30–8.32 (d,1H) 8.82–8.84 (s,1H).

Step G
Preparation of N-[7-fluoro-3,4-dihydro-3-oxo-4-(2-propynyl)-2H-1,4-benzoxazin-6-yl]-3-azabicyclo[3.1.0]hexane-2-carboxamide To a solution of boron trifluoride etherate (1.57 gm, 10.8 mmol) and ethanethiol (2.31 mL, 1.94 gm, 32.32 mmol) under $N_2$, at room temperature was added dropwise a solution of the compound of Step F, Example 3, (500.0 mg) in $CH_2Cl_2$ (1 mL). The resultant clear solution was stirred at room temperature for 48 hours and the reaction was scrubbed with a bleach/50% NaOH/$H_2O$-20%. 30 mL of water was added dropwise at room temperature followed by $CH_2Cl_2$ (30 mL). The aqueous layer was separated and basified to pH 10 using 50% NaOH. Additional 30 mL of $CH_2Cl_2$ was added and the organic layer was separated, dried ($MgSO_4$) and evaporated to dryness to give the title compound of Step G as a white solid (200 mg), 57%; m.p. 196°–198° C.; IR (nujol, cm$^{-1}$): 1676.0 (C=O), 3357.7 and 3301.7 (NH); $^1$H NMR δ: 0.08–0.09 (m,1H), 0.71–0.77 (m,1H), 1.41–1.43 (m,1H), 2.01–2.08 (m,1H), 2.11–2.17 (broad s, 1H), 2.31–2.32 (m,1H), 3.02 (s,2H), 3.72 (s,1H), 4.61 (s,2H), 4.75–4.81 (dd,2H), 6.79–6.81 (d,1H), 8.44–8.46 (d,1H), 9.85 (broad s,1H).

Step H
Preparation of 2-[7-fluoro-3,4-dihydro-3-oxo-4-(2-propynyl)-2H-1,4-benzoxazin-6-yl]tetrahydrocyclopropa[3,4]-pyrrolo[1,2-c]imidazole-1,3(2H,5H)-dione A solution of triphosgene (57 mg) in $CH_2Cl_2$(1 mL) was added dropwise to a stirred solution of triethylamine (0.2 mL) and the compound of Step G, Example 3, (190 mg) in $CH_2Cl_2$ (50 mL) under $N_2$ at room temperature. The solution was stirred at room temperature for 20 minutes. 30 mL of water was added. The organic layer was separated, dried ($MgSO_4$) and evaporated to dryness. Flash chromatography yielded the title compound of Step H, a compound of the invention, as a white solid (127 mg), 62%; m.p. 217°–219° C.; IR (nujol, cm$^{-1}$): 3253.6 and 2129.3 (C≡C), 1625 and 1715 (C=O).

$^1$H NMR δ: 0.61–0.64 (m,1H), 1.22–1.31 (m,1H), 2.01–2.11 (m,1H), 2.17–2.22 (m,1H), 2.25 (s,1H), 3.12–3.17 (dd,1H), 4.17–4.18 (m,2H), 4.67–4.68 (s,4H), 6.84–6.93 (d,1H), 7.11–7.14 (d,1H).

EXAMPLE 4

Preparation of Methyl 2-chloro-4-fluoro-5-(hexahydro-1,3-dioxocyclopropa[3,4]pyrrolo[1,2-c]imidazol-2(3H)-yl]benzoate Step A
Preparation of 5-amino-2-chloro-4-fluorobenzoic acid A solution of the compound of Step A in Example 2 (25.0 gm) in acetic acid (100 mL), under $N_2$, was heated to reflux. The heat source was removed and iron powder (6.38 gm) was added portionwise. The resultant mixture was stirred at ambient temperature for 15 minutes. 200 mL of water was added followed by addition of 500 mL of ethyl acetate. The organic layer was separated, washed with brine (3×50 mL), dried over magnesium sulfate and evaporated to dryness to yield the title compound as a tan solid (14.4 gm), 67%; m.p. 105°–107° C.; IR (nujol, cm⁻¹): 3396.9 and 3491.8 (NH₂) and 1702.0 (C=O).

Step B
Preparation of Methyl 5-amino-2-chloro-4-fluorobenzoate

Thionyl chloride (18.09 gm) was added dropwise to a solution of the compound of Step A of Example 4 (10.0 gm) in methanol (100 mL) under N₂ at 0° C. (ice-bath). The ice-bath was removed and the solution was heated to reflux for 2 hours. The solution was cooled to room temperature and then poured slowly into water (300 mL). The aqueous solution was extracted with 500 mL ethyl acetate. The organic layer was separated and dried over magnesium sulfate. Evaporation to dryness followed by flash chromatography yielded the title compound as a tan solid (4.3 gm), 40%; m.p. 76°–78° C.;

IR (nujol, cm⁻¹): 3404.1, 3324.5, and 1706.1; ¹H NMR δ: 3.87–3.91 (m,5H), 7.07–7.11 (d,1H), 7.29–7.33 (d,1H).

Step C
Preparation of Phenylmethyl 2-[[[4-chloro-2-fluoro-5-(methoxycarbonyl)phenyl]amino]-carbonyl]-3-azabicyclo-[3.1.0]hexane-3-carboxylate A solution of DCC (5.4 gm), DMAP (320 mg), CBZ protected (±)-3-azabicyclo[3.1.0]hexane-2-carboxylic acid (6.8 gm) and the compound of Step B of Example 4 (4.1 gm) in CH₂Cl₂ (150 mL), under N₂, was stirred at room temperature for 17 hours. The reaction mixture was filtered and the filtrate was evaporated to dryness. Flash chromatography yielded the title compound as a sticky white solid (4.8 gm), 53%; m.p. (semi-solid); IR (nujol, cm⁻¹): 1708.6 and 3284.9; ¹H NMR δ: 1.21–1.24 (m,1H), 0.72–0.89 (m,2H), 0.91–0.99 (t,3H), 1.21–1.37 (m,4H), 1.41–1.48 (m,2H), 1.66–1.71 (m,4H), 3.51–3.77 (m,2H), 4.31–4.37 (m,2H), 4.99–5.14 (m,2H), 7.24–7.39 (m,7H).

Step D
Preparation of Methyl 2-chloro-4-fluoro-5-[2-pyrrolidinylcarbonyl)amino]benzoate To a solution of the compound of Step C of Example 4 (4.8 gm) in THF (100 mL), under N₂, was carefully added 10% Palladium on carbon (catalytic amount). The reaction mixture was pressurized with H₂ (45 psi) and shaken on a Paar hydrogenator for 2 hours. The mixture was filtered through a CELITE (siliceous earth) bed and the filtrate was evaporated to dryness. Flash chromatography yielded the title compound as a white solid (2.38 gm), 71%; m.p. 151°–153° C.

Step E
Preparation of Methyl 2-chloro-4-fluoro-5-(hexahydro-1,3-dioxocyclopropa[3,4]pyrrolo[1,2-c]Imidazol-2(3H)-yl)benzoate A solution of triphosgene (135 mg) in CH₂Cl₂ (2 mL) was added dropwise over a period of 10 minutes under N₂, at 0° C. (ice-bath) to a stirred solution of the compound of Step D of Example 4 (300 mg) in CH₂Cl₂ (30 mL). The resultant mixture was stirred an additional 10 minutes at 0° C. (ice-bath). 50 mL of H₂O was added and the aqueous mixture was extracted with CH₂Cl₂ (100 mL). The organic layer was separated and dried over magnesium sulfate. The dried organic layer was evaporated under vacuum to dryness. The residue was chromatographed on silica gel using 25% of ethyl acetate in hexane as eluent. The fractions with the first eluting product were combined and evaporated under reduced pressure to yield the trans-isomer of the title compound, a compound of the invention, as a white solid (150 mg), 46%; m.p. 59°–62° C.; IR (nujol, cm⁻¹): 1726.9; ¹H NMR δ: 0.61–0.68 (m,1H), 1.22–1.29 (m,1H), 2.01–2.04 (m,1H), 2.14–2.19 (m,1H), 3.17–3.18 (d,1H), 3.97 (s,3H), 4.18–4.21 (m,2H), 7.36–7.38 (d,1H), 7.92–7.95 (d,1H).

The fractions with the slower moving product were combined and evaporated under reduced pressure to yield the cis-isomer of the title compound, a compound of the invention, as a white solid (100 mg), 31%; m.p. 142°–143° C. ¹H NMR (CDCl₃, 400 MHz): δ0.28–0.29 (m,1H), 0.87–0.89 (m,1H), 1.75–1.79 (m,1H), 1.93–1.95 (m,1H), 3.39–3.40 (dd,1H), 3.92 (s,3H), 3.95–3.98 (d,1H), 4.52–4.53 (d,1H), 7.35–7.37 (d,1H), 7.88–7.90 (d,1H).

EXAMPLE 5

Preparation of 3-[[[4-chloro-2-fluoro-5-(2-propynyloxy)phenyl]-amino]carbonyl]-3-azabicyclo[3.1.0]hexane-2-carboxylic acid Step A
Preparation of 1-chloro-5-fluoro-4-isocyanato-2-(2-propynyloxy)benzene To a stirred solution of 4-chloro-2 fluoro-5-[(2-propynyl)oxy]-aniline (5.0 gm) and triethylamine (5.1 gm) in CH₂Cl₂ (100 mL) under N₂, at 10° C. (ice-bath) was added triphosgene portionwise. The solution was heated to reflux for 5 hours. The solution was evaporated under vacuum and suspended in Et₂O (200 mL). The suspension was filtered and the filtrate evaporated to dryness to give the title compound as a white solid (4.68 gm), 83%; IR (nujol, cm⁻¹): 3295 (C≡C) and 2257 (N=C=O). This crude product was used as such in the next reaction.

Step B
Preparation of 3-[[[4-chloro-2-fluoro-5-(2-propynyloxy)phenyl]amino]carbonyl]-3-azabicyclo[3.1.0]hexane-2-carboxylic acid A solution of the compound of Step A in Example 5 (3.0 gm) and the compound of Step E in Example 1 (1.69 gm) in CH₂Cl₂ (100 mL), under N₂, was stirred at room temperature for 17 hours. The solution was evaporated to dryness. Flash chromatography yielded the title compound, a compound of the invention, as a white solid (1.2 g), 28%; m.p. 165°–170° C.; IR (nujol, cm⁻¹): 2127 (C≡C), 1647 (C=O), 3293 and 3499.

The following Tables illustrate the compounds of the invention that are produced by the processes of the invention.

The following abbreviations are used in the Tables which follow. All alkyl groups are the normal isomers unless indicated otherwise.

| n = normal | Et = ethyl | i = iso | Pr = propyl |
|---|---|---|---|

TABLE 1

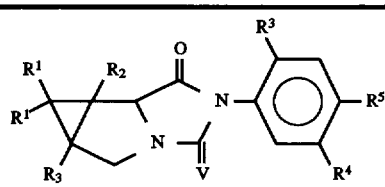

Formula I wherein Q is Q-1

| R¹ | R² | R³ | R⁴ | R⁵ | V |
|---|---|---|---|---|---|
| H | H | Cl | OCH(CH₃)₂ | Cl | O |
| H | H | Cl | OCH₂— | Cl | O |
| H | H | F | OCH(CH₃)₂ | Cl | O |
| H | H | F | OCH₂C≡CH | Cl | O |

TABLE 1-continued

Formula I wherein Q is Q-1

| R¹ | R² | R³ | R⁴ | R⁵ | V |
|---|---|---|---|---|---|
| H | H | Cl | OCH$_2$C≡CH | Cl | O |
| H | H | F | H | Cl | O |
| H | H | F | OCH$_2$CH$_2$OCH$_2$CH$_3$ | Cl | O |
| H | H | F | OCH(CH$_3$)(C≡CH) | Cl | O |
| H | H | F | OCH$_2$C$_6$H$_5$ | Cl | O |
| H | H | F | OCH$_2$C$_6$H$_4$-4-CF$_3$ | Cl | O |
| H | H | F | OCH$_2$C$_6$H$_4$-2-Cl | Cl | O |
| H | H | F | OCH$_2$C$_6$H$_4$-3-Cl | Cl | O |
| H | H | F | OCH(C≡CH)(CH(CH$_3$)$_2$) | Cl | O |
| H | H | F | OC(CH$_3$)(C≡CH)(CH$_2$CH$_3$) | Cl | O |
| H | H | F | OCH(C≡CH)(CH$_2$)$_4$CH$_3$ | Cl | O |
| H | H | F | OCH(C≡CH)(CH$_2$CH$_3$) | Cl | O |
| H | H | F | OCH$_2$C≡C—CH$_3$ | Cl | O |
| H | H | F | OCH$_2$CH$_2$C≡CH | Cl | O |
| H | H | F | OCH(CH$_3$)(CH$_2$C≡CH) | Cl | O |
| H | H | F | OCH(CH$_2$CH$_3$)(CH$_2$C≡CH) | Cl | O |
| H | H | F | OCH(CO$_2$CH$_2$CH$_3$)(CH$_2$)$_4$CH$_3$ | Cl | O |
| H | H | F | OP(O)(OCH$_2$CH$_3$)$_2$ | Cl | O |
| H | H | F | OCH$_2$C≡CH | Cl | S |
| H | F | F | OCH$_2$C≡CH | Cl | O |
| F | F | F | SCH$_2$CO$_2$Me | Cl | O |
| H | H | F | CO$_2$CH$_3$ | Cl | O |
| H | H | F | CH=(γ-butyrolactone) | Cl | O |
| H | H | F | CH$_2$CH$_2$CO$_2$CH$_2$CH$_3$ | Cl | O |
| H | H | F | CHC(CH$_3$)(CO$_2$Et) | Cl | O |
| H | H | F | CHCHCO$_2$Et | Cl | O |
| H | H | F | CHO | Cl | O |
| H | H | F | CH=CHCO$_2$Me | Cl | O |
| H | H | F | CH$_2$CHCHCO$_2$Et | Cl | O |
| H | H | F | SCH(CO$_2$Et)(C$_5$H$_{11}$) | Cl | O |
| H | F | F | Cl | OMe | S |
| H | F | F | OCHMe$_2$ | OMe | O |
| F | F | Cl | H | Br | O |
| H | H | F | OCH$_2$C(O)NHMe | Cl | S |
| H | H | F | SO$_2$Me | Cl | O |
| H | CH$_3$ | F | SCH$_2$C≡CH | Cl | O |
| H | H | F | OCF$_2$CHCF$_2$ | Cl | O |
| H | H | F | OCH$_2$CF$_3$ | Cl | O |

TABLE 2

Formula I wherein Q is Q-5

| R¹ | R² | R³ | R⁷ | R⁸ | V |
|---|---|---|---|---|---|
| H | H | F | H | CH$_2$CH$_3$ | O |
| H | H | F | H | CH$_2$-cyclopropyl | O |
| H | H | F | H | CHFCO$_2$CH$_2$CH$_3$ | O |
| H | H | F | H | CH$_2$CCH | O |
| H | H | F | H | CH$_2$CHCHCO$_2$CH$_2$CH$_3$ | O |
| H | H | F | H | CH$_2$C≡CH | O |
| H | H | Cl | H | CH$_2$C≡CH | O |
| F | F | F | H | CH$_2$C≡CH | O |
| H | H | F | CH$_3$ | CH$_2$C≡CH | O |
| H | H | F | H | CH$_2$CO$_2$Et | O |

TABLE 3

Formula I wherein Q is Q-3

| R¹ | R² | R³ | R⁵ | R⁶ | R⁷ | V | W |
|---|---|---|---|---|---|---|---|
| H | H | F | Cl | H | H | O | O |
| H | H | F | Cl | H | Me | O | S |
| H | H | F | Cl | Me | Me | O | O |
| H | H | Cl | Cl | H | H | O | O |
| H | H | Cl | Cl | Me | Me | O | S |
| H | H | F | Cl | H | H | S | O |

TABLE 4

Formula I wherein Q is Q-4

| R¹ | R² | R³ | R⁸ | V | W |
|----|----|----|----|----|----|
| H | H | F | H | O | O |
| H | H | F | Me | S | O |
| H | H | Cl | H | O | S |
| H | H | Cl | Me | S | O |
| H | H | F | CH(CH₃)₂ | O | S |

TABLE 5

Formula II wherein Q is Q-1

| R¹ | R² | R³ | R⁴ | R⁵ | R²³ | V |
|----|----|----|----|----|-----|---|
| H | H | F | OCH₂C≡CH | Cl | H | O |
| H | H | F | OCH(C≡CH)(CH(CH₃)₂) | Cl | H | O |
| H | H | F | OCH₂C≡CH | Cl | CH₃ | O |
| H | H | F | OCH(C≡CH)(CH(CH₃)₂) | Cl | CH₂CH₃ | O |
| H | F | F | OCH₂C₆H₅ | Cl | CH₃ | O |
| H | H | F | OCH₂C≡CH | Br | H | O |
| F | H | F | OCH₂CH₃ | Br | H | O |
| H | H | Cl | OCH(C≡CH)CH₂CH₃ | Cl | H | O |
| F | H | Cl | OCH(CH₃)₂ | Br | CH₃ | S |

TABLE 6

Formula II wherein Q is Q-5

| R¹ | R² | R³ | R⁸ | R²³ | V |
|----|----|----|----|-----|---|
| H | H | F | CH₂C≡CH | H | O |
| H | H | F | CH₂C≡CH | Me | S |
| H | H | F | CH₂CO₂CH₃ | H | O |
| H | H | Cl | CH₂CO₂CH₂CH₃ | Me | O |

TABLE 7

Formula III wherein Q is Q-1

| R¹ | R² | R³ | R⁴ | R⁵ | X |
|----|----|----|----|----|---|
| H | H | F | OCH₂C≡CH | Cl | Cl |
| H | H | F | OCH(CH₃)₂ | Br | Cl |
| H | H | Cl | OCH(C≡CH)(Et) | Cl | Cl |
| H | H | F | OCH(CH₃)₂ | Cl | CN |
| H | H | F | OCH₂CH₂OCH₃ | OCH₃ | Cl |
| H | H | F | SCH₂CF₃ | Cl | Cl |
| H | H | F | OCH₂CF₃ | Cl | Cl |
| H | H | F | OCH₂C(O)NHMe | Cl | Cl |
| H | H | F | SO₂Me | Cl | Cl |
| H | H | F | OCH₂CH₂OCHF₂ | Cl | Cl |
| H | H | F | SCH₂C≡CH | Cl | Cl |

TABLE 8

Formula III wherein Q is Q-2

| R¹ | R² | R³ | R⁵ | R⁶ | R⁷ | X |
|----|----|----|----|----|----|---|
| H | H | F | Cl | H | H | Cl |
| H | H | F | Cl | CH₃ | CH₃ | Cl |
| H | H | Cl | Cl | H | H | Cl |

TABLE 9

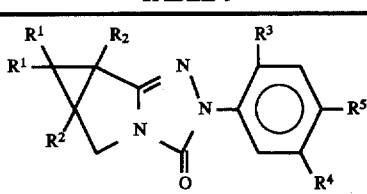

Formula IV wherein Q is Q-1

| R¹ | R² | R³ | R⁴ | R⁵ |
|----|----|----|----|----|
| H | H | F | OCH$_2$C≡CH | Cl |
| H | H | Cl | OCH$_2$CH(CH$_3$)$_2$ | Cl |
| H | H | F | OCH$_2$CH$_3$ | Cl |
| H | H | F | OCH$_2$CO$_2$Me | Cl |
| H | H | F | OC(O)N(CH$_3$)$_2$ | Cl |
| H | H | F | OC(O)NHCH$_3$ | Cl |
| H | H | Cl | OCH$_2$F | Cl |
| H | H | F | 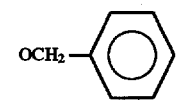 | Cl |

Formulation/Utility

The compounds of Formulae I–IV are useful as herbicides in agriculture. To carry out this utility, any of the compounds of Formulae I–IV can generally be used in formulation with an agriculturally suitable carrier comprising a liquid or solid diluent and/or a surfactant wherein the formulation is consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–74 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J. Typical liquid diluents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltarates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", Chemical Engineering, Dec. 4, 1967, pp 147–48, Perry's Chemical Engineer's Handbook, 4th Ed., McGraw-Hill, N.Y., 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, Weed Control as a Science, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are worked up in conventional ways. Compound 23 refers to the compound listed in Index Table A hereinafter.

Example A

| High Strength Concentrate | |
|---|---|
| Compound 23 | 98.5% |
| silica aerogel | 0.5% |
| synthetic amorphous fine silica | 1.0%. |

Example B

| Wettable Powder | |
|---|---|
| Compound 23 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

| Granule | |
|---|---|
| Compound 23 | 10.0% |
| attapulgite granules (low volatile matter, 0.71/0.30 mm; U.S.S. No. 25–50 sieves) | 90.0%. |

Example D

| Extruded Pellet | |
|---|---|
| Compound 23 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Tests results indicate that the compounds of Formulae I–IV are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds such as morningglory, cocklebur, velvetleaf, giant foxtail, barnyardgrass and lambsquarters, with tolerance to important agronomic crops which include but are not limited to barley, cotton, wheat, rape, sugarbeets, corn, soybeans, rice, and plantation crops including coffee, cocoa, oil palm, rubber, sugarcane, citrus, grapes, fruit trees, nut trees, banana, plantain, pineapple, conifers, e.g., loblolly pine, and turf species Kentucky bluegrass, St. Augustine grass, Kentucky rescue and bermudagrass. Those skilled in the art will appreciate that not all compounds are equally effective against all weeds. Alternatively, the subject compounds are useful to modify plant growth.

Compounds of Formulae I–IV can be used alone or in combination with other commercial herbicides, insecticides or fungicides. A mixture of one or more of the following herbicides with a compound of Formula I can be particularly useful for weed control. Examples of other herbicides with which compounds of this invention can be formulated are: acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di-2-propenylacetamide, 2 -chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumesulam, flumipropyn, fluometuron, fluorochloridone, fluorodifen, fluoroglycofen, flupoxam, fluridone, fluroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S"-dimethyl-2-(difluoromethyl)-4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(α,α-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similar spectrum of control but a different mode of action will be particularly advantageous for resistance management.

A herbicidally effective amount of the compounds of Formulae I–IV is determined by a number of factors. These factors include: formulation selected, method of application, amount and type of vegetation present, growing conditions, etc. In general, a herbicidally effective amount of a compound(s) of Formulae I–IV is applied at rates from about 0.01 to 20 kg/ha with a preferred rate range of 0.02 to 10 kg/ha. One skilled in the art can easily determine application rates necessary for the desired level of weed control.

The following Tests demonstrate the control efficacy of the compounds of Formulae I–IV against specific weeds. The weed control afforded by the compounds is not limited, however, to these species. See Index Tables A–D for compound descriptions.

Index Table A

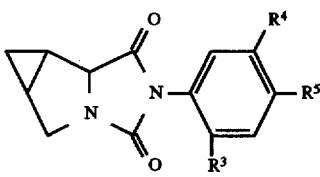

Formula I wherein Q is Q-1

| Cmpd No. | $R^3$ | $R^4$ | $R^5$ | Stereo[a] | m.p. (°C.) |
|---|---|---|---|---|---|
| 1 | Cl | OCH(CH$_3$)$_2$ | Cl | trans | 55–57 |
| 2 | F | OCH$_2$C≡CH | Cl | — | 52–54 |
| (Ex. 1) 3 | F | OCH(CH$_3$)$_2$ | Cl | trans | oily solid[b] |
| 4 | F | CO$_2$CH$_3$ | Cl | trans | 59–62 |
| (Ex. 4) 5 | Cl | O-cyclopentyl | Cl | — | 58–60 |
| 6 | Cl | OCH$_2$CN | Cl | — | 65–67 |
| 7 | Cl | OCH$_2$CO$_2$CH$_3$ | Cl | — | 131–133 |
| 8 | Cl | OCH$_2$-cyclopropyl | Cl | — | 61–63 |
| 9 | F | H | Cl | — | 89–90 |
| 10 | Cl | OCH$_2$C≡CH | Cl | — | 50–52 |
| 11 | F | SCH$_2$CO$_2$CH$_3$ | Cl | — | 44–46 |
| 12 | F | OP(O)(OCH$_2$CH$_3$)$_2$ | Cl | — | oil[b] |
| 13 | F | OCH$_2$CH$_2$OCH$_2$CH$_3$ | Cl | — | oil[b] |
| 14 | F | (lactone structure CH=) | Cl | — | 89–91 |
| 15 | F | CH=C(CH$_3$)CO$_2$CH$_2$CH$_3$ | Cl | — | 36–40 |
| 16 | F | CO$_2$CH$_2$CO$_2$CH$_2$CH$_3$ | Cl | — | 38–42 |
| 17 | F | CH$_2$CH$_2$CO$_2$CH$_2$CH$_3$ | Cl | — | 75–77 |
| 18 | F | CH=CHCO$_2$CH$_2$CH$_3$ | Cl | — | 154–156 |
| (Ex. 2) 19 | F | CHO | Cl | — | 114–116 |
| 20 | F | CO$_2$CH$_2$CH$_2$CH$_2$CH$_3$ | Cl | — | oil[b] |
| 21 | F | CO$_2$CH$_3$ | Cl | cis | 142–143 |
| (Ex. 4) 22 | F | O-cyclopentyl | Cl | — | 100–112 |
| 23 | F | OCH(CH$_3$)C≡CH | Cl | — | 46–48 |
| 24 | F | OCH$_2$-(4-CF$_3$—Ph) | Cl | — | 147–149 |
| 25 | F | OCH$_2$-(3-Cl—Ph) | Cl | — | 197–199 |
| 26 | F | OCH$_2$-(2-Cl—Ph) | Cl | — | 152– |

-continued

Index Table A

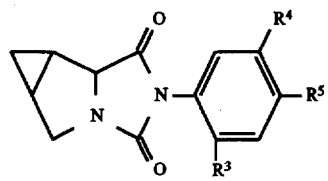

Formula I wherein Q is Q-1

| Cmpd No. | $R^3$ | $R^4$ | $R^5$ | Stereo[a] | m.p. (°C.) |
|---|---|---|---|---|---|
| 27 | F | CH=CHCO$_2$CH$_3$ | Cl | — | 154 159–161 |
| 28 | F | OCH$_2$Ph | Cl | — | 126–128 |
| 29 | F | OCH(C≡CH)CH(CH$_3$)$_2$ | Cl | trans/mix | 60–62 |
| 30 | F | OCH(C≡CH)CH(CH$_3$)$_2$ | Cl | cis/mix | 61–63 |
| 31 | F | OC(CH$_3$)(C≡CH)CH$_2$CH$_3$ | Cl | trans/mix | 60–63 |
| 32 | F | OC(CH$_3$)(C≡CH)CH$_2$CH$_3$ | Cl | cis/mix | oil[b] |
| 33 | F | OCH(C≡CH)(CH$_2$)$_4$CH$_3$ | Cl | trans/mix | oil[b] |
| 34 | F | OCH(C≡CH)CH$_2$CH$_3$ | Cl | trans/mix | oil[b] |
| 35 | F | OCH$_2$C≡CCH$_3$ | Cl | — | 114–116 |
| 36 | F | OCH$_2$CH$_2$C≡CH | Cl | — | 103–105 |
| 37 | F | OCH(CH$_3$)CH$_2$C≡H | Cl | — | 51–53 |
| 38 | F | OCH(CH$_2$CH$_3$)CH$_2$C≡CH | Cl | — | oil[b] |
| 39 | F | SCH[(CH$_2$)$_4$CH$_3$]CO$_2$CH$_2$CH$_3$ | Cl | — | oil[b] |
| 40 | F | OCH[(CH$_2$)$_4$CH$_3$]CO$_2$CH$_2$CH$_3$ | Cl | — | oil[b] |

[a]This column indicates the stereochemistry of the compound. "Trans" and "Cis" is the relative orientation between the cyclopropyl ring and the imidazolinedione ring. "Mix" indicates that the compound is a mixture of diastereomers due to the remote chiral center on $R^4$. A dash (—) indicates that the relative stereochemistry was not determined or the compound is a mixture of trans and cis. All compounds are racemic.
[b]See Index Table D for $^1$HNMR data.

Index Table B

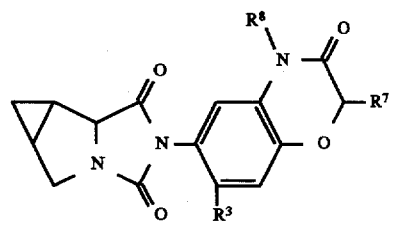

Formula I wherein in Q is Q-5

| Cmpd No. | $R^3$ | $R^7$ | $R^8$ | Stereo[a] | m.p. (°C.) |
|---|---|---|---|---|---|
| 41 | F | H | CH$_2$CH$_3$ | — | 204–206 |
| 42 (Ex. 3) | F | H | CH$_2$C≡CH | — | 217–219 |
| 43 | F | H | CH$_2$-cyclopropyl | — | 82–85 |
| 44 | F | H | CH$_2$CH$_2$CH(CH$_3$)$_2$ | — | 71–73 |
| 45 | F | H | CHFCO$_2$CH$_2$CH$_3$ | — | 75–77 |

Index Table B

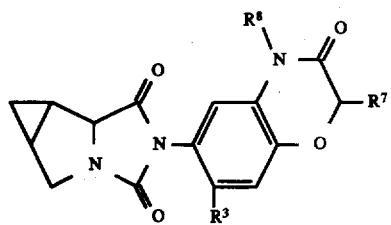

Formula I wherein in Q is Q-5

| Cmpd No. | $R^3$ | $R^7$ | $R^8$ | Stereo[a] | m.p. (°C.) |
|---|---|---|---|---|---|
| 46 | F | H | $CH_2CO_2CH_2CH_3$ | — | 142–144 |
| 47 | F | $CH_3$ | $CH_2C\equiv CH$ | — | 155–157 |
| 48 | F | H | $CH_2CH=CHCO_2CH_2CH_3$ | — | 180–182 |

[a]This column indicates the stereochemistry of the compound. "Trans" and "Cis" is the relative orientation between the cyclopropyl ring and the imidazolinedione ring. A dash (—) indicates that the relative stereochemistry was not determined or the compound is a mixture of trans and cis. All compounds are racemic.

Index Table C

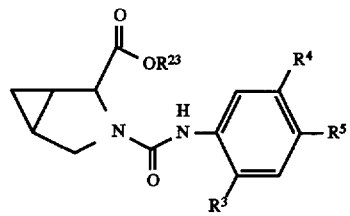

Formula III wherein Q is Q-1

| Cmpd No. | $R^3$ | $R^4$ | $R^5$ | $R^{23}$ | Stereo[a] | m.p. (°C.) |
|---|---|---|---|---|---|---|
| 49 | F | $OCH_2Ph$ | Cl | H | — | 143–145 |
| 50 | F | $OCH_2C\equiv CH$ | Cl | H | — | 165–170 |
| (Ex. 5) 51 | F | $OCH(C\equiv CH)CH(CH_3)_2$ | Cl | H | — | 61–65 |
| 52 | F | $OCH(CH_3)C\equiv CH$ | Cl | H | — | 157–159 |
| 53 | F | $OCH_2C\equiv CH$ | Cl | $CH_3$ | — | 110–112 |
| 54 | F | $OCH(CH_3)C\equiv CH$ | Cl | $CH_3$ | — | 62–64 |

[a]This column indicates the stereochemistry of the compound. "Trans" and "Cis" is the relative orientation between the cyclopropyl ring and the $CO_2R^{23}$ group. A dash (—) indicates that the relative stereochemistry was not determined or the compound is a mixture of trans and cis. All compounds are racemic.

Index Table D

| Cmpd No. | $^1$H NMR Data ($CDCl_3$ solution)[a] |
|---|---|
| 3 | δ: 0.18 (m,1H), 0.82–0.85 (m,1H), 1.37–1.40 (d,6H), 1.70–1.80 (m,1H), 1.90–1.99 (m,1H), 3.31–3.40 (dd,1H), 3.94–3.98 (d,1H), 4.47–4.51 (m,2H), 6.79–6.82 (d,1H), 7.25–7.28 (d,1H). |
| 12 | δ: 0.59–0.63 (q,1H), 1.19–1.23 (t,2H), 1.24–1.29 (m,1H), 1.37–1.61 (m,5H), 2.12–2.18 (m,1H), 3.11–3.18 (d,1H), 3.47–3.49 (q,2H), 4.21–4.32 (m,4H), 7.31–7.36 (d,1H), 7.52–7.59 (d,1H). |
| 13 | δ: 0.59–0.62 (q,1H), 1.20–1.25 (m,4H), 2.00–2.08 (m,1H), 2.10–2.20 (m,1H), 3.10–3.19 (dd,1H), 3.61–3.63 (q,2H), 3.80–3.84 (q,2H), 4.15–4.18 (m,4H), 6.90–6.94 (d,1H), 7.29 (s,1H). |
| 20 | δ: 0.49–0.69 (dq,1H), 0.97–0.99 (t,1H), 1.18–1.32 (m,3H), 1.21–1.32 (m,1H), 1.61–1.9 (m,4H), 2.08–2.19 (m,1H), 3.0–3.19 (dd,1H), 3.80–3.90 (m,1H), 4.05–4.10 (m,1H), 4.30–4.38 (m,1H), 7.35–7.39 (d,1H), 7.90–7.92 (d,1H). |
| 32 | δ: 0.05–0.09 (m,1H), 1.80–1.88 (q,1H), 1.90–1.02 (m,1H), 1.12–1.13 (t,3H), 1.56–1.59 (d,4H), 1.70–1.79 (m,1H), 1.85–2.02 (m,2H), 3.32–3.39 (dd,1H), 3.94–3.99 (d,1H), 4.44–4.45 (d,1H), 7.24–7.27 (d,1H), 7.44–7.46 (d,1H). |
| 33 | δ: 0.60–0.65 (q,1H), 1.85–1.97 (m,3H), 1.35–1.36 (m,6H), 1.95–2.02 (m,4H), 2.10–2.19 (m,1H), 2.55–2.56 (m,1H), 3.09–3.19 (d,1H), 4.16 (s,1H), 4.19–4.22 (m,1H), 4.63–470 (t,1H), 7.08–7.12 (t,1H), 7.27–7.29 (d,1H). |
| 34 | δ: 1.59–1.65 (m,1H), 1.12–1.17 (t,3H), 1.22–1.32 (m,1H), 2.03–2.05 (m,3H), 2.10–2.19 (m,1H), 3.10–3.19 (d,1H), 4.16 (s,1H), 4.18–4.23 (m,1H), 2.61–2.68 (t,1H), 7.08–7.11 (t,1H), 7.27–7.30 (d,1H). |
| 38 | δ: 0.61–0.64 (m,1H), 1.00–1.05 (m,3H), 1.24–1.33 (m,1H), 1.81–1.97 (m,2H), 2.04–2.05 (m,2H), 2.11–2.19 (m,1H), 2.51–2.62 (m,2H), 3.12–3.18 (d,1H), 4.16 (s,1H), 4.19–4.22 (m,1H), 4.27–4.30 (t,1H), 6.92–6.98 (m,1H), 7.27–7.29 (d,1H). |
| 39 | δ: 0.59–0.62 (m,1H), 0.85–0.89 (m,3H), 1.13–1.18 (t,3H), 1.30–1.33 (m,5H), 1.40–1.43 (m,1H), 3.10–3.19 (d,1H), 3.60–3.79 (m,2H), 4.03–4.21 (m,4H), 7.30–7.36 (d,1H), 7.52–7.58 (d,1H). |

Index Table D-continued

| Cmpd No. | $^1$H NMR Data (CDCl$_3$ solution)$^a$ |
|---|---|
| 40 | δ: 0.59–0.62 (m,1H), 0.85–0.92 (m,3H), 1.24–1.26 (m,4H), 1.30–1.39 (m,4H), 1.45–1.58 (m,2H), 1.98–2.08 (m,3H), 2.11–2.18 (m,1H), 3.08–3.18 (d,1H), 4.12–4.26 (m,4H), 4.55–4.61 (m,1H), 6.78–6.82 (m,1H), 7.22–7.24 (d,1H). |

$^a$$^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dq)-doublet of quartets.

TEST A

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant. At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| Rate 1000 g/ha | COMPOUND 41 |
|---|---|
| POSTEMERGENCE | |
| Barley | 10 |
| Barnyardgrass | 10 |
| Bedstraw | 10 |
| Blackgrass | 10 |
| Cheatgrass | — |
| Chickweed | 10 |
| Cocklebur | 10 |
| Corn | 9 |
| Cotton | 10 |
| Crabgrass | 10 |
| Downy brome | 10 |
| Giant foxtail | 10 |
| Lambsquarter | 10 |
| Morningglory | 10 |
| Nutsedge | 10 |
| Rape | 10 |
| Rice | 10 |
| Sorghum | 10 |
| Soybean | 10 |
| Sugar beet | 10 |
| Velvetleaf | 10 |
| Wheat | 10 |
| Wild buckwheat | 10 |
| Wild oat | 10 |
| PREEMERGENCE | |
| Barley | 10 |
| Barnyardgrass | 10 |
| Bedstraw | 10 |
| Blackgrass | 9 |
| Cheatgrass | — |
| Chickweed | 10 |
| Cocklebur | 10 |
| Corn | 10 |
| Cotton | 10 |
| Crabgrass | 10 |
| Downy brome | 10 |
| Giant foxtail | 10 |
| Lambsquarter | 10 |
| Morningglory | 10 |
| Nutsedge | 10 |

TABLE A-continued

| | |
|---|---|
| Rape | 10 |
| Rice | 10 |
| Sorghum | 10 |
| Soybean | 10 |
| Sugar beet | 10 |
| Velvetleaf | 10 |
| Wheat | 10 |
| Wild buckwheat | 10 |
| Wild oat | 10 |

| | COMPOUND | | | |
|---|---|---|---|---|
| Rate 400 g/ha | 1 | 2 | 9 | 23 |
| POSTEMERGENCE | | | | |
| Barley | 8 | 9 | 6 | 10 |
| Barnyardgrass | 10 | 10 | 9 | 10 |
| Bedstraw | 8 | 10 | 9 | 10 |
| Blackgrass | 6 | 10 | 3 | 9 |
| Cheatgrass | — | — | — | — |
| Chickweed | 6 | 10 | 4 | 9 |
| Cocklebur | 8 | 10 | 9 | 10 |
| Corn | 7 | 9 | 8 | 6 |
| Cotton | 10 | 10 | 10 | 10 |
| Crabgrass | 8 | 9 | 9 | 9 |
| Downy brome | 5 | 8 | 3 | 9 |
| Giant foxtail | 6 | 10 | 9 | 9 |
| Lambsquarter | 10 | 10 | 10 | 10 |
| Morningglory | 8 | 10 | 9 | 10 |
| Nutsedge | 5 | 6 | 6 | 6 |
| Rape | 6 | 10 | 10 | 10 |
| Rice | 7 | 10 | 9 | 9 |
| Sorghum | 6 | 9 | 7 | 10 |
| Soybean | 9 | 10 | 9 | 10 |
| Sugar beet | 10 | 10 | 10 | 10 |
| Velvetleaf | 10 | 10 | 10 | 10 |
| Wheat | 6 | 9 | 6 | 6 |
| Wild buckwheat | 10 | 10 | 10 | 10 |
| Wild oat | 8 | 10 | 6 | 9 |
| PREEMERGENCE | | | | |
| Barley | 1 | 7 | 5 | 8 |
| Barnyardgrass | 9 | 9 | 10 | 10 |
| Bedstraw | 10 | 10 | 2 | 10 |
| Blackgrass | 6 | 8 | 2 | 5 |
| Cheatgrass | — | — | — | — |
| Chickweed | 1 | 10 | 5 | 10 |
| Cocklebur | 6 | 10 | 4 | 3 |
| Corn | 7 | 9 | 5 | 6 |
| Cotton | 3 | 10 | 5 | 10 |
| Crabgrass | 9 | 10 | 9 | 10 |
| Downy brome | 3 | 10 | 8 | 9 |
| Giant foxtail | 10 | 10 | 9 | 10 |
| Lambsquarter | 10 | 10 | 10 | 10 |
| Morningglory | 8 | 10 | 9 | 10 |
| Nutsedge | 0 | 2 | 3 | 0 |
| Rape | 9 | 10 | 10 | 10 |
| Rice | 3 | 6 | 7 | 6 |
| Sorghum | 6 | 8 | 3 | 8 |
| Soybean | 9 | 10 | 9 | 10 |
| Sugar beet | 9 | 10 | 10 | 10 |
| Velvetleaf | 10 | 10 | 10 | 10 |
| Wheat | 2 | 6 | 4 | 4 |
| Wild buckwheat | 6 | 10 | 9 | 9 |
| Wild oat | 9 | 9 | 6 | 9 |

| | COMPOUND | | | | | | | | | | | | | | | |
|---|---|---|---|---|---|---|---|---|---|---|---|---|---|---|---|---|
| Rate 200 g/ha | 3 | 4 | 5 | 6 | 8 | 10 | 11 | 12 | 14 | 17 | 18 | 19 | 20 | 21 | 22 | 24 | 25 |
| POSTEMERGENCE | | | | | | | | | | | | | | | | | |
| Barley | 4 | 5 | 4 | 4 | 2 | 3 | 4 | 6 | 5 | 3 | 5 | 3 | 5 | 2 | 7 | 3 | 4 |
| Barnyardgrass | 4 | 9 | 5 | 2 | 4 | 9 | 9 | 6 | 8 | 6 | 10 | 2 | 6 | 2 | 7 | 2 | 2 |
| Bedstraw | 6 | 10 | 8 | 7 | 6 | 8 | 10 | 9 | 9 | 9 | 10 | 6 | 10 | 7 | 9 | 5 | 6 |
| Blackgrass | 3 | 5 | 3 | 3 | 3 | 5 | 4 | 5 | 5 | 3 | 4 | 2 | 3 | 2 | 3 | 3 | 4 |
| Cheatgrass | — | — | — | — | — | — | — | — | — | — | — | 1 | 3 | — | — | — | — |
| Chickweed | 4 | 9 | 5 | 3 | 2 | 6 | 6 | 6 | 7 | 3 | 7 | 3 | 3 | 2 | 8 | 2 | 5 |

TABLE A-continued

| | | | | | | | | | | | | | | | | |
|---|---|---|---|---|---|---|---|---|---|---|---|---|---|---|---|---|
| Cocklebur | 3 | 9 | 7 | 6 | 7 | 8 | 10 | 8 | 9 | 10 | 10 | 8 | 8 | 5 | 9 | 9 | 8 |
| Corn | 2 | 6 | 4 | 3 | 2 | 4 | 8 | 2 | 4 | 6 | 8 | 7 | 3 | 2 | 3 | 2 | 2 |
| Cotton | 9 | 10 | 10 | 10 | 10 | 10 | 10 | 10 | 10 | 10 | 10 | 10 | 10 | 10 | 10 | 10 | 10 |
| Crabgrass | 6 | 6 | 3 | 3 | 3 | 7 | 5 | 2 | 4 | 4 | 8 | 6 | 5 | 2 | 2 | 2 | 3 |
| Downy brome | 4 | 5 | 4 | 4 | 3 | 4 | 5 | 5 | 3 | 4 | 5 | — | — | 2 | 4 | 2 | 3 |
| Giant foxtail | 4 | 7 | 4 | 3 | 4 | 8 | 7 | 4 | 5 | 4 | 5 | 4 | 6 | 2 | 3 | 2 | 3 |
| Lambsquarter | 8 | 9 | 10 | 8 | 9 | 10 | 9 | 9 | 9 | 9 | 9 | 8 | 7 | 5 | 9 | 9 | 9 |
| Morningglory | 4 | 10 | 8 | 9 | 9 | 8 | 10 | 9 | 9 | 9 | 10 | 7 | 8 | 8 | 10 | 6 | 9 |
| Nutsedge | 1 | 5 | 2 | 1 | 1 | 3 | — | 2 | 6 | — | — | — | — | 1 | — | 1 | 2 |
| Rape | 6 | 10 | 6 | 6 | 4 | 8 | 10 | 8 | 10 | 10 | 10 | 5 | 8 | 4 | 10 | 3 | 9 |
| Rice | 4 | 10 | 5 | 5 | 5 | 9 | 7 | 7 | 8 | 7 | 7 | 7 | 5 | 4 | 6 | 5 | 3 |
| Sorghum | 3 | 8 | 5 | 3 | 3 | 8 | 5 | 3 | 5 | 8 | 7 | 6 | 5 | 3 | 4 | 3 | 3 |
| Soybean | 6 | 8 | 8 | 6 | 8 | 8 | 5 | 9 | 7 | 6 | 9 | 9 | 9 | 6 | 7 | 7 | 5 |
| Sugar beet | 8 | 10 | 10 | 9 | 10 | 10 | 10 | 10 | 10 | 9 | 10 | 6 | 9 | 9 | 10 | 10 | 9 |
| Velvetleaf | 4 | 10 | 10 | 8 | 10 | 10 | 10 | 10 | 10 | 10 | 10 | 10 | 10 | 9 | 10 | 9 | 10 |
| Wheat | 5 | 6 | 4 | 4 | 3 | 4 | 4 | 7 | 5 | 3 | 5 | 2 | 3 | 1 | 6 | 3 | 4 |
| Wild buckwheat | 8 | 10 | 10 | 9 | 8 | 10 | 10 | 10 | 10 | 10 | 10 | 6 | 10 | 3 | 10 | 9 | 10 |
| Wild oat | 4 | 5 | 3 | 3 | 1 | 3 | 3 | 7 | 3 | 5 | 5 | 3 | 4 | 0 | 5 | 3 | 2 |

| | COMPOUND | | | | | | | | | | | | | | | |
|---|---|---|---|---|---|---|---|---|---|---|---|---|---|---|---|---|
| Rate 200 g/ha | 26 | 29 | 30 | 31 | 33 | 34 | 35 | 36 | 41 | 42 | 43 | 44 | 45 | 46 | 47 | 49 |

POSTEMERGENCE

| | | | | | | | | | | | | | | | | |
|---|---|---|---|---|---|---|---|---|---|---|---|---|---|---|---|---|
| Barley | 4 | 5 | 4 | 2 | 3 | 4 | 6 | 5 | 3 | 5 | 3 | 5 | 2 | 7 | 3 | 4 |
| Barnyardgrass | 1 | 7 | 2 | 6 | 7 | 10 | 8 | 9 | 10 | 10 | 9 | 3 | 3 | 2 | 10 | 2 |
| Bedstraw | 4 | 9 | 4 | 9 | 10 | 10 | 9 | 8 | 9 | 10 | 10 | 6 | 7 | 6 | 10 | 2 |
| Blackgrass | 3 | 5 | 3 | 3 | 4 | 3 | 3 | 6 | 9 | 10 | 8 | 3 | 3 | 3 | 6 | 2 |
| Cheatgrass | — | — | — | — | — | — | — | — | — | — | — | — | — | — | — | — |
| Chickweed | 1 | 7 | 3 | 3 | 6 | 9 | 6 | 9 | 10 | 10 | 9 | 6 | 4 | 1 | 9 | 0 |
| Cocklebur | 7 | 10 | 8 | 9 | 10 | 10 | 9 | 9 | 9 | 10 | 10 | 5 | 8 | 6 | 10 | 3 |
| Corn | 3 | 4 | 3 | 3 | 3 | 3 | 3 | 5 | 10 | 10 | 8 | 2 | 2 | 2 | 8 | 1 |
| Cotton | 10 | 10 | 9 | 10 | 10 | 10 | 10 | 10 | 10 | 10 | 10 | 10 | 10 | 10 | 10 | 5 |
| Crabgrass | 2 | 6 | 3 | 3 | 6 | 7 | 5 | 6 | 10 | 9 | 8 | 3 | 4 | 3 | 9 | 2 |
| Downy brome | 1 | 6 | 2 | 3 | 3 | 4 | 3 | 7 | 9 | 10 | 6 | 4 | 2 | 2 | 5 | 2 |
| Giant foxtail | 2 | 6 | 3 | 3 | 5 | 7 | 6 | 8 | 9 | 9 | 9 | 3 | 3 | 3 | 9 | 2 |
| Lambsquarter | 9 | 10 | 9 | 10 | 10 | 10 | 9 | 9 | 10 | 10 | 10 | 8 | 10 | 8 | 10 | 7 |
| Morningglory | 10 | 10 | 8 | 10 | 10 | 10 | 10 | 10 | 10 | 10 | 10 | 10 | 10 | 6 | 10 | 8 |
| Nutsedge | 1 | 5 | 2 | 5 | 4 | 4 | 6 | 8 | 9 | 9 | 7 | 2 | 4 | 6 | 5 | 0 |
| Rape | 5 | 10 | 3 | 10 | 10 | 10 | 10 | 10 | 10 | 10 | 10 | 9 | 10 | 3 | 10 | 4 |
| Rice | 3 | 6 | 4 | 4 | 7 | 7 | 6 | 7 | 10 | 10 | 9 | 4 | 3 | 4 | 10 | 3 |
| Sorghum | 3 | 6 | 3 | 3 | 7 | 9 | 5 | 7 | 10 | 10 | 9 | 2 | 3 | 3 | 9 | 2 |
| Soybean | 6 | 9 | 4 | 8 | 4 | 9 | 9 | 9 | 9 | 10 | 9 | 8 | 8 | 7 | 10 | 5 |
| Sugar beet | 10 | 10 | 8 | 10 | 10 | 10 | 10 | 10 | 10 | 10 | 10 | 8 | 7 | 6 | 10 | 7 |
| Velvetleaf | 10 | 10 | 8 | 10 | 10 | 10 | 10 | 10 | 10 | 10 | 10 | 10 | 6 | 9 | 10 | 7 |
| Wheat | 4 | 5 | 3 | 3 | 3 | 5 | 5 | 4 | 10 | 9 | 8 | 3 | 2 | 2 | 7 | 3 |
| Wild buckwheat | 9 | 10 | 10 | 10 | 10 | 10 | 10 | 10 | 10 | 10 | 10 | 4 | 10 | 5 | 10 | 3 |
| Wild oat | 2 | 5 | 3 | 2 | 4 | 7 | 4 | 6 | 9 | 10 | 9 | 4 | 2 | 2 | 8 | 2 |

| | COMPOUND | | | | | | | | | | | | | | | |
|---|---|---|---|---|---|---|---|---|---|---|---|---|---|---|---|---|
| Rate 200 g/ha | 3 | 4 | 5 | 6 | 8 | 10 | 11 | 12 | 14 | 17 | 18 | 19 | 20 | 21 | 22 | 24 | 25 |

PREEMERGENCE

| | | | | | | | | | | | | | | | | |
|---|---|---|---|---|---|---|---|---|---|---|---|---|---|---|---|---|
| Barley | 1 | 2 | 0 | 0 | 0 | 1 | 0 | 3 | 0 | 0 | 0 | 0 | 0 | 0 | 0 | 0 | 0 |
| Barnyardgrass | 2 | 8 | 2 | 2 | 0 | 7 | 2 | 8 | 4 | 0 | 2 | 0 | 0 | 0 | 4 | 0 | 0 |
| Bedstraw | 0 | 7 | 7 | 4 | 0 | 8 | 9 | 6 | 10 | 7 | 10 | 0 | 0 | 0 | 0 | 0 | 0 |
| Blackgrass | 1 | 3 | 0 | 0 | 1 | 2 | 2 | 6 | 1 | 2 | 2 | 0 | 0 | 0 | 3 | 0 | 0 |
| Cheatgrass | — | — | — | — | — | — | — | — | — | — | — | 0 | 0 | — | — | — | — |
| Chickweed | 0 | 5 | 0 | 0 | 1 | 7 | 0 | 0 | 6 | 2 | 4 | 0 | 0 | 0 | 6 | 0 | 0 |
| Cocklebur | 0 | 0 | 0 | 0 | 5 | 2 | 7 | 2 | 7 | 0 | 2 | 3 | 0 | 0 | 0 | 0 | 0 |
| Corn | 1 | 2 | 0 | 0 | 2 | 4 | 0 | 3 | 3 | 0 | 0 | 0 | 0 | 0 | 0 | 0 | 0 |
| Cotton | 0 | 0 | 2 | 0 | 0 | 0 | 9 | 9 | 3 | 0 | 3 | 0 | 0 | 0 | 0 | 0 | 0 |
| Crabgrass | 4 | 8 | 8 | 3 | 8 | 8 | 3 | 8 | 5 | 0 | 2 | 0 | 2 | 0 | 6 | 1 | 0 |
| Downy brome | 1 | 3 | 3 | 0 | 2 | 1 | 2 | 6 | 2 | 2 | 2 | — | — | 0 | 4 | 0 | 0 |
| Giant foxtail | 2 | 10 | 3 | 3 | 5 | 9 | 3 | 7 | 5 | 0 | 2 | 0 | 0 | 0 | 7 | 0 | 0 |
| Lambsquarter | 9 | 9 | 10 | 10 | 10 | 10 | 9 | 9 | 10 | 9 | 9 | 5 | 0 | 0 | 10 | 10 | 9 |
| Morningglory | 2 | 8 | 0 | 0 | 5 | 4 | 10 | 6 | 10 | 0 | 8 | 6 | 2 | 0 | 3 | 0 | 0 |
| Nutsedge | 0 | 0 | 0 | 0 | 0 | 0 | — | 1 | — | 0 | 0 | 0 | 0 | 0 | 0 | — | 0 |
| Rape | 2 | 10 | 2 | 0 | 2 | 8 | 10 | 10 | 10 | 10 | 10 | 0 | 0 | 0 | 6 | 0 | 0 |
| Rice | 0 | 4 | 0 | 0 | 0 | 2 | 2 | 3 | 3 | 3 | 2 | 0 | 0 | 0 | 0 | 0 | 0 |
| Sorghum | 2 | 2 | 0 | 0 | 0 | 0 | 2 | 1 | 3 | 0 | 0 | 0 | 0 | 0 | 0 | 0 | 0 |
| Soybean | 0 | 4 | 0 | 0 | 3 | 3 | 0 | 4 | 0 | 0 | 0 | 0 | 0 | 0 | 1 | 0 | 0 |
| Sugar beet | 4 | 10 | 9 | 8 | 8 | 9 | 10 | 10 | 10 | 9 | 9 | — | 0 | 0 | 6 | 0 | 0 |
| Velvetleaf | 6 | 9 | 9 | 4 | 3 | 10 | 9 | 10 | 10 | 10 | 10 | 8 | 3 | 0 | 9 | 0 | 0 |
| Wheat | 0 | 3 | 0 | 0 | 0 | 2 | 0 | 4 | 2 | 0 | 0 | 0 | 0 | 0 | 3 | 0 | 0 |

TABLE A-continued

| | | | | | | | | | | | | | | | | |
|---|---|---|---|---|---|---|---|---|---|---|---|---|---|---|---|---|
| Wild buckwheat | 0 | 6 | 0 | 0 | 0 | 0 | 0 | 1 | 1 | 2 | 0 | 0 | 0 | 0 | 1 | 0 | 0 |
| Wild oat | 0 | 5 | 2 | 0 | 1 | 2 | 2 | 6 | 3 | 2 | 0 | 1 | 0 | 0 | 3 | 0 | 0 |

COMPOUND

| Rate 200 g/ha | 26 | 29 | 30 | 31 | 33 | 34 | 35 | 36 | 41 | 42 | 43 | 44 | 45 | 46 | 47 | 49 |
|---|---|---|---|---|---|---|---|---|---|---|---|---|---|---|---|---|

PREEMERGENCE

| | | | | | | | | | | | | | | | | |
|---|---|---|---|---|---|---|---|---|---|---|---|---|---|---|---|---|
| Barley | 0 | 3 | 0 | 2 | 1 | 0 | 0 | 1 | 3 | 6 | 3 | 0 | 0 | 0 | 6 | 0 |
| Barnyardgrass | 0 | 9 | 0 | 4 | 5 | 3 | 8 | 9 | 9 | 9 | 7 | 9 | 0 | 0 | 10 | 0 |
| Bedstraw | 0 | 5 | 0 | 0 | 10 | 9 | 10 | 10 | 10 | 10 | 10 | 8 | 5 | 0 | 10 | 0 |
| Blackgrass | 0 | 3 | 2 | 2 | 3 | 2 | 3 | 3 | 5 | 10 | 9 | 0 | 2 | 0 | 7 | 0 |
| Cheatgrass | — | — | — | — | — | — | — | — | — | — | — | — | — | — | — | — |
| Chickweed | 0 | 8 | 0 | 0 | 8 | 8 | 2 | 9 | 10 | 10 | 10 | 5 | 0 | 0 | 10 | 0 |
| Cocklebur | 0 | 7 | 6 | 2 | 5 | 6 | 5 | 8 | 10 | 10 | 9 | 0 | 2 | 0 | 9 | 1 |
| Corn | 0 | 3 | 0 | 0 | 3 | 3 | 1 | 1 | 9 | 9 | 9 | 0 | 2 | 0 | 7 | 0 |
| Cotton | 0 | 9 | 0 | 5 | 8 | 9 | 10 | 8 | 10 | 10 | 9 | 2 | 0 | 0 | 9 | 0 |
| Crabgrass | 0 | 8 | 0 | 2 | 3 | 9 | 9 | 9 | 10 | 10 | 10 | 2 | 5 | 0 | 9 | 0 |
| Downy brome | 0 | 7 | 3 | 3 | 6 | 4 | 6 | 8 | 9 | 10 | 9 | 0 | 0 | 0 | 10 | 0 |
| Giant foxtail | 0 | 10 | 0 | 7 | 5 | 10 | 9 | 10 | 9 | 10 | 10 | 8 | 3 | 0 | 9 | 0 |
| Lambsquarter | 7 | 10 | 3 | 9 | 10 | 10 | 10 | 10 | 10 | 10 | 10 | 10 | 9 | 4 | 10 | 0 |
| Morningglory | 0 | 10 | 0 | 6 | 10 | 10 | 10 | 2 | 10 | 10 | 10 | 0 | 3 | 0 | 10 | 2 |
| Nutsedge | 0 | 4 | 0 | 3 | 2 | 0 | — | — | 9 | 6 | 7 | — | 3 | 0 | 5 | 0 |
| Rape | 0 | 10 | 0 | 7 | 9 | 9 | 9 | 8 | 10 | 10 | 10 | 3 | 9 | 0 | 10 | 3 |
| Rice | 0 | 0 | 0 | 0 | 3 | 3 | 2 | 3 | 10 | 10 | 9 | 3 | 4 | 0 | 9 | 0 |
| Sorghum | 0 | 0 | 0 | 0 | 3 | 3 | 2 | 3 | 8 | 8 | 6 | 1 | 0 | 0 | 9 | 0 |
| Soybean | 0 | 2 | 0 | 3 | 10 | 9 | 4 | 6 | 8 | 10 | 7 | 0 | 2 | 0 | 8 | 0 |
| Sugar beet | 0 | 9 | 0 | 5 | 10 | 9 | 9 | 10 | 10 | 10 | 10 | 7 | 7 | 0 | 10 | 0 |
| Velvetleaf | 0 | 10 | 3 | 10 | 10 | 10 | 10 | 10 | 10 | 10 | 10 | 8 | 10 | 0 | 10 | 2 |
| Wheat | 0 | 4 | 0 | 3 | 1 | 0 | 1 | 2 | 6 | 9 | 9 | 0 | 0 | 0 | 6 | 0 |
| Wild buckwheat | 0 | 9 | 0 | 0 | 8 | 5 | 2 | 4 | 10 | 10 | 10 | 0 | 0 | 0 | 10 | 0 |
| Wild oat | 0 | 7 | 2 | 2 | 6 | 7 | 2 | 6 | 9 | 10 | 9 | 0 | 2 | 0 | 9 | 0 |

COMPOUND

| Rate 100 g/ha | 1 | 2 | 7 | 9 | 13 | 15 | 16 | 23 | 28 | 37 | 38 | 48 | 50 | 51 | 52 |
|---|---|---|---|---|---|---|---|---|---|---|---|---|---|---|---|

POSTEMERGENCE

| | | | | | | | | | | | | | | | |
|---|---|---|---|---|---|---|---|---|---|---|---|---|---|---|---|
| Barley | 3 | 8 | 1 | 4 | 7 | 4 | 3 | 6 | 4 | 5 | 5 | 0 | 9 | 4 | 4 |
| Barnyardgrass | 9 | 10 | 2 | 3 | 9 | 4 | 8 | 9 | 5 | 10 | 8 | 5 | 8 | 6 | 7 |
| Bedstraw | 8 | 9 | 3 | 8 | 8 | 8 | 9 | 9 | 10 | 10 | 9 | 6 | 8 | 4 | 6 |
| Blackgrass | 4 | 9 | 1 | 2 | 6 | 3 | 3 | 5 | 4 | 6 | 5 | 0 | 7 | 5 | 4 |
| Cheatgrass | — | — | — | — | — | — | — | — | — | — | — | — | — | — | — |
| Chickweed | 4 | 10 | 1 | 2 | 6 | 4 | 3 | 9 | 2 | 8 | 5 | 2 | 9 | 3 | 3 |
| Cocklebur | 7 | 10 | 1 | 7 | 8 | 9 | 7 | 10 | 9 | 9 | 10 | 6 | 9 | 3 | 10 |
| Corn | 4 | 8 | 2 | 2 | 3 | 2 | 6 | 3 | 2 | 5 | 3 | 2 | 1 | 1 | 3 |
| Cotton | 10 | 10 | 9 | 9 | 10 | 10 | 10 | 10 | 10 | 10 | 10 | 9 | 9 | 7 | 9 |
| Crabgrass | 5 | 9 | 2 | 6 | 7 | 5 | 4 | 8 | 2 | 6 | 7 | 2 | 4 | 3 | 3 |
| Downy brome | 3 | 7 | 0 | 2 | 7 | 3 | 2 | 4 | 2 | 6 | 4 | 0 | 8 | 3 | 5 |
| Giant foxtail | 5 | 9 | 1 | 4 | 8 | 3 | 7 | 9 | 3 | 8 | 7 | 2 | 5 | 2 | 6 |
| Lambsquarter | 10 | 10 | 3 | 9 | 8 | 9 | 6 | 10 | 8 | 10 | 9 | 4 | 9 | 9 | 9 |
| Morningglory | 9 | 10 | 8 | 9 | 9 | 9 | 10 | 10 | 10 | 10 | 10 | 9 | 10 | 10 | 10 |
| Nutsedge | 1 | 4 | 1 | 4 | 8 | — | 5 | 1 | 2 | 2 | 2 | 0 | 2 | — | 2 |
| Rape | 6 | 10 | 2 | 9 | 9 | 10 | 10 | 10 | 9 | 10 | 10 | 2 | 10 | 10 | 10 |
| Rice | 6 | 10 | 1 | 6 | 9 | 6 | 5 | 8 | 4 | 4 | 6 | 0 | 8 | 3 | 7 |
| Sorghum | 4 | 9 | 2 | 3 | 6 | 4 | 5 | 9 | 5 | 4 | 4 | 2 | 4 | 3 | 3 |
| Soybean | 9 | 9 | 3 | 7 | 8 | 8 | 3 | 9 | 8 | 8 | 8 | 4 | 2 | 6 | 8 |
| Sugar beet | 9 | 10 | 3 | 9 | 10 | 9 | 8 | 9 | 10 | 10 | 10 | 8 | 10 | 10 | 9 |
| Velvetleaf | 9 | 10 | 8 | 9 | 10 | 10 | 10 | 10 | 10 | 10 | 10 | 1 | 9 | 8 | 10 |
| Wheat | 4 | 9 | 1 | 3 | 7 | 5 | 3 | 5 | 4 | 5 | 4 | 2 | 9 | 5 | 9 |
| Wild buckwheat | 10 | 10 | 3 | 9 | 8 | 10 | 6 | 10 | 9 | 10 | 9 | 3 | 10 | 10 | 10 |
| Wild oat | 4 | 8 | 0 | 2 | 8 | 4 | 2 | 7 | 2 | 5 | 4 | 0 | 6 | 3 | 4 |

PREEMERGENCE

| | | | | | | | | | | | | | | | |
|---|---|---|---|---|---|---|---|---|---|---|---|---|---|---|---|
| Barley | 1 | 4 | 0 | 3 | 7 | 0 | 0 | 3 | 0 | 0 | 0 | 0 | 3 | 0 | 3 |
| Barnyardgrass | 7 | 9 | 0 | 7 | 10 | 0 | 0 | 9 | 0 | 2 | 0 | 0 | 0 | 0 | 2 |
| Bedstraw | 1 | 10 | 2 | 2 | 7 | 8 | 0 | 10 | 0 | 7 | 0 | 0 | 3 | 0 | 3 |
| Blackgrass | 2 | 7 | 0 | 0 | 6 | 2 | 0 | 4 | 0 | 5 | 5 | 1 | 0 | 0 | 3 |
| Cheatgrass | — | — | — | — | — | — | — | — | — | — | — | — | — | — | — |
| Chickweed | 1 | 10 | 0 | 0 | 6 | 3 | 0 | 8 | 0 | 0 | 0 | 0 | 2 | 0 | 0 |
| Cocklebur | 2 | 10 | 0 | 3 | 9 | 0 | 0 | — | 0 | 2 | 0 | 3 | 0 | 0 | 6 |
| Corn | 1 | 6 | 0 | 3 | 7 | 0 | 0 | 1 | 0 | 1 | 0 | 0 | 0 | 0 | 0 |
| Cotton | 2 | 9 | 0 | 0 | 4 | 0 | 0 | 8 | 0 | 1 | 0 | 0 | 0 | 0 | 0 |
| Crabgrass | 9 | 10 | 0 | 6 | 8 | 0 | 0 | 9 | 1 | 7 | 1 | 0 | 0 | 0 | 9 |
| Downy brome | 1 | 7 | 0 | 2 | 6 | 3 | 0 | 9 | 2 | 3 | 3 | 1 | 3 | 2 | 2 |
| Giant foxtail | 9 | 10 | 0 | 10 | 9 | 0 | 0 | 9 | 3 | 9 | 4 | 0 | 0 | 0 | 0 |
| Lambsquarter | 10 | 10 | 0 | 8 | 9 | 9 | 0 | 10 | 10 | 10 | 9 | 7 | 9 | 6 | 6 |
| Morningglory | 0 | 10 | 0 | 3 | 10 | 0 | 4 | 10 | 0 | 6 | 2 | 0 | 10 | 0 | 10 |

TABLE A-continued

| | | | | | | | | | | | | | | | |
|---|---|---|---|---|---|---|---|---|---|---|---|---|---|---|---|
| Nutsedge | 0 | — | 0 | 0 | 2 | 0 | — | 0 | 0 | 0 | 0 | 3 | 0 | 0 | 0 |
| Rape | 8 | 10 | 0 | 10 | 10 | 6 | 1 | 10 | 2 | 8 | 3 | 0 | 7 | 3 | 0 |
| Rice | 1 | 3 | 0 | 4 | 8 | 0 | 0 | 3 | 0 | 2 | 0 | 0 | 0 | 0 | 2 |
| Sorghum | 3 | 4 | 0 | 0 | 7 | 0 | 0 | 2 | 0 | 0 | 0 | 0 | 0 | 0 | 0 |
| Soybean | 4 | 9 | 0 | 3 | 6 | 0 | 0 | 0 | 0 | 1 | 0 | 0 | 0 | 0 | 0 |
| Sugar beet | 6 | 10 | 3 | 7 | 10 | 9 | 2 | 8 | 3 | 10 | 6 | 3 | 8 | 7 | 5 |
| Velvetleaf | 10 | 10 | 0 | 10 | 10 | 0 | 0 | 10 | 0 | 10 | 10 | 0 | 0 | 0 | 0 |
| Wheat | 0 | 5 | 0 | 3 | 8 | 2 | 0 | 6 | 0 | 0 | 3 | 0 | 3 | 0 | 3 |
| Wild buckwheat | 4 | 10 | 0 | 1 | 3 | 4 | 0 | 8 | 4 | 2 | 0 | 0 | 2 | 0 | 0 |
| Wild oat | 4 | 8 | 0 | 3 | 7 | 3 | 0 | 6 | 0 | 7 | 3 | 0 | 3 | 2 | 5 |

| | COMPOUND | | | | | | | | | | | | | | |
|---|---|---|---|---|---|---|---|---|---|---|---|---|---|---|---|
| Rate 50 g/ha | 3 | 4 | 5 | 6 | 8 | 10 | 11 | 12 | 14 | 17 | 18 | 19 | 20 | 21 | 22 | 24 |

POSTEMERGENCE

| | | | | | | | | | | | | | | | |
|---|---|---|---|---|---|---|---|---|---|---|---|---|---|---|---|
| Barley | 3 | 5 | 3 | 3 | 2 | 3 | 3 | 5 | 5 | 3 | 5 | 2 | 3 | 1 | 5 | 3 |
| Barnyardgrass | 2 | 6 | 3 | 2 | 3 | 3 | 7 | 2 | 2 | 3 | 7 | 2 | 3 | 2 | 5 | 2 |
| Bedstraw | 3 | 9 | 7 | 6 | 4 | 7 | 10 | 7 | 7 | 9 | 10 | 4 | 7 | 4 | 9 | 5 |
| Blackgrass | 2 | 4 | 3 | 2 | 2 | 2 | 2 | 4 | 3 | 3 | 3 | 1 | 2 | 3 | 2 | 3 |
| Cheatgrass | — | — | — | — | — | — | — | — | — | — | 0 | 1 | — | — | — |
| Chickweed | 2 | 7 | 3 | 1 | 2 | 4 | 1 | 6 | 5 | 3 | 3 | 3 | 2 | 1 | 6 | 2 |
| Cocklebur | 1 | 7 | 4 | 4 | 7 | 7 | 8 | 7 | 8 | 6 | 8 | 6 | 8 | 1 | 9 | 7 |
| Corn | 2 | 6 | 3 | 3 | 2 | 2 | 5 | 3 | 2 | 6 | 9 | 4 | 2 | 1 | 1 | 2 |
| Cotton | 3 | 10 | 9 | 9 | 9 | 10 | 10 | 9 | 9 | 10 | 10 | 10 | 10 | 10 | 10 | 10 |
| Crabgrass | 3 | 4 | 2 | 2 | 3 | 4 | 3 | 3 | 3 | 2 | 6 | 5 | 4 | 1 | 1 | 2 |
| Downy brome | 1 | 4 | 3 | 3 | 2 | 3 | 3 | 3 | 2 | 3 | 3 | — | — | 2 | 3 | 2 |
| Giant foxtail | 2 | 4 | 3 | 3 | 3 | 4 | 5 | 2 | 3 | 3 | 5 | 3 | 4 | 1 | 2 | 2 |
| Lambsquarter | 6 | 8 | 9 | 5 | 9 | 8 | 9 | 8 | 9 | 8 | 8 | 4 | 6 | 3 | 9 | 4 |
| Morningglory | 3 | 9 | 7 | 6 | 7 | 8 | 9 | 9 | 8 | 9 | 10 | 5 | 9 | 5 | 10 | 6 |
| Nutsedge | 0 | 4 | 1 | 1 | 0 | 1 | 4 | 1 | 3 | — | — | — | — | — | 0 | 1 |
| Rape | 5 | 10 | 5 | 5 | 3 | 6 | 9 | 6 | 9 | 8 | 10 | 3 | 7 | 5 | 8 | 3 |
| Rice | 3 | 7 | 5 | 5 | 3 | 6 | 5 | 5 | 6 | 6 | 6 | 6 | 4 | 4 | 5 | 3 |
| Sorghum | 3 | 3 | 3 | 3 | 2 | 3 | 5 | 2 | 2 | 6 | 6 | 3 | 3 | 2 | 3 | 2 |
| Soybean | 5 | 8 | 4 | 5 | 3 | 8 | 3 | 8 | 7 | 4 | 8 | 6 | 7 | 3 | 6 | — |
| Sugar beet | 6 | 10 | 10 | 8 | 9 | 10 | 10 | 9 | 10 | 10 | 10 | 4 | 6 | 2 | 8 | 8 |
| Velvetleaf | 3 | 10 | 9 | 8 | 4 | 9 | 10 | 6 | 10 | 10 | 10 | 10 | 10 | 1 | 10 | 8 |
| Wheat | 2 | 5 | 3 | 2 | 2 | 3 | 2 | 36 | 4 | 4 | 4 | 1 | 2 | 1 | 3 | 3 |
| Wild buckwheat | 4 | 10 | 7 | 5 | 7 | 9 | 9 | 8 | 7 | 9 | 10 | 6 | 9 | 1 | 9 | 6 |
| Wild oat | 3 | 4 | 4 | 2 | 1 | 2 | 2 | 3 | 4 | 4 | 4 | 2 | 1 | 0 | 2 | 3 |

| | COMPOUND | | | | | | | | | | | | | | |
|---|---|---|---|---|---|---|---|---|---|---|---|---|---|---|---|
| Rate 50 g/ha | 25 | 26 | 29 | 30 | 31 | 33 | 34 | 35 | 36 | 42 | 43 | 44 | 45 | 46 | 47 | 49 |

POSTEMERGENCE

| | | | | | | | | | | | | | | | |
|---|---|---|---|---|---|---|---|---|---|---|---|---|---|---|---|
| Barley | 3 | 2 | 5 | 2 | 3 | 5 | 5 | 3 | 4 | 7 | 5 | 2 | 1 | 2 | 4 | 0 |
| Barnyardgrass | 2 | 1 | 5 | 2 | 1 | 4 | 8 | 4 | 7 | 9 | 9 | 1 | 2 | 2 | 9 | 1 |
| Bedstraw | 4 | 4 | 8 | 2 | 5 | 10 | 9 | 8 | 9 | 10 | 9 | 4 | 6 | 3 | 10 | 2 |
| Blackgrass | 3 | 2 | 4 | 2 | 3 | 3 | 3 | 3 | 2 | 9 | 6 | 1 | 2 | 0 | 2 | 1 |
| Cheatgrass | — | — | — | — | — | — | — | — | — | — | — | — | — | — | — | — |
| Chickweed | 1 | 1 | 8 | 1 | 2 | 6 | 7 | 3 | 9 | 10 | 8 | 5 | 5 | 1 | 8 | 0 |
| Cocklebur | 7 | 6 | 10 | 6 | 8 | 10 | 9 | 8 | 8 | 9 | 9 | 3 | 7 | 6 | 9 | 3 |
| Corn | 2 | 2 | 2 | 2 | 2 | 3 | 3 | 3 | 2 | 9 | 7 | 2 | 2 | 1 | 5 | 0 |
| Cotton | 10 | 10 | 10 | 7 | 9 | 10 | 10 | 10 | 10 | 10 | 10 | 10 | 5 | 10 | 10 | 5 |
| Crabgrass | 2 | 2 | 4 | 3 | 3 | 6 | 6 | 3 | 5 | 9 | 7 | 2 | 3 | 2 | 7 | 1 |
| Downy brome | 2 | 1 | 3 | 2 | 2 | 2 | 3 | 3 | 3 | 8 | 4 | 1 | 1 | 0 | 3 | 0 |
| Giant foxtail | 3 | 2 | 4 | 3 | 3 | 4 | 5 | 3 | 6 | 9 | 8 | 2 | 2 | 2 | 8 | 1 |
| Lambsquarter | 8 | 7 | 10 | 8 | 9 | 10 | 10 | 7 | 9 | 10 | 8 | 8 | 8 | 4 | 10 | 4 |
| Morningglory | 7 | 7 | 10 | 6 | 10 | 9 | 10 | 10 | 10 | 10 | 10 | 9 | 8 | 2 | 10 | 3 |
| Nutsedge | 1 | 1 | 3 | 2 | 3 | — | — | 2 | 2 | 6 | 5 | — | 2 | 0 | 2 | 0 |
| Rape | 6 | 5 | 10 | 1 | 8 | 10 | 10 | 9 | 9 | 10 | 9 | 6 | 8 | 2 | 10 | 2 |
| Rice | 3 | 3 | 5 | 3 | 4 | 5 | 6 | 5 | 6 | 10 | 9 | 3 | 3 | 2 | 8 | 2 |
| Sorghum | 3 | 3 | 4 | 2 | 3 | 46 | 6 | 4 | 5 | 9 | 9 | 2 | 2 | 2 | 7 | 2 |
| Soybean | 3 | 3 | 8 | 3 | 5 | 4 | 9 | 8 | 9 | 9 | 5 | 8 | 8 | 5 | 9 | 3 |
| Sugar beet | 10 | 8 | 10 | 3 | 10 | 10 | 9 | 9 | 10 | 10 | 10 | 8 | 7 | 2 | 10 | 4 |
| Velvetleaf | 10 | 10 | 10 | 5 | 5 | 10 | 10 | 10 | 10 | 10 | 10 | 4 | 2 | 3 | 10 | 1 |
| Wheat | 3 | 2 | 5 | 2 | 3 | 3 | 4 | 4 | 3 | 7 | 6 | 1 | 0 | 1 | 5 | 1 |
| Wild buckwheat | 9 | 8 | 10 | 6 | 9 | 10 | 10 | 9 | 10 | 10 | 10 | 3 | 9 | 3 | 10 | 2 |
| Wild oat | 1 | 1 | 5 | 2 | 2 | 4 | 5 | 4 | 4 | 9 | 6 | 2 | 2 | 1 | 5 | 0 |

TABLE A-continued

| | COMPOUND | | | | | | | | | | | | | | | |
|---|---|---|---|---|---|---|---|---|---|---|---|---|---|---|---|---|
| Rate 50 g/ha | 3 | 4 | 5 | 6 | 8 | 10 | 11 | 12 | 14 | 17 | 18 | 19 | 20 | 21 | 22 | 24 |
| | PREEMERGENCE | | | | | | | | | | | | | | | |
| Barley | 0 | 0 | 0 | 0 | 0 | 0 | 0 | 0 | 0 | 0 | 0 | 0 | 0 | 0 | 0 | 0 |
| Barnyardgrass | 2 | 5 | 0 | 0 | 0 | 0 | 0 | 0 | 0 | 0 | 0 | 0 | 0 | 0 | 2 | 0 |
| Bedstraw | 0 | 3 | 4 | 4 | — | 3 | 2 | 5 | 4 | 0 | 9 | 0 | 0 | 0 | 0 | 0 |
| Blackgrass | 1 | 0 | 0 | 0 | 0 | 1 | 0 | 0 | 1 | 0 | 0 | 0 | 0 | 0 | 0 | 0 |
| Chestgrass | — | — | — | — | — | — | — | — | — | — | 0 | 0 | — | — | — | |
| Chickweed | 0 | 2 | 0 | 0 | 0 | 2 | 0 | 0 | 3 | 2 | 4 | 0 | 0 | 0 | 3 | 0 |
| Cocklebur | 0 | 0 | 0 | 0 | 3 | 0 | 0 | 0 | 3 | 0 | 0 | 0 | 0 | 0 | 0 | 0 |
| Corn | 0 | 0 | 0 | 0 | 0 | 2 | 0 | 2 | 0 | 0 | 0 | 0 | 0 | 0 | 0 | 0 |
| Cotton | 0 | 0 | 0 | 0 | 0 | 0 | 3 | 4 | 0 | 0 | 0 | 0 | 0 | 0 | 0 | 0 |
| Crabgrass | 2 | 0 | 3 | 3 | 2 | 6 | 0 | 1 | 2 | 0 | 2 | 0 | 0 | 0 | 3 | 0 |
| Downy brome | 0 | 2 | 0 | 0 | 0 | 1 | 0 | 0 | 0 | 0 | 2 | — | — | 0 | 0 | 0 |
| Giant foxtail | 0 | 3 | 0 | 0 | 0 | 6 | 0 | 0 | 2 | 0 | 0 | 0 | 0 | 0 | 2 | 0 |
| Lambsquarter | 2 | 6 | 9 | 9 | 8 | 10 | 8 | 7 | 10 | 8 | 6 | 3 | 0 | 0 | 10 | 0 |
| Morningglory | 0 | 9 | 0 | 0 | 0 | 4 | 10 | 3 | 4 | 0 | 4 | 3 | 0 | 0 | 0 | 0 |
| Nutsedge | 0 | 0 | 0 | 0 | 0 | 0 | 0 | 0 | — | 0 | 0 | 0 | 0 | 0 | 0 | 0 |
| Rape | 0 | 10 | 0 | 0 | 0 | 0 | 9 | 3 | 10 | 9 | 6 | 0 | 0 | 0 | 2 | 0 |
| Rice | 0 | 2 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 |
| Soybean | 0 | 0 | 0 | 0 | 3 | 0 | 0 | 0 | 0 | 0 | 0 | 0 | 0 | 0 | 0 | 0 |
| Sugar beet | 0 | 9 | 6 | 4 | 7 | 8 | 10 | 4 | 9 | 9 | 9 | 0 | 0 | 0 | 6 | 0 |
| Velvetleaf | 3 | 2 | 0 | 0 | 0 | 9 | 2 | 9 | 10 | 0 | 3 | 4 | 0 | 0 | 2 | 0 |
| Wheat | 0 | 2 | 0 | 0 | 0 | 0 | 0 | 0 | 1 | 0 | 0 | 0 | 0 | 0 | 0 | 0 |
| Wild buckwheat | 0 | 3 | 0 | 0 | 0 | 0 | 0 | 0 | 0 | 0 | 0 | 0 | 0 | 0 | 0 | 0 |
| Wild oat | 0 | 0 | 0 | 0 | 0 | 1 | 0 | 0 | 0 | 0 | 2 | 0 | 0 | 0 | 0 | 0 |

| | COMPOUND | | | | | | | | | | | | | | | |
|---|---|---|---|---|---|---|---|---|---|---|---|---|---|---|---|---|
| Rate 50 g/ha | 25 | 26 | 29 | 30 | 31 | 33 | 34 | 35 | 36 | 42 | 43 | 44 | 45 | 46 | 47 | 494 |
| | PREEMERGENCE | | | | | | | | | | | | | | | |
| Barley | 0 | 0 | 1 | 0 | 0 | 0 | 0 | — | 0 | 5 | 3 | 0 | 0 | 0 | 2 | 0 |
| Barnyardgrass | 0 | 0 | 3 | 0 | 0 | 0 | 0 | 2 | 2 | 9 | 8 | 0 | 0 | 0 | 9 | 0 |
| Bedstraw | 0 | 0 | 5 | 0 | 0 | 6 | 9 | 9 | 9 | 10 | 10 | 0 | 0 | 0 | 10 | 0 |
| Blackgrass | 0 | 0 | 3 | 0 | 0 | 0 | 2 | 0 | 1 | 9 | 7 | 0 | 2 | 0 | 3 | 0 |
| Chestgrass | — | — | — | — | — | — | — | — | — | — | — | — | — | — | — | — |
| Chickweed | 0 | 0 | 6 | 0 | 0 | 2 | 3 | 0 | 0 | 10 | 9 | 0 | 0 | 0 | 9 | 0 |
| Cocklebur | 0 | 0 | 3 | 0 | — | 3 | 3 | 0 | 3 | 10 | 5 | 0 | 0 | 0 | 6 | 0 |
| Corn | 0 | 0 | 2 | 0 | 0 | 2 | 2 | 0 | 0 | 9 | 5 | 0 | 0 | 0 | 8 | 0 |
| Cotton | 0 | 0 | 4 | 0 | 0 | 4 | 0 | 0 | 0 | 10 | 6 | 0 | 0 | 0 | 8 | 0 |
| Crabgrass | 0 | 0 | 2 | 0 | 0 | 3 | 8 | 5 | 8 | 10 | 8 | 0 | 0 | 0 | 8 | 0 |
| Downy brome | 0 | 0 | 3 | 0 | 2 | 3 | 5 | 2 | 2 | 8 | 5 | 0 | 1 | 0 | 2 | 0 |
| Giant foxtail | 0 | 0 | 8 | 0 | 0 | 3 | 8 | 7 | 9 | 9 | 8 | 0 | 0 | 0 | 7 | 0 |
| Lambsquarter | 0 | 0 | 10 | 0 | 9 | 9 | 10 | 10 | 10 | 10 | 10 | 10 | 9 | 0 | 10 | 0 |
| Morningglory | 0 | 0 | 5 | 0 | 0 | 0 | 6 | 0 | 0 | 10 | 10 | 0 | 2 | 0 | 10 | 0 |
| Nutsedge | 0 | 0 | 0 | 0 | 0 | 0 | 0 | 0 | — | 6 | — | — | 5 | 0 | 3 | 0 |
| Rape | 0 | 0 | 7 | 0 | 0 | 2 | 9 | 5 | 6 | 10 | 10 | 0 | 2 | 0 | 10 | 0 |
| Rice | 0 | 0 | 0 | 0 | 0 | 2 | 2 | 0 | 2 | 9 | 7 | 0 | 0 | 0 | 8 | 0 |
| Sorghum | 0 | 0 | 0 | 0 | 0 | 2 | 0 | 0 | 0 | 6 | 5 | 0 | 0 | 0 | 8 | 0 |
| Soybean | 0 | 0 | 0 | 0 | 0 | 5 | 3 | 2 | 0 | 7 | 6 | 0 | 0 | 0 | 6 | 0 |
| Sugar beet | 0 | 0 | 6 | 0 | 0 | 6 | 7 | 8 | 9 | 10 | 10 | 0 | 7 | 0 | 10 | 0 |
| Velvetleaf | 0 | 0 | 3 | 0 | 0 | 0 | 0 | 1 | 1 | 6 | 6 | 0 | 0 | 0 | 3 | 0 |
| Wheat | 0 | 0 | 3 | 0 | 0 | 0 | 0 | 1 | 1 | 6 | 6 | 0 | 0 | 0 | 3 | 0 |
| Wild buckwheat | 0 | 0 | 6 | 0 | 0 | 0 | 0 | 0 | 0 | 10 | 5 | 0 | 0 | 0 | 2 | 0 |
| Wild oat | 0 | 0 | 4 | 0 | 0 | 5 | 6 | 1 | 3 | 9 | 9 | 0 | 0 | 0 | 6 | 0 |

| | COMPOUND | | | | | | | | | | |
|---|---|---|---|---|---|---|---|---|---|---|---|
| Rate 20 g/ha | 7 | 13 | 15 | 16 | 28 | 37 | 38 | 48 | 50 | 51 | 52 |
| | POSTEMERGENCE | | | | | | | | | | |
| Barley | 0 | 4 | 3 | 2 | 3 | 4 | 4 | 0 | 5 | 3 | 5 |
| Barnyardgrass | 1 | 8 | 3 | 5 | 5 | 6 | 7 | 1 | 6 | 4 | 5 |
| Bedstraw | 3 | 8 | 6 | 5 | 4 | 9 | 8 | 2 | 7 | 2 | 3 |
| Blackgrass | 1 | 3 | 2 | 2 | 3 | 4 | 4 | 0 | 5 | 2 | 3 |
| Chestgrass | — | — | — | — | — | — | — | — | — | — | — |
| Chickweed | 0 | 4 | 3 | 2 | 2 | 6 | 5 | 0 | 7 | 2 | 3 |
| Cocklebur | 0 | 7 | 8 | 6 | 6 | 7 | 10 | 2 | 4 | 2 | 4 |
| Corn | 1 | 2 | 2 | 2 | 2 | 4 | 2 | 1 | 1 | 1 | 2 |
| Cotton | 7 | 10 | 10 | 10 | 9 | 10 | 10 | 9 | 7 | 3 | 9 |
| Crabgrass | 0 | 4 | 3 | 3 | 2 | 6 | 6 | 2 | 2 | 1 | 3 |
| Downy brome | 0 | 2 | 3 | 2 | 2 | 5 | 4 | 0 | 7 | 2 | 4 |

TABLE A-continued

| | | | | | | | | | | | |
|---|---|---|---|---|---|---|---|---|---|---|---|
| Giant foxtail | 0 | 4 | 3 | 3 | 3 | 6 | 5 | 3 | 2 | 1 | 2 |
| Lambsquarter | 4 | 6 | 8 | 4 | 6 | 8 | 8 | 2 | 8 | 8 | 8 |
| Morningglory | 2 | 9 | 10 | 6 | 9 | 10 | 10 | 7 | 9 | 10 | 10 |
| Nutsedge | 0 | 4 | — | 4 | — | 0 | 0 | 0 | 0 | 0 | 1 |
| Rape | 1 | 6 | 8 | 8 | 5 | 9 | 8 | 2 | 8 | 6 | 10 |
| Rice | 1 | 8 | 5 | 3 | 3 | 3 | 3 | 3 | 3 | 2 | 3 |
| Sorghum | 2 | 3 | 3 | 3 | 3 | 4 | 3 | 3 | 3 | 2 | 3 |
| Soybean | 1 | 7 | 7 | 3 | 4 | 8 | 8 | 3 | 2 | 5 | 4 |
| Sugar beet | 2 | 10 | 10 | 5 | 6 | 8 | 9 | 3 | 8 | 9 | 8 |
| Velvetleaf | 1 | 10 | 10 | 5 | 8 | 10 | 10 | 1 | 4 | 2 | 4 |
| Wheat | 0 | 5 | 3 | 2 | 4 | 4 | 3 | 0 | 7 | 3 | 6 |
| Wild buckwheat | 2 | 7 | 8 | 6 | 8 | 9 | 10 | 3 | 10 | 7 | 4 |
| Wild oat | 0 | 3 | 3 | 1 | 1 | 3 | 3 | 0 | 4 | 3 | 3 |
| PREEMERGENCE | | | | | | | | | | | |
| Barley | 0 | 1 | 3 | 0 | 0 | 2 | 0 | 0 | 0 | 0 | 0 |
| Barnyardgrass | 0 | 8 | 0 | 0 | 0 | 0 | 0 | 0 | 0 | 0 | 0 |
| Bedstraw | 0 | 3 | 8 | — | 0 | 0 | 0 | 0 | 0 | 0 | 0 |
| Blackgrass | 0 | 3 | 2 | 0 | 0 | 2 | 2 | 0 | 0 | 0 | 0 |
| Cheatgrass | — | — | — | — | — | — | — | — | — | — | — |
| Chickweed | 0 | 2 | — | 0 | 0 | 0 | 0 | 0 | 0 | 0 | 0 |
| Cocklebur | 0 | 5 | 0 | 0 | 0 | 0 | 0 | 0 | 0 | 0 | 0 |
| Corn | 0 | 4 | 0 | 0 | 0 | 0 | 0 | 0 | 0 | 0 | 0 |
| Cotton | 0 | 4 | 0 | 0 | 0 | 0 | 0 | 0 | 0 | 0 | 0 |
| Crabgrass | 0 | 3 | 0 | 0 | 0 | 2 | 0 | 0 | 0 | 0 | 0 |
| Downy brome | 0 | 4 | — | 0 | 0 | 2 | 2 | 0 | 2 | 0 | 0 |
| Giant foxtail | 0 | 7 | 0 | 0 | 0 | 3 | 0 | 0 | 0 | 0 | 0 |
| Lambsquarter | 0 | 9 | — | 0 | 0 | 7 | 9 | — | 2 | 0 | 0 |
| Morningglory | 0 | 3 | 0 | 0 | 0 | 0 | 0 | 0 | 6 | 0 | 0 |
| Nutsedge | 0 | 0 | 0 | — | 0 | 0 | 0 | — | 0 | 0 | 0 |
| Rape | 0 | 8 | 2 | 0 | 0 | 2 | 0 | 0 | 3 | 0 | 0 |
| Rice | 0 | 7 | 0 | 0 | 0 | 0 | 0 | 0 | 0 | 0 | 0 |
| Sorghum | 0 | 1 | 0 | 0 | 0 | 0 | 0 | 0 | 0 | 0 | 0 |
| Soybean | 0 | 5 | 0 | 0 | 0 | 0 | 0 | 0 | 0 | 0 | 0 |
| Sugar beet | 0 | 9 | 3 | 0 | 0 | 2 | 0 | 0 | 3 | 0 | 0 |
| Velvetleaf | 0 | 9 | 0 | 0 | 0 | 8 | 4 | 0 | 0 | 0 | 0 |
| Wheat | 0 | 3 | 2 | 0 | 0 | 2 | 0 | 0 | 0 | 0 | 1 |
| Wild buckwheat | 0 | 0 | 3 | 0 | 0 | 0 | 0 | 0 | 0 | 0 | 0 |
| Wild oat | 0 | 3 | 2 | 0 | 0 | 3 | 0 | 0 | 0 | 0 | 1 |

TEST B

Seeds of barnyardgrass (*Echinochloa crus-galli*), cocklebur (*Xanthium pensylvanicum*), crabgrass (*Digitaria sanguinalis*), downy brome (*Bromus tectorum*), giant foxtail (*Setaria faberii*), morningglory (*Ipomoea* spp.), sorghum (*Sorghum bicolor*), velvetleaf (*Abutilon theophrasti*), and wild oat (*Avena fatua*) were planted into a sandy loam soil and treated preemergence or by soil drench, with test chemicals formulated in a non-phytotoxic solvent mixture which includes a surfactant. At the same time, these crop and weed species were also treated postemergence or sprayed to runoff, with test chemicals formulated in the same manner. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table B, are based on a 0 to 10 scale where 0 is no effect and 10 is complete control. A dash (-) response means no test results.

| | COMPOUND | |
|---|---|---|
| Rate 2000 g/ha | 27 | 49 |
| SOIL DRENCH | | |
| Barnyardgrass | 9 | 8 |
| Cocklebur | 7 | 5 |
| Crabgrass | 9 | 3 |
| Downy brome | 7 | 2 |
| Giant foxtail | 10 | 5 |
| Morningglory | 10 | 10 |
| Sorghum | 5 | 2 |
| Velvetleaf | 10 | 7 |
| Wild oats | 5 | 0 |

| | COMPOUND | |
|---|---|---|
| Rate 1000 g/ha | 27 | 49 |
| SPRAYED TO RUNOFF | | |
| Barnyardgrass | 7 | 4 |
| Cocklebur | 10 | 10 |
| Crabgrass | 5 | 4 |
| Downy brome | 8 | 7 |
| Giant foxtail | 7 | 6 |
| Morningglory | 10 | 10 |
| Sorghum | 6 | 3 |
| Velvetleaf | 10 | 10 |
| Wild oats | 3 | 4 |

TEST C

The compounds evaluated in this test were formulated in a non-phytotoxic solvent mixture which includes a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyard 2 (*Echinochloa crus-galli*) and watergrass 2 (*Echinocloa oryzicola*) grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings summarized in Table C, were recorded on a 0 to 100 scale where 0 is no effect and 100 is complete control. A dash (-) response means no test result.

TABLE C

| Rate 250 g/ha | COMPOUND 4 | Rate 250 g/ha | COMPOUND 4 |
|---|---|---|---|
| POSTEMERGENCE | | PREEMERGENCE | |
| Barley Igri | 35 | Barley Igri | 10 |
| Barnyard 2 | 85 | Barnyardgrass | 90 |
| Barnyardgrass | 95 | Bedstraw | 75 |
| Bedstraw | 85 | Blackgrass | 40 |
| Blackgrass | 55 | Chickweed | 80 |
| Chickweed | 95 | Cocklebur | 40 |
| Cocklebur | 100 | Corn | 20 |
| Corn | 35 | Cotton | 30 |
| Cotton | 100 | Crabgrass | 70 |
| Crabgrass | 40 | Downy Brome | 0 |
| Downy Brome | 35 | Giant foxtail | 100 |
| Duck salad | 0 | Italn. Rygrass | 0 |
| Giant foxtail | 85 | Johnsongrass | 20 |
| Italn. Rygrass | 65 | Lambsquarter | 90 |
| Johnsongrass | 90 | Morningglory | 70 |
| Lambsquarter | 70 | Rape | 100 |
| Morningglory | 100 | Redroot Pigweed | 100 |
| Rape | 100 | Soybean | 50 |
| Redroot Pigweed | 100 | Speedwell | 100 |
| Rice | 95 | Sugar beet | 100 |
| Soybean | 100 | Velvetleaf | 100 |
| Speedwell | — | Wheat | 0 |
| Sugar beet | — | Wild buckwheat | 100 |
| Umbrella sedge | 15 | Wild oat | 30 |
| Velvetleaf | 100 | | |
| Watergrass 2 | 85 | | |
| Wheat | 30 | | |
| Wild buckwheat | 100 | | |
| Wild oat | 40 | | |

| | COMPOUND | | | | |
|---|---|---|---|---|---|
| Rate 125 g/ha | 1 | 4 | 9 | 23 | 41 |
| POSTEMERGENCE | | | | | |
| Barley Igri | — | 35 | 30 | 55 | 95 |
| Barnyard 2 | 20 | 40 | 10 | 100 | 70 |
| Barnyardgrass | — | 40 | 80 | 95 | 95 |
| Bedstraw | — | 70 | 0 | 100 | 100 |
| Blackgrass | — | 50 | 0 | 80 | 65 |
| Chickweed | — | 95 | 10 | 100 | 100 |
| Cocklebur | — | 85 | 35 | 100 | 100 |
| Corn | — | 30 | 25 | 35 | 90 |
| Cotton | — | 100 | 95 | 100 | 100 |
| Crabgrass | — | 35 | 25 | 85 | 95 |
| Downy Brome | — | 35 | 20 | 85 | 100 |
| Duck salad | 0 | 0 | 0 | 50 | 0 |
| Giant foxtail | — | 65 | 65 | 100 | 100 |
| Italn. Rygrass | — | 30 | 20 | 95 | 100 |
| Johnsongrass | — | 80 | 30 | 90 | 100 |
| Lambsquarter | — | 70 | 90 | 100 | 100 |

TABLE C-continued

|  |  |  |  |  |  |
|---|---|---|---|---|---|
| Morningglory | — | 100 | 90 | 100 | 100 |
| Rape | — | 100 | 100 | 100 | 100 |
| Redroot Pigweed | — | 100 | 75 | 100 | 100 |
| Rice | 45 | 70 | 20 | 100 | 95 |
| Soybean | — | 75 | 50 | 100 | 80 |
| Speedwell | — | — | 100 | 100 | — |
| Sugar beet | — | 100 | 40 | 100 | 100 |
| Umbrella sedge | 0 | 0 | 0 | 50 | 0 |
| Velvetleaf | — | 100 | 100 | 100 | 100 |
| Watergrass 2 | 15 | 80 | 0 | 100 | 95 |
| Wheat | — | 30 | 20 | 50 | 100 |
| Wild buckwheat | — | 100 | 85 | 100 | 100 |
| Wild oat | — | 30 | 20 | 75 | 95 |
| PREEMERGENCE |  |  |  |  |  |
| Barley Igri | 0 | 10 | 50 | 70 | 80 |
| Barnyardgrass | 90 | 25 | 35 | 100 | 95 |
| Bedstraw | 100 | 15 | 10 | 100 | 100 |
| Blackgrass | 55 | 30 | 0 | 80 | 95 |
| Chickweed | 20 | 60 | 20 | 100 | 100 |
| Cocklebur | 0 | 30 | 25 | 85 | 100 |
| Corn | 10 | 0 | 20 | 50 | 55 |
| Cotton | 10 | 25 | 35 | 100 | 100 |
| Crabgrass | 90 | 50 | 70 | 100 | 100 |
| Downy Brome | 0 | 0 | 10 | 80 | 60 |
| Giant foxtail | 95 | 100 | 95 | 100 | 100 |
| Italn. Rygrass | 60 | 0 | 20 | 90 | 100 |
| Johnsongrass | 90 | 15 | 20 | 95 | 100 |
| Lambsquarter | 100 | 85 | 70 | 100 | 100 |
| Morningglory | 20 | — | 60 | 100 | 100 |
| Rape | 10 | 100 | 100 | 100 | 100 |
| Redroot Pigweed | 100 | 100 | 80 | 100 | 100 |
| Soybean | 30 | 30 | 10 | 40 | 95 |
| Speedwell | 100 | 100 | 90 | 100 | 100 |
| Sugar beet | 100 | 100 | 45 | 100 | 100 |
| Velvetleaf | 100 | 100 | 100 | 100 | 100 |
| Wheat | 0 | 0 | 10 | 65 | 100 |
| Wild buckwheat | 10 | 90 | 30 | 100 | 100 |
| Wild oat | 20 | 10 | 50 | 65 | 90 |

| Rate 62 g/ha | COMPOUND |  |  |  |  |  |  |  |  |  |  |  |  |  |
|---|---|---|---|---|---|---|---|---|---|---|---|---|---|---|
|  | 1 | 2 | 4 | 9 | 18 | 22 | 23 | 29 | 33 | 34 | 35 | 36 | 41 | 43 |
| POSTEMERGENCE |  |  |  |  |  |  |  |  |  |  |  |  |  |  |
| Barley Igri | — | 55 | 30 | 20 | 35 | 35 | 55 | 75 | 45 | 65 | 55 | 50 | 95 | 65 |
| Barnyard 2 | 10 | 95 | 20 | 0 | 20 | 85 | 100 | 85 | 85 | 95 | 40 | 70 | 60 | 10 |
| Barnyardgrass | — | 80 | 10 | 40 | 35 | 30 | 95 | 80 | 60 | 80 | 70 | 90 | 65 | 85 |
| Bedstraw | — | 100 | 65 | 0 | 25 | 20 | 100 | 100 | 95 | 100 | 95 | 95 | 100 | 85 |
| Blackgrass | — | 80 | 40 | 0 | 10 | 45 | 70 | 40 | 50 | 75 | 40 | 65 | 35 | 65 |
| Chickweed | — | 100 | 75 | 10 | 50 | 95 | 90 | 100 | 95 | 95 | 90 | 100 | 100 | 100 |
| Cocklebur | — | 100 | 80 | 25 | 70 | 60 | 100 | 100 | 100 | 100 | 90 | 90 | 85 | — |
| Corn | — | 65 | 30 | 25 | 55 | 30 | 30 | 35 | 40 | 25 | 30 | 30 | 65 | 80 |
| Cotton | — | 100 | 100 | 90 | 100 | 100 | 100 | 100 | 100 | 100 | 100 | 100 | 100 | 100 |
| Crabgrass | — | 100 | 30 | 10 | 35 | 20 | 85 | 50 | 30 | 50 | 50 | 80 | 65 | 60 |
| Downy Brome | — | 65 | 30 | 0 | 45 | 0 | 75 | 45 | 65 | 80 | 60 | 85 | 100 | 40 |
| Duck salad | 0 | 0 | 0 | 0 | 0 | 25 | 0 | 0 | 30 | 35 | 0 | 0 | 0 | 0 |
| Giant foxtail | — | 100 | 30 | 30 | 65 | 60 | 95 | 60 | 50 | 60 | 75 | 65 | 85 | 70 |
| Italn. Rygrass | — | 90 | 30 | 0 | 0 | 0 | 90 | 65 | 75 | 70 | 50 | 75 | 95 | 90 |
| Johnsongrass | — | 100 | 60 | 20 | 90 | 50 | 90 | 60 | 50 | 80 | 50 | 70 | 95 | 95 |
| Lambsquarter | — | 100 | 65 | 90 | 100 | 90 | 100 | 100 | 100 | 100 | 100 | 100 | 70 | 100 |
| Morningglory | — | 100 | 100 | 70 | 100 | 95 | 100 | 100 | 100 | 100 | 95 | 100 | 100 | 100 |
| Rape | — | 100 | 100 | 95 | 100 | 35 | 100 | 100 | 100 | 100 | 100 | 100 | 100 | 100 |
| Redroot Pigweed | — | 100 | 100 | 70 | 100 | 100 | 100 | 100 | 100 | 100 | 100 | 100 | 100 | 100 |
| Rice | 40 | 95 | 60 | 20 | 25 | 25 | 95 | 50 | 70 | 75 | 35 | 55 | 90 | 10 |
| Soybean | — | 100 | 75 | 50 | 65 | 90 | 100 | 90 | 60 | 100 | 90 | 90 | 80 | 100 |
| Speedwell | — | 100 | — | 95 | 100 | 40 | 100 | 100 | 100 | 100 | 100 | 100 | — | 100 |
| Sugar beet | — | 100 | 100 | 40 | 100 | 95 | 100 | — | 100 | 100 | 100 | 100 | 100 | 100 |
| Umbrella sedge | 0 | 50 | — | 0 | 0 | 0 | 0 | 0 | 25 | 30 | 0 | 0 | 0 | 0 |
| Velvetleaf | — | 100 | 100 | 100 | 100 | 100 | 100 | 100 | 100 | 100 | 100 | 100 | 100 | 100 |
| Watergrass 2 | 10 | 90 | 25 | 0 | 30 | 30 | 100 | 45 | 85 | 65 | 30 | 65 | 85 | 10 |
| Wheat | — | 60 | 30 | 15 | 35 | 35 | 50 | 65 | 65 | 65 | 65 | 70 | 95 | 80 |
| Wild buckwheat | — | 100 | 95 | 80 | 85 | 95 | 100 | 100 | 100 | 100 | 100 | 100 | 100 | 100 |
| Wild oat | — | 70 | 30 | 10 | 30 | 0 | 70 | 80 | 50 | 70 | 60 | 65 | 95 | 80 |
| PREEMERGENCE |  |  |  |  |  |  |  |  |  |  |  |  |  |  |
| Barley Igri | 0 | 10 | 0 | 30 | 0 | 0 | 30 | 0 | 0 | 25 | 0 | 35 | 80 | 70 |
| Barnyardgrass | 65 | 80 | 25 | 20 | 0 | 10 | 100 | 10 | 0 | 20 | 0 | 80 | 90 | 95 |

TABLE C-continued

| | | | | | | | | | | | | | | |
|---|---|---|---|---|---|---|---|---|---|---|---|---|---|---|
| Bedstraw | 0 | 100 | 10 | 10 | 0 | 0 | 100 | 0 | 25 | 100 | 90 | 0 | 100 | 100 |
| Blackgrass | 10 | 80 | 25 | 0 | 10 | 0 | 70 | 35 | 0 | 0 | 0 | 30 | 85 | 70 |
| Chickweed | 20 | 95 | 30 | — | 0 | 0 | 100 | 85 | 0 | 95 | 10 | 90 | 100 | 100 |
| Cocklebur | 0 | 70 | 20 | 10 | 0 | 0 | 60 | 20 | 20 | 35 | 0 | 0 | 60 | 100 |
| Corn | 0 | 65 | 0 | 0 | 0 | 10 | 50 | 10 | 10 | 0 | 0 | 0 | 55 | 60 |
| Cotton | 0 | 100 | 20 | 0 | 0 | 25 | 60 | 0 | 30 | 70 | 0 | 0 | 90 | 90 |
| Crabgrass | 30 | 100 | 20 | 70 | 0 | 55 | 100 | 75 | 10 | 20 | 10 | 50 | 95 | 85 |
| Downy Brome | 0 | 55 | 0 | 10 | 10 | 10 | 10 | 0 | 0 | 0 | 0 | 25 | 60 | 60 |
| Giant foxtail | 50 | 100 | 80 | 55 | 0 | 10 | 95 | 60 | 0 | 100 | 30 | 90 | 95 | 100 |
| Ital. Ryegrass | 10 | 85 | 0 | 15 | 0 | 0 | 80 | 0 | 10 | 30 | 30 | 70 | 95 | 90 |
| Johnsongrass | 20 | 90 | 0 | 10 | 0 | 20 | 85 | 0 | 0 | 20 | 0 | 20 | 95 | 95 |
| Lambsquarter | 100 | 100 | 50 | 50 | 20 | 0 | 100 | 100 | 100 | 100 | 100 | 100 | 100 | 100 |
| Morningglory | 10 | 100 | 60 | — | 0 | 50 | 75 | 10 | 80 | 60 | 20 | 70 | 100 | 80 |
| Rape | 0 | 100 | 60 | 90 | 0 | 0 | 60 | 0 | 10 | 25 | 10 | 10 | 100 | 100 |
| Redroot Pigweed | 100 | 100 | 100 | 35 | 100 | 100 | 100 | 100 | 100 | 100 | 100 | 100 | 100 | 100 |
| Soybean | 30 | 100 | 0 | 0 | 0 | 40 | 35 | 0 | 25 | 20 | 0 | 0 | 15 | 0 |
| Speedwell | 100 | 100 | 30 | 85 | 85 | 20 | 100 | 95 | 95 | 95 | 100 | 95 | 100 | 100 |
| Sugar beet | 20 | 100 | 100 | 35 | 25 | 10 | 100 | 10 | 35 | 100 | 10 | 100 | 100 | 100 |
| Velvetleaf | 100 | 100 | 50 | 85 | 20 | 60 | 100 | 100 | 100 | 100 | 80 | 100 | 100 | 100 |
| Wheat | — | 55 | 0 | 0 | 0 | 0 | 20 | 20 | 0 | 0 | 0 | 40 | 80 | 90 |
| Wild buckwheat | 0 | 100 | 70 | 10 | 0 | 0 | 100 | 35 | 30 | 100 | 25 | 50 | 75 | 90 |
| Wild oat | 20 | 65 | 0 | 30 | 15 | 0 | 60 | 0 | 0 | 25 | 50 | 65 | 80 | 80 |

| | COMPOUND | | | | | | | | | | | | | |
|---|---|---|---|---|---|---|---|---|---|---|---|---|---|---|
| Rate 31 g/ha | 1 | 2 | 4 | 9 | 18 | 22 | 23 | 29 | 33 | 34 | 35 | 36 | 41 | 42 | 43 |

POSTEMERGENCE

| | | | | | | | | | | | | | | | |
|---|---|---|---|---|---|---|---|---|---|---|---|---|---|---|---|
| Barley Igri | — | 50 | 30 | 20 | 30 | 30 | 55 | 60 | 45 | 60 | 55 | 50 | 75 | 65 | 50 |
| Barnyard 2 | 10 | 90 | 0 | 0 | 15 | 25 | 85 | 65 | 70 | 75 | 30 | 35 | 25 | 100 | 0 |
| Barnyardgrass | — | 75 | 10 | 0 | 30 | 20 | 90 | 60 | 60 | 70 | 50 | 30 | 0 | 95 | 85 |
| Bedstraw | — | 100 | 65 | 0 | 25 | 10 | 100 | 95 | 90 | 100 | 90 | 90 | 100 | 100 | 75 |
| Blackgrass | — | 70 | 35 | 0 | 10 | 0 | 60 | 40 | 50 | 75 | 40 | 65 | 35 | 75 | 65 |
| Chickweed | — | 95 | 75 | 0 | 50 | 50 | 95 | 75 | 95 | 95 | 80 | 95 | 100 | 95 | 70 |
| Cocklebur | — | 100 | 60 | 10 | 60 | 60 | 100 | 90 | 90 | 90 | 70 | 90 | — | 100 | 90 |
| Corn | — | 65 | 30 | 10 | 35 | 20 | 25 | 30 | 30 | 25 | 30 | 25 | 35 | 85 | 65 |
| Cotton | — | 100 | 100 | 90 | 100 | 100 | 100 | 100 | 100 | 100 | 100 | 100 | 100 | 100 | 100 |
| Crabgrass | — | 85 | 25 | 0 | 30 | 15 | 80 | 20 | — | 50 | 30 | 30 | 65 | 80 | 60 |
| Downy Brome | — | 60 | 30 | 0 | 0 | 0 | 60 | 30 | 55 | 75 | 60 | 70 | 35 | 65 | 25 |
| Duck salad | 0 | 0 | 0 | 0 | 0 | 10 | 0 | 0 | 0 | 20 | 0 | 0 | 0 | 0 | 0 |
| Giant foxtail | — | 95 | 30 | 0 | 50 | 30 | 90 | 50 | 50 | 50 | 35 | 35 | 75 | 90 | 70 |
| Ital. Ryegrass | — | 85 | 10 | 0 | 0 | 0 | 80 | 65 | 70 | 65 | 50 | 70 | 70 | 95 | 90 |
| Johnsongrass | — | 95 | 40 | 10 | 75 | 30 | 80 | 40 | 50 | 60 | 30 | 60 | 40 | 90 | 90 |
| Lambsquarter | — | 100 | 65 | 70 | 65 | 50 | 100 | 100 | 100 | 100 | 100 | 100 | 65 | 100 | 95 |
| Morningglory | — | 100 | 100 | 45 | 100 | 80 | 100 | 100 | 95 | 100 | — | 90 | 100 | 100 | 100 |
| Rape | — | 100 | 100 | 75 | 90 | 0 | 100 | 95 | 100 | 100 | 95 | 100 | 100 | 100 | 85 |
| Redroot Pigweed | — | 100 | 100 | 50 | — | 90 | 100 | 100 | 100 | 100 | 95 | 100 | 100 | 100 | 100 |
| Rice | 35 | 90 | 30 | 10 | 0 | 30 | 75 | 45 | 60 | 65 | 25 | 35 | 60 | 80 | 10 |
| Soybean | — | 95 | 75 | 25 | 55 | — | 90 | 60 | 50 | 100 | 80 | 80 | 80 | 90 | 70 |
| Speedwell | — | 100 | — | 95 | 100 | — | 100 | 100 | 100 | 100 | 90 | 100 | — | 100 | 100 |
| Sugar beet | — | 100 | 80 | 30 | 60 | 90 | 100 | 100 | 100 | 100 | 100 | 100 | 95 | 100 | 100 |
| Umbrella sedge | 0 | 50 | 0 | 0 | 0 | 0 | 0 | 0 | 20 | 0 | 0 | 0 | 0 | 0 | 0 |
| Velvetleaf | — | 100 | 100 | 100 | 100 | 100 | 100 | 100 | 100 | 100 | 100 | 100 | 100 | 100 | 100 |
| Watergrass 2 | 10 | 55 | 20 | 0 | 30 | 25 | 75 | 25 | 75 | 55 | 25 | 55 | 25 | 10 | 0 |
| Wheat | — | 50 | 30 | 15 | 35 | 35 | 40 | 50 | 50 | 45 | 45 | 55 | 65 | 85 | 70 |
| Wild buckwheat | — | 100 | 80 | 65 | 40 | 40 | 100 | 100 | 100 | 100 | 90 | 100 | 100 | 100 | 100 |
| Wild oat | — | 50 | 30 | 10 | 30 | 0 | 65 | 65 | 50 | 70 | 60 | 60 | 35 | 90 | 70 |

PREEMERGENCE

| | | | | | | | | | | | | | | | |
|---|---|---|---|---|---|---|---|---|---|---|---|---|---|---|---|
| Barley Igri | 0 | 0 | 0 | 10 | 0 | 0 | 30 | 0 | 0 | 0 | 0 | 10 | 70 | 75 | 50 |
| Barnyardgrass | — | 70 | 10 | 15 | 0 | 0 | 90 | 10 | 0 | 10 | 0 | 20 | 90 | 95 | 90 |
| Bedstraw | 0 | 100 | 0 | 10 | 0 | 0 | 90 | — | 25 | 95 | 10 | 0 | 100 | 100 | 100 |
| Blackgrass | 10 | 80 | 30 | 0 | 0 | 0 | 55 | 10 | 0 | 0 | 0 | 10 | 60 | 90 | 60 |
| Chickweed | 10 | 55 | 0 | 0 | 0 | 0 | 0 | 0 | 0 | 85 | 10 | 25 | 100 | 100 | 80 |
| Cocklebur | 0 | — | 0 | 0 | 0 | 0 | 50 | 0 | 0 | 20 | 0 | 0 | 45 | 100 | 20 |
| Corn | 0 | 35 | 0 | 0 | 0 | 0 | 20 | 0 | 0 | 0 | 0 | 0 | 55 | 60 | 50 |
| Cotton | — | 70 | 0 | 0 | 0 | 10 | 50 | 0 | 30 | — | 0 | 0 | 80 | 100 | 70 |
| Crabgrass | 0 | 95 | 0 | 0 | 0 | 10 | 90 | 20 | 0 | — | 0 | 40 | 95 | 80 | 50 |
| Downy Brome | 0 | 45 | 0 | 0 | 0 | 10 | 0 | 0 | 0 | 0 | 0 | 10 | 35 | 70 | 30 |
| Giant foxtail | 10 | 95 | 60 | — | 0 | 0 | 95 | 25 | 0 | 80 | 30 | 30 | 85 | 95 | 80 |
| Ital. Ryegrass | 0 | 85 | 0 | 0 | 0 | 0 | 60 | 0 | 0 | 10 | 30 | 55 | 90 | 90 | 85 |
| Johnsongrass | 20 | 85 | 0 | 10 | 0 | 10 | 75 | 0 | 0 | 10 | 0 | 20 | 95 | 90 | 80 |
| Lambsquarter | 100 | 100 | 20 | 50 | 10 | 0 | 100 | 100 | 100 | 100 | 100 | 95 | 100 | 100 | 100 |
| Morningglory | 0 | — | 40 | 30 | 0 | 40 | 65 | 10 | 40 | 30 | 10 | 50 | 90 | 75 | 80 |
| Rape | 0 | 95 | 0 | 20 | 0 | 0 | 25 | 0 | 0 | 0 | 10 | 0 | 100 | 100 | 85 |
| Redroot Pigweed | 100 | 100 | 100 | 0 | 90 | 60 | 100 | 95 | 100 | 100 | 100 | 80 | 100 | 100 | 100 |
| Soybean | 20 | 55 | 0 | 0 | 0 | 0 | 10 | 0 | 10 | 10 | 0 | 0 | 15 | 100 | 0 |
| Speedwell | 10 | 100 | 0 | 75 | 0 | — | 30 | 20 | 90 | — | 100 | — | 100 | 100 | 100 |

TABLE C-continued

| | | | | | | | | | | | | | | |
|---|---|---|---|---|---|---|---|---|---|---|---|---|---|---|
| Sugar beet | 20 | 100 | 30 | 25 | 0 | 0 | 95 | 0 | 30 | 85 | 0 | 0 | 100 | 100 | 100 |
| Velvetleaf | 100 | 100 | 0 | 70 | 10 | 20 | 100 | 90 | 80 | 100 | 30 | 80 | 100 | 100 | 100 |
| Wheat | 0 | 40 | 0 | 0 | 0 | 0 | 20 | 10 | 0 | 0 | 0 | 40 | 80 | 90 | 75 |
| Wild buckwheat | 0 | 80 | 10 | 0 | 0 | 0 | 100 | 0 | 30 | 10 | 0 | 30 | 70 | 100 | 90 |
| Wild oat | 20 | 65 | 0 | 10 | 10 | 0 | 45 | 0 | 0 | 25 | 35 | 50 | 70 | 90 | 80 |

| | COMPOUND | | | | | | | | | | | | | |
|---|---|---|---|---|---|---|---|---|---|---|---|---|---|---|
| Rate 16 g/ha | 1 | 2 | 9 | 18 | 22 | 23 | 29 | 33 | 34 | 35 | 36 | 41 | 42 | 43 |

POSTEMERGENCE

| | | | | | | | | | | | | | | |
|---|---|---|---|---|---|---|---|---|---|---|---|---|---|---|
| Barley Igri | — | 45 | 10 | 25 | 20 | 50 | 50 | 45 | 55 | 50 | 40 | 45 | 40 | 35 |
| Barnyard 2 | 10 | 60 | 0 | 0 | 0 | 55 | 30 | 45 | 40 | 20 | 30 | 20 | 100 | 0 |
| Barnyardgrass | — | 65 | 0 | 25 | 15 | 80 | 40 | 50 | 60 | 40 | 30 | 0 | 95 | 70 |
| Bedstraw | — | 100 | 0 | 25 | 10 | 95 | 75 | 60 | 100 | 70 | 75 | 95 | 100 | — |
| Blackgrass | — | 45 | 0 | 0 | 0 | 50 | 40 | 35 | 70 | 40 | 65 | 30 | 75 | 60 |
| Chickweed | — | 95 | 0 | 40 | 50 | 80 | 75 | 75 | 90 | 65 | 95 | 90 | 95 | 70 |
| Cocklebur | — | 90 | 0 | 50 | 50 | 90 | 80 | 90 | 90 | 60 | 70 | 50 | 100 | 85 |
| Corn | — | 50 | 10 | 20 | 20 | 25 | 25 | 25 | 25 | 30 | 25 | 35 | 65 | 60 |
| Cotton | — | 100 | 90 | 100 | 100 | 100 | 100 | 100 | 100 | 100 | 100 | 100 | 100 | 100 |
| Crabgrass | — | 75 | 0 | 20 | 10 | 55 | — | 20 | 30 | 20 | 20 | 45 | 70 | 30 |
| Downy Brome | — | 65 | 0 | 0 | 0 | 55 | 30 | 50 | 70 | 50 | 70 | 20 | 55 | 25 |
| Duck salad | 0 | 0 | 0 | 0 | 0 | 0 | 0 | 0 | 0 | 0 | 0 | 0 | 0 | 0 |
| Giant foxtail | — | 95 | 0 | 40 | 30 | 75 | 40 | 50 | 40 | 30 | 35 | 55 | 80 | 55 |
| Italn. Rygrass | — | 70 | 0 | 0 | 0 | 45 | 55 | 65 | 65 | 40 | 70 | 45 | 80 | 45 |
| Johnsongrass | — | 90 | 0 | 60 | 20 | 70 | 35 | 50 | 40 | 30 | 60 | 40 | 90 | 85 |
| Lambsquarter | — | 100 | 40 | 40 | 50 | 100 | 100 | 95 | 100 | 90 | 100 | 65 | 95 | 70 |
| Morningglory | — | 100 | 45 | 85 | 70 | 100 | 100 | 95 | 100 | 90 | 90 | 95 | 100 | 90 |
| Rape | — | 100 | 50 | 80 | 0 | 100 | 75 | 100 | 65 | 90 | 90 | 100 | 100 | 85 |
| Redroot Pigweed | — | 100 | 40 | 100 | 90 | 100 | 100 | 100 | 100 | 85 | 100 | 80 | 100 | — |
| Rice | 35 | 80 | 10 | 0 | 0 | 50 | 35 | 45 | 50 | 10 | 35 | 30 | 45 | 0 |
| Soybean | — | 90 | 20 | 50 | 50 | 85 | 60 | 50 | 95 | — | 70 | 80 | 80 | 70 |
| Speedwell | — | 100 | 0 | 100 | 40 | 100 | — | 100 | 100 | 70 | 95 | — | 100 | 100 |
| Sugar beet | — | 100 | 20 | 50 | 65 | 100 | 100 | 100 | 100 | 95 | 90 | 95 | 100 | 100 |
| Umbrella sedge | 0 | 0 | 0 | 0 | 0 | 0 | 0 | 20 | 0 | 0 | 0 | 0 | 0 | 0 |
| Velvetleaf | — | 100 | 95 | 100 | 100 | 100 | 100 | 95 | 100 | 100 | 100 | 100 | 100 | 100 |
| Watergrass 2 | 10 | 30 | 0 | 20 | 25 | 45 | 15 | 40 | 40 | 25 | 40 | 20 | 10 | 0 |
| Wheat | — | 35 | 10 | 30 | 35 | 35 | 35 | 45 | 40 | 40 | 45 | 45 | 50 | 30 |
| Wild buckwheat | — | 100 | 45 | 0 | 30 | 100 | 65 | 100 | 100 | 85 | 90 | 70 | 100 | 95 |
| Wild oat | — | 55 | 10 | 20 | 0 | 50 | 65 | 50 | 70 | 60 | 60 | 25 | 85 | 55 |

PREEMERGENCE

| | | | | | | | | | | | | | | |
|---|---|---|---|---|---|---|---|---|---|---|---|---|---|---|
| Barley Igri | 0 | 0 | 0 | 0 | 0 | 30 | 0 | 0 | 0 | 0 | 10 | 0 | 50 | 10 |
| Barnyardgrass | 15 | 90 | 10 | 0 | 0 | 85 | 0 | 0 | 0 | 0 | 0 | 70 | 95 | 30 |
| Bedstraw | 0 | 100 | 0 | 0 | 0 | 0 | 0 | 0 | 50 | 0 | 0 | 100 | 100 | 90 |
| Blackgrass | 0 | 55 | 0 | 0 | 0 | 45 | 10 | 0 | 0 | 0 | 0 | 20 | 80 | 50 |
| Chickweed | 0 | 25 | 0 | 0 | 0 | 100 | 0 | 0 | 10 | 0 | 0 | 95 | 95 | 35 |
| Cocklebur | 0 | 40 | 0 | 0 | 0 | 10 | 0 | 0 | 10 | 0 | 0 | 0 | 25 | 0 |
| Corn | 0 | 35 | 0 | 0 | 0 | 10 | 0 | 0 | 0 | 0 | 0 | 30 | 35 | 40 |
| Cotton | 0 | 35 | 0 | 0 | 0 | 30 | 0 | 20 | 30 | — | 0 | 35 | 90 | 30 |
| Crabgrass | — | 95 | 0 | 0 | 0 | 90 | 20 | 0 | 20 | 0 | 30 | 55 | 70 | 50 |
| Downy Brome | 0 | 40 | 0 | 0 | 0 | 0 | 0 | 0 | 0 | 0 | 10 | 10 | 30 | 10 |
| Giant foxtail | 0 | 95 | 10 | 0 | 0 | 70 | 10 | 0 | 40 | 0 | 0 | 65 | 95 | 80 |
| Italn. Rygrass | 0 | 75 | 0 | 0 | 0 | 30 | 0 | 0 | 0 | 20 | 40 | 70 | 70 | 45 |
| Johnsongrass | 0 | 85 | 0 | 0 | 0 | 60 | 0 | 0 | 0 | 0 | 0 | 55 | 30 | 60 |
| Lambsquarter | 100 | 100 | 30 | 0 | 0 | 100 | 100 | 65 | 100 | 90 | 95 | 100 | 100 | 100 |
| Morningglory | 0 | 95 | 15 | 0 | 20 | 45 | 0 | 20 | 30 | 0 | 30 | 35 | 65 | 40 |
| Rape | 0 | 100 | 15 | 0 | 0 | 0 | 0 | 0 | 0 | 0 | 0 | 100 | 90 | 30 |
| Redroot Pigweed | 90 | 100 | 0 | 80 | — | 100 | 50 | 85 | 85 | 10 | — | 100 | 100 | 100 |
| Soybean | 0 | 55 | 0 | — | 0 | 0 | 0 | 0 | 0 | 0 | 0 | 0 | 35 | 0 |
| Speedwell | — | 100 | 40 | 0 | 10 | 30 | 0 | 90 | 90 | 100 | 95 | 100 | 100 | 100 |
| Sugar beet | 0 | 100 | 10 | 0 | 0 | 60 | 0 | 10 | — | 0 | 0 | 100 | 100 | 65 |
| Velvetleaf | 30 | 100 | 15 | 0 | 10 | 100 | 20 | 70 | 90 | 10 | 20 | 100 | 85 | 30 |
| Wheat | 0 | 35 | 0 | 0 | 0 | 20 | 10 | 0 | 0 | 0 | 40 | 25 | 40 | 20 |
| Wild buckwheat | 0 | 70 | 0 | 0 | 0 | 70 | 0 | 0 | 10 | 0 | 0 | 65 | 100 | 65 |
| Wild oat | 0 | 65 | 10 | 10 | 0 | 35 | 0 | 0 | 10 | 30 | 30 | 20 | 75 | 50 |

| | COMPOUND | | | | | | | | | |
|---|---|---|---|---|---|---|---|---|---|---|
| Rate 8 g/ha | 2 | 18 | 22 | 29 | 33 | 34 | 35 | 36 | 42 | 43 |

POSTEMERGENCE

| | | | | | | | | | | |
|---|---|---|---|---|---|---|---|---|---|---|
| Barley Igri | 45 | 25 | 20 | 45 | 35 | 55 | 40 | 40 | 25 | 30 |
| Barnyard 2 | 20 | 0 | 0 | 0 | 40 | 35 | 0 | 25 | 100 | 0 |
| Barnyardgrass | 60 | 25 | 0 | 30 | 50 | 50 | 35 | 30 | 65 | 40 |
| Bedstraw | 100 | 25 | 0 | 35 | 55 | 95 | 50 | 65 | 80 | 60 |
| Blackgrass | 45 | 0 | 0 | 40 | 30 | 65 | 40 | 30 | 65 | 55 |

TABLE C-continued

| | | | | | | | | | | |
|---|---|---|---|---|---|---|---|---|---|---|
| Chickweed | 75 | 20 | 50 | 65 | 75 | 90 | 65 | 75 | 95 | 65 |
| Cocklebur | 90 | 40 | 50 | 80 | 90 | 90 | 10 | 70 | 100 | 85 |
| Corn | 50 | 10 | 10 | 20 | 20 | 15 | 20 | 20 | 50 | 25 |
| Cotton | 100 | 100 | 90 | 90 | 100 | 100 | 100 | 95 | 100 | 100 |
| Crabgrass | 70 | 15 | 0 | 15 | 20 | 20 | 10 | 15 | 65 | 30 |
| Downy Brome | 40 | 0 | 0 | 10 | 35 | 70 | 50 | 40 | 30 | 20 |
| Duck salad | 0 | 0 | 0 | 0 | 0 | 0 | 0 | 0 | 0 | 0 |
| Giant foxtail | 80 | 30 | 20 | 35 | 35 | 30 | 25 | 30 | 35 | 25 |
| Italn. Rygrass | 50 | 0 | 0 | 30 | 65 | 60 | 40 | 70 | 70 | 20 |
| Johnsongrass | 75 | 55 | 15 | 30 | 50 | 30 | 30 | 60 | 35 | 70 |
| Lambsquarter | 100 | 40 | 0 | 100 | 85 | 100 | 90 | 95 | 85 | 65 |
| Morningglory | 100 | 80 | 70 | 90 | 95 | 85 | 90 | 85 | — | 80 |
| Rape | 100 | 65 | 0 | 65 | 70 | 65 | 75 | 90 | 45 | 70 |
| Redroot Pigweed | 100 | 85 | 80 | 90 | 100 | 100 | 70 | 100 | 100 | 100 |
| Rice | 70 | 0 | 0 | 25 | 35 | 40 | 10 | 35 | 25 | 0 |
| Soybean | 90 | 50 | 40 | 40 | 40 | 80 | 35 | 60 | 80 | 70 |
| Speedwell | 100 | 100 | 40 | 95 | 100 | 95 | 65 | 95 | 100 | 95 |
| Sugar beet | 100 | 50 | 20 | 100 | 95 | 100 | 70 | 90 | 100 | 80 |
| Umbrella sedge | 0 | 0 | 0 | 0 | 0 | 0 | 0 | 0 | 0 | 0 |
| Velvetleaf | 100 | 100 | 100 | 100 | 95 | 100 | 100 | 100 | 100 | 100 |
| Watergrass 2 | 10 | 0 | 25 | 0 | 25 | 10 | — | 40 | 10 | 0 |
| Wheat | 35 | 20 | 30 | 30 | 30 | 30 | 35 | 10 | 30 | 20 |
| Wild buckwheat | 100 | 0 | 30 | — | 100 | 100 | 65 | 90 | 100 | 90 |
| Wild oat | 40 | 10 | 0 | 55 | 40 | 65 | 45 | 60 | 45 | 30 |
| PREEMERGENCE | | | | | | | | | | |
| Barley Igri | 0 | 0 | 0 | 0 | 0 | 0 | 0 | 0 | 20 | 0 |
| Barnyardgrass | 80 | 0 | 0 | 0 | 0 | 0 | 0 | 0 | 30 | 15 |
| Bedstraw | 100 | 0 | 0 | 0 | 0 | 30 | 0 | 0 | 90 | 50 |
| Blackgrass | 45 | 0 | 0 | 0 | 0 | 0 | 0 | 0 | 40 | 40 |
| Chickweed | 25 | 0 | 0 | 0 | 0 | 0 | 0 | 0 | 70 | — |
| Cocklebur | 20 | 0 | 0 | 0 | 0 | 10 | 0 | 0 | 10 | 0 |
| Corn | 25 | 0 | 0 | 0 | 0 | 0 | 0 | 0 | 25 | 10 |
| Cotton | 30 | 0 | 0 | 0 | — | 30 | 0 | 0 | 55 | 0 |
| Crabgrass | 95 | 0 | 0 | 0 | 0 | 10 | 0 | 0 | 30 | 30 |
| Downy Brome | 10 | 0 | 0 | 0 | 0 | 0 | 0 | 10 | 10 | 10 |
| Giant foxtail | 90 | 0 | 0 | 10 | 0 | 30 | 0 | 0 | 85 | 70 |
| Italn. Rygrass | 55 | 0 | 0 | 0 | 0 | 0 | 10 | 40 | 50 | 30 |
| Johnsongrass | 85 | 0 | 0 | 0 | 0 | 0 | 0 | 0 | 30 | 10 |
| Lambsquarter | 100 | 0 | 0 | 100 | 45 | 100 | 90 | 90 | 90 | 90 |
| Morningglory | 50 | 0 | 10 | 0 | 10 | 30 | 0 | 10 | 65 | 20 |
| Rape | 45 | 0 | 0 | 0 | 0 | 0 | 0 | 0 | 60 | 0 |
| Redroot Pigweed | 100 | 0 | 50 | — | 45 | 70 | 0 | 20 | 100 | 60 |
| Soybean | 50 | 0 | 0 | 0 | 0 | 0 | 0 | 0 | 35 | 0 |
| Speedwell | 100 | 0 | 0 | 0 | 0 | 90 | 10 | 90 | 100 | 100 |
| Sugar beet | 100 | 0 | 0 | 0 | 0 | 20 | 0 | 0 | 70 | 55 |
| Velvetleaf | 100 | 0 | 0 | 0 | 20 | 25 | 0 | 0 | 70 | 10 |
| Wheat | 0 | 0 | 0 | 0 | 0 | 0 | 0 | 40 | 10 | 0 |
| Wild buckwheat | 55 | 0 | 0 | 0 | 0 | 0 | 0 | 0 | 70 | 10 |
| Wild oat | 25 | 10 | 0 | 0 | 0 | 0 | 30 | 0 | 35 | 20 |

| | COMPOUND | | | | COMPOUND | |
|---|---|---|---|---|---|---|
| Rate 4 g/ha | 2 | 42 | Rate 4 g/ha | | 2 | 42 |
| POSTEMERGENCE | | | PREEMERGENCE | | | |
| Barley Igri | 45 | 25 | Barley Igri | | 0 | 10 |
| Barnyard 2 | — | 100 | Barnyardgrass | | 20 | 15 |
| Barnyardgrass | 25 | 10 | Bedstraw | | 0 | 30 |
| Bedstraw | 80 | 0 | Blackgrass | | 10 | 20 |
| Blackgrass | 40 | 30 | Chickweed | | 0 | 10 |
| Chickweed | 60 | 75 | Cocklebur | | 0 | 0 |
| Cocklebur | 65 | 100 | Corn | | 0 | 0 |
| Corn | 25 | 20 | Cotton | | 0 | 0 |
| Cotton | 90 | 95 | Crabgrass | | 85 | 30 |
| Crabgrass | 30 | 30 | Downy Brome | | — | 10 |
| Downy Brome | 35 | 10 | Giant foxtail | | 85 | 85 |
| Duck salad | — | 0 | Italn. Rygrass | | 45 | 30 |
| Giant foxtail | 70 | 20 | Johnsongrass | | 60 | 10 |
| Italn. Rygrass | 35 | 30 | Lambsquarter | | 100 | 85 |
| Johnsongrass | 40 | 20 | Morningglory | | 50 | 30 |
| Lambsquarter | 100 | 65 | Rape | | 0 | 30 |
| Morningglory | 95 | 100 | Redroot Pigweed | | 100 | 80 |
| Rape | 100 | 30 | Soybean | | 0 | 30 |
| Redroot Pigweed | 100 | 100 | Speedwell | | — | 80 |
| Rice | — | 25 | Sugar beet | | 60 | 10 |
| Soybean | 80 | 60 | Velvetleaf | | 100 | 20 |
| Speedwell | 100 | 100 | Wheat | | 0 | 0 |

TABLE C-continued

| | | | | | |
|---|---|---|---|---|---|
| Sugar beet | 100 | 50 | Wild buckwheat | 0 | 60 |
| Umbrella sedge | — | 0 | Wild oat | 30 | 25 |
| Velvetleaf | 100 | 100 | | | |
| Watergrass 2 | — | 10 | | | |
| Wheat | 30 | 20 | | | |
| Wild buckwheat | 100 | 80 | | | |
| Wild oat | 40 | 25 | | | |

| Rate 2 g/ha | COMPOUND 2 | Rate 2 g/ha | COMPOUND 2 |
|---|---|---|---|
| POSTEMERGENCE | | PREEMERGENCE | |
| Barley Igri | 40 | Barley Igri | 0 |
| Barnyard 2 | — | Barnyardgrass | 0 |
| Barnyardgrass | 20 | Bedstraw | 0 |
| Bedstraw | 10 | Blackgrass | 10 |
| Blackgrass | 30 | Chickweed | 0 |
| Chickweed | 60 | Cocklebur | 0 |
| Cocklebur | 60 | Corn | 0 |
| Corn | 25 | Cotton | 0 |
| Cotton | 90 | Crabgrass | 65 |
| Crabgrass | — | Downy Brome | 0 |
| Downy Brome | 35 | Giant foxtail | 65 |
| Duck salad | — | Italn. Rygrass | 25 |
| Giant foxtail | 60 | Johnsongrass | 20 |
| Italn. Rygrass | 20 | Lambsquarter | 90 |
| Johnsongrass | 40 | Morningglory | 0 |
| Lambsquarter | 100 | Rape | 0 |
| Morningglory | 80 | Redroot Pigweed | 90 |
| Rape | 90 | Soybean | 0 |
| Redroot Pigweed | 100 | Speedwell | — |
| Rice | — | Sugar beet | 20 |
| Soybean | 35 | Velvetleaf | 90 |
| Speedwell | 100 | Wheat | 0 |
| Sugar beet | 100 | Wild buckwheat | 0 |
| Umbrella sedge | — | Wild oat | 20 |
| Velvetleaf | 100 | | |
| Watergrass 2 | — | | |
| Wheat | 30 | | |
| Wild buckwheat | 95 | | |
| Wild oat | 40 | | |

| Rate 1 g/ha | COMPOUND 2 | Rate 1 g/ha | COMPOUND 2 |
|---|---|---|---|
| POSTEMERGENCE | | PREEMERGENCE | |
| Barley Igri | 40 | Barley Igri | 0 |
| Barnyard 2 | — | Barnyardgrass | 0 |
| Barnyardgrass | 15 | Bedstraw | 0 |
| Bedstraw | 0 | Blackgrass | 10 |
| Blackgrass | 25 | Chickweed | 0 |
| Chickweed | 55 | Cocklebur | 0 |
| Cocklebur | 50 | Corn | 0 |
| Corn | 20 | Cotton | 0 |
| Cotton | 90 | Crabgrass | 30 |
| Crabgrass | 25 | Downy Brome | 0 |
| Downy Brome | 10 | Giant foxtail | 0 |
| Duck salad | — | Italn. Rygrass | 10 |
| Giant foxtail | 35 | Johnsongrass | 20 |
| Italn. Rygrass | 10 | Lambsquarter | 40 |
| Johnsongrass | 40 | Morningglory | 0 |
| Lambsquarter | 85 | Rape | 0 |
| Morningglory | 50 | Redroot Pigweed | 90 |
| Rape | 90 | Soybean | 0 |
| Redroot Pigweed | 90 | Speedwell | — |
| Rice | — | Sugar beet | 0 |
| Soybean | 35 | Velvetleaf | 50 |
| Speedwell | 100 | Wheat | 0 |
| Sugar beet | 80 | Wild buckwheat | 0 |
| Umbrella sedge | — | Wild oat | 10 |
| Velvetleaf | 100 | | |
| Watergrass 2 | — | | |
| Wheat | 10 | | |
| Wild buckwheat | 75 | | |
| Wild oat | 35 | | |

TEST D

Seeds, rhizomes, or plant parts of alfalfa (*Medicago sativa*), annual bluegrass (*Poa annua*), bermudagrass (*Cynodon dactylon*), broadleaf signalgrass (*Brachiaria platyphylla*), common purslane (*Portulaca oleracea*), common ragweed (*Ambrosia artemisiifolia*), dallisgrass (*Paspalum dilatatum*), field bindweed (*Convolvulus arvensis*), goosegrass (*Eleusine indica*), guineagrass (*Panicum maximum*), itchgrass (*Rottboellia cochinchinensis*), johnsongrass (*Sorghum halepense*), large crabgrass (*Digitaria sanguinalis*), peanut (*Arachis hypogaea*), pitted morningglory (*Ipomoea lacunosa*), purple nutsedge (*Cyperus rotundus*), sandbur (*Southern sandbur*), smooth crabgrass (*Digitaria ischaemum*) were planted into greenhouse pots containing greenhouse planting medium. Each pot contained only one plant species.

The test compound was formulated in a non-phytotoxic solvent mixture which includes a surfactant and applied preemergence and/or postemergence to the plants. Preemergence applications were made within one day of planting the seeds or plant parts. Postemergence applications were applied when the plants were in the two to four leaf stage (three to twenty cm). Untreated control plants and treated plants were placed in the greenhouse and visually evaluated for injury at 14 to 28 days after herbicide application. Plant response ratings, summarized in Table D, are based on a 0 to 100 scale where 0 is no injury and 100 is complete control. A dash (-) response indicates no test result.

TABLE D

| | COMPOUND | | | COMPOUND | |
|---|---|---|---|---|---|
| Rate 0250 g/ha | 2 | 41 | Rate 0250 g/ha | 2 | 41 |
| POSTEMERGENCE | | | PREEMERGENCE | | |
| Alfalfa Var. | 65 | 20 | Alfalfa Var. | 95 | 50 |
| Ann Bluegrass | 60 | 0 | Ann Bluegrass | 90 | 35 |
| Bermudagrass | 20 | 30 | Bermudagrass | 100 | 98 |
| Brdlf Sgnlgrass | 80 | 95 | Brdlf Sgnlgrass | 100 | 98 |
| Cmn Purslane | 100 | 95 | Cmn Purslane | 100 | 100 |
| Cmn Ragweed | 100 | 100 | Cmn Ragweed | 100 | 100 |
| Dallisgrass | 75 | 20 | Dallisgrass | 100 | 100 |
| Field Bindweed | 98 | 100 | Field Bindweed | 100 | 100 |
| Goosegrass | 75 | 50 | Goosegrass | 100 | 100 |
| Guineagrass | 65 | 0 | Guineagrass | 100 | 100 |
| Itchgrass | 50 | 30 | Itchgrass | 95 | 60 |
| Johnson grass | 80 | 20 | Johnson grass | 100 | 35 |
| Large Crabgrass | 70 | 55 | Large Crabgrass | 100 | 98 |
| Peanuts | 65 | 40 | Peanuts | 20 | 50 |
| Pit Morningglory | 80 | 40 | Pit Morningglory | 85 | 80 |
| Purple Nutsedge | — | 80 | Purple Nutsedge | 50 | 35 |
| Sandbur | 75 | 50 | Sandbur | 95 | 65 |
| Smooth Crabgras | 60 | 30 | Smooth Crabgras | 98 | 98 |

| | COMPOUND | | COMPOUND |
|---|---|---|---|
| Rate 0125 g/ha | 41 | Rate 0125 g/ha | 41 |
| POSTEMERGENCE | | PREEMERGENCE | |
| Alfalfa Var. | 30 | Alfalfa Var. | 60 |
| Ann Bluegrass | 0 | Ann Bluegrass | 0 |
| Bermudagrass | 0 | Bermudagrass | 50 |
| Brdlf Sgnlgrass | 30 | Brdlf Sgnlgrass | 50 |
| Cmn Purslane | 70 | Cmn Purslane | 100 |
| Cmn Ragweed | 100 | Cmn Ragweed | 50 |
| Dallisgrass | 20 | Dallisgrass | 20 |
| Field Bindweed | 100 | Field Bindweed | 50 |
| Goosegrass | 20 | Goosegrass | 100 |
| Guineagrass | 20 | Guineagrass | 40 |
| Itchgrass | 40 | Itchgrass | 40 |

TABLE D-continued

| Johnson grass | 0 | Johnson grass | 40 |
|---|---|---|---|
| Large Crabgrass | 0 | Large Crabgrass | 50 |
| Peanuts | 10 | Peanuts | 50 |
| Pit Morningglory | 10 | Pit Morningglory | 65 |
| Purple Nutsedge | — | Purple Nutsedge | 25 |
| Sandbur | 0 | Sandbur | 30 |
| Smooth Crabgras | 0 | Smooth Crabgras | 30 |

TEST E

Seeds of barnyardgrass (*Echinochloa crus-galli*), bindweed (*Concolculus arvensis*), black nightshade (*Solanum ptycanthum dunal*), cassia (*Cassia obtusifolia*), cocklebur (*Xanthium pensylvanicum*), corn (*Zea mays*), cotton (*Gossypium hirsutam*), crabgrass (*Digitaria* spp.), fall panicum (*Panicum dichotomiflorum*), giant foxtail (*Setaria faberii*), green foxtail (*Setaria viridis*), jimsonweed (*Datura stramonium*), johnsongrass (*Sorghum halepense*), lambsquarter (*Chenopodium album*), morningglory (*Ipomoea* spp.), pigweed (*Amaranthus retroflexus*), prickly sida (*Sida spinosa*), ragweed (*Ambrosia artemisiifolia*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Pancium miliaceum*), woolly cupgrass (*Eriochloa villosa*), yellow foxtail (*Setaria lutescens*) and purple nutsedge (*Cyperus rotundus*) tubers were planted into a matapeake sandy loam soil. These crops and weeds were grown in the greenhouse until the plants ranged in height from two to eighteen cm (one to four leaf stage), then treated postemergence with the test chemicals formulated in a non-phytotoxic solvent mixture which includes a surfactant. Pots receiving preemergence treatments were planted immediately prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table E, are reported on a 0 to 100 scale where 0 is no effect and 100 is complete control.

| Table E | COMPOUND | Table E | COMPOUND | |
|---|---|---|---|---|
| Rate 70 g/ha | 4 | Rate 35 g/ha | 4 | 42 |
| POST-EMERGENCE | | POST-EMERGENCE | | |
| Barnyardgrass | 55 | Barnyardgrass | 40 | 45 |
| Bindweed | 45 | Bindweed | 30 | 100 |
| Blk Nightshade | 45 | Blk Nightshade | 35 | 45 |
| Cassia | 30 | Cassia | 25 | 95 |
| Cocklebur | 60 | Cocklebur | 35 | 95 |
| Corn | 50 | Corn | 35 | 70 |
| Cotton | 100 | Cotton | 100 | 100 |
| Crabgrass | 40 | Crabgrass | 35 | 25 |
| fall Panicum | 45 | Fall Panicum | 35 | 35 |
| Giant Foxtail | 40 | Giant Foxtail | 25 | 35 |
| Green Foxtail | 35 | Green Foxtail | 25 | 35 |
| Jimsonweed | 85 | Jimsonweed | 60 | 95 |
| Johnson Grass | 40 | Johnson Grass | 35 | 40 |
| Lambsquarter | 40 | Lambsquarter | 35 | 70 |
| Morningglory | 100 | Morningglory | 95 | 100 |
| Nutsedge | 20 | Nutsedge | 10 | 25 |

| Table E | COMPOUND | Table E | COMPOUND |
|---|---|---|---|
| Rate 17 g/ha | 4    42 | Rate 8 g/ha | 4    42 |
| POST-EMERGENCE | | POST-EMERGENCE | |
| Pigweed | 95 | Pigweed | 55    100 |
| Prickly Sida | 50 | Prickly Sida | 45    100 |
| Ragweed | 50 | Ragweed | 35    60 |
| Shattercane | 50 | Shattercane | 40    55 |
| Signalgrass | 30 | Signalgrass | 20    50 |
| Smartweed | 35 | Smartweed | 20    40 |
| Soybean | 85 | Soybean | 30    90 |
| Sunflower | 80 | Sunflower | 75    85 |
| Velvetleaf | 95 | Velvetleaf | 85    100 |
| Wild Proso | 45 | Wild Proso | 35    40 |
| Woolly cupgrass | 30 | Woolly cupgrass | 25    35 |
| Yellow Foxtail | 40 | Yellow Foxtail | 25    35 |

| Table E | COMPOUND | Table E | COMPOUND |
|---|---|---|---|
| Rate 17 g/ha | 4    42 | Rate 8 g/ha | 4    42 |
| POST-EMERGENCE | | POST-EMERGENCE | |
| Barnyardgrass | 25    30 | Barnyardgrass | 25    25 |
| Bindweed | 25    100 | Bindweed | 20    75 |
| Blk Nightshade | 20    35 | Blk Nightshade | 15    25 |
| Cassia | 15    55 | Cassia | 10    50 |
| Cocklebur | 20    65 | Cocklebur | 15    60 |
| Corn | 30    40 | Corn | 25    35 |
| Cotton | 85    100 | Cotton | 80    100 |
| Crabgrass | 25    20 | Crabgrass | 20    15 |
| Fall Panicum | 25    25 | Fall Panicum | 20    25 |
| Giant Foxtail | 25    30 | Giant Foxtail | 15    30 |
| Green Foxtail | 20    35 | Green Foxtail | 15    30 |
| Jimsonweed | 25    75 | Jimsonweed | 15    55 |
| Johnson Grass | 30    30 | Johnson Grass | 25    25 |
| Lambsquarter | 25    65 | Lambsquarter | 25    50 |
| Morningglory | 25    100 | Morningglory | 15    95 |
| Nutsedge | 0    20 | Nutsedge | 0    15 |
| Pigweed | 35    100 | Pigweed | 25    100 |
| Prickly Sida | 20    100 | Prickly Sida | 15    80 |
| Ragweed | 25    35 | Ragweed | 20    30 |
| Shattercane | 35    45 | Shattercane | 25    35 |
| Signalgrass | 15    45 | Signalgrass | 15    35 |
| Smartweed | 15    30 | Smartweed | 15    25 |
| Soybean | 30    75 | Soybean | 25    60 |
| Sunflower | 50    80 | Sunflower | 45    80 |
| Velvetleaf | 30    100 | Velvetleaf | 20    85 |
| Wild Proso | 25    35 | Wild Proso | 20    35 |
| Woolly cupgrass | 20    25 | Woolly cupgrass | 15    20 |
| Yellow Foxtail | 20    30 | Yellow Foxtail | 15    25 |

| Table E | COMPOUND | Table E | COMPOUND |
|---|---|---|---|
| Rate 4 g/ha | 4    42 | Rate 2 g/ha | 42 |
| POST-EMERGENCE | | POST-EMERGENCE | |
| Barnyardgrass | 15    25 | Barnyardgrass | 15 |
| Bindweed | 15    65 | Bindweed | 15 |
| Blk Nightshade | 10    20 | Blk Nightshade | 15 |
| Cassia | 0    45 | Cassia | 30 |
| Cocklebur | 10    55 | Cocklebur | 25 |
| Corn | 25    30 | Corn | 25 |
| Cotton | 75    100 | Cotton | 100 |
| Crabgrass | 20    10 | Crabgrass | 0 |
| Fall Panicum | 10    15 | Fall Panicum | 10 |
| Giant Foxtail | 10    25 | Giant Foxtail | 20 |
| Green Foxtail | 10    25 | Green Foxtail | 20 |
| Jimsonweed | 10    50 | Jimsonweed | 45 |
| Johnson Grass | 20    20 | Johnson Grass | 15 |
| Lambsquarter | 20    45 | Lambsquarter | 35 |
| Morningglory | 10    95 | Morningglory | 35 |
| Nutsedge | 0    10 | Nutsedge | 0 |
| Pigweed | 15    100 | Pigweed | 100 |
| Prickly Sida | 10    75 | Prickly Sida | 20 |
| Ragweed | 15    30 | Ragweed | 25 |
| Shattercane | 20    35 | Shattercane | 25 |
| Signalgrass | 10    30 | Signalgrass | 25 |
| Smartweed | 10    20 | Smartweed | 10 |
| Soybean | 20    50 | Soybean | 45 |
| Sunflower | 30    75 | Sunflower | 70 |
| Velvetleaf | 10    80 | Velvetleaf | 40 |
| Wild Proso | 20    25 | Wild Proso | 20 |
| Woolly cupgrass | 10    15 | Woolly cupgrass | 10 |
| Yellow Foxtail | 15    25 | Yellow Foxtail | 25 |

TEST F

Compounds evaluated in this test were formulated in a non-phytotoxic solvent mixture which includes a surfactant and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), galium (*Galium aparine*), green foxtail (*Setaria viridis*), kochia (*Kochia scoparia*), lambsquarters (*Chenopodium album*), speedwell (*Veronica persica*), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), windgrass (*Apera spica-venti*), winter wheat (*Triticum aestivum* cv. 'Talent'), wild buckwheat (*Polygonum convolvulus*), wild mustard (*Sinapis arvensis*) and wild oat (*Avena fatua*).

Blackgrass, galium and wild oat were treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table F, are based upon a 0 to 100 scale where 0 is no effect and 100 is complete control. A dash response (-) means no test result.

| Table F | COMPOUND | Table F | COMPOUND |
|---|---|---|---|
| Rate 125 g/ha | 23 | Rate 125 g/ha | 23 |
| POST-EMERGENCE | | PRE-EMERGENCE | |
| Blackgrass (2) | 80 | Blackgrass (2) | 50 |
| Chickweed | 100 | Chickweed | 100 |
| Downy brome | 40 | Downy brome | 50 |
| Galium (2) | 100 | Galium (2) | 100 |
| Green foxtail | — | Green foxtail | 100 |
| Kochia | 100 | Kochia | 80 |
| Lambsquarters | 100 | Lambsquarters | 100 |
| Ryegrass | 85 | Ryegrass | 75 |
| Speedwell | 100 | Speedwell | 100 |
| Wheat (Spring) | 50 | Wheat (Spring) | 70 |
| Wheat (Winter) | 35 | Wheat (Winter) | 35 |
| Wild buckwheat | 100 | Wild buckwheat | 100 |
| Wild mustard | 100 | Wild mustard | 100 |
| Wild oat (2) | 55 | Wild oat (2) | 70 |
| Windgrass | 100 | Windgrass | 100 |
| Winter Barley | 20 | Winter Barley | 20 |

-continued

| Table F Rate 62 g/ha | COMPOUND 2 | Table F Rate 62 g/ha | COMPOUND 23 |
|---|---|---|---|
| POST-EMERGENCE | | PRE-EMERGENCE | |
| Blackgrass (2) | 5 | Blackgrass (2) | 50 |
| Chickweed | 100 | Chickweed | 70 |
| Downy brome | 5 | Downy brome | 40 |
| Galium (2) | 100 | Galium (2) | 100 |
| Green foxtail | 100 | Green foxtail | 100 |
| Kochia | 100 | Kochia | 55 |
| Lambsquarters | 100 | Lambsquarters | 100 |
| Ryegrass | 20 | Ryegrass | 60 |
| Speedwell | 100 | Speedwell | 100 |
| Wheat (Spring) | 50 | Wheat (Spring) | 65 |
| Wheat (Winter) | 20 | Wheat (Winter) | 35 |
| Wild buckwheat | 100 | Wild buckwheat | 70 |
| Wild mustard | 100 | Wild mustard | 100 |
| Wild oat (2) | 30 | Wild oat (2) | 50 |
| Windgrass | 60 | Windgrass | 100 |
| Winter Barley | 20 | Winter Barley | 10 |

| Table F Rate 31 g/ha | COMPOUND 2 | Table F Rate 31 g/ha | COMPOUND 23 |
|---|---|---|---|
| POST-EMERGENCE | | PRE-EMERGENCE | |
| Blackgrass (2) | 5 | Blackgrass (2) | 30 |
| Chickweed | 100 | Chickweed | 40 |
| Downy brome | 0 | Downy brome | 10 |
| Galium (2) | 100 | Galium (2) | 100 |
| Green foxtail | 70 | Green foxtail | 100 |
| Kochia | 100 | Kochia | 50 |
| Lambsquarters | 100 | Lambsquarters | 100 |
| Ryegrass | 5 | Ryegrass | 45 |
| Speedwell | 100 | Speedwell | 100 |
| Wheat (Spring) | 20 | Wheat (Spring) | 10 |
| Wheat (Winter) | 15 | Wheat (Winter) | 0 |
| Wild buckwheat | 100 | Wild buckwheat | 85 |
| Wild mustard | 100 | Wild mustard | 100 |
| Wild oat (2) | 20 | Wild oat (2) | 35 |
| Windgrass | 20 | Windgrass | 100 |
| Winter Barley | 10 | Winter Barley | 0 |

| Table F Rate 16 g/ha | COMPOUND 2 | Table F Rate 16 g/ha | COMPOUND 23 |
|---|---|---|---|
| POST-EMERGENCE | | PRE-EMERGENCE | |
| Blackgrass (2) | 5 | Blackgrass (2) | 0 |
| Chickweed | 100 | Chickweed | 40 |
| Downy brome | 0 | Downy brome | 0 |
| Galium (2) | 60 | Galium (2) | 35 |
| Green foxtail | 70 | Green foxtail | 95 |
| Kochia | 100 | Kochia | 50 |
| Lambsquarters | 40 | Lambsquarters | 100 |
| Ryegrass | 5 | Ryegrass | 10 |
| Speedwell | 100 | Speedwell | 100 |
| Wheat (Spring) | 20 | Wheat (Spring) | 15 |
| Wheat (Winter) | 15 | Wheat (Winter) | 0 |
| Wild buckwheat | 60 | Wild buckwheat | 100 |
| Wild mustard | 100 | Wild mustard | 100 |
| Wild oat (2) | 15 | Wild oat (2) | 10 |
| Windgrass | 5 | Windgrass | 95 |
| Winter Barley | 10 | Winter Barley | 0 |

| Table F Rate 8 g/ha | COMPOUND 2 | Table F Rate 4 g/ha | COMPOUND 2 |
|---|---|---|---|
| POST-EMERGENCE | | PRE-EMERGENCE | |
| Blackgrass (2) | 5 | Blackgrass (2) | 5 |
| Chickweed | 80 | Chickweed | 60 |
| Downy brome | 0 | Downy brome | 0 |
| Galium (2) | 50 | Galium (2) | — |
| Green foxtail | 30 | Green foxtail | 5 |
| Kochia | 30 | Kochia | 5 |
| Lambsquarter | — | Lambsquarters | 0 |
| Ryegrass | 5 | Ryegrass | 5 |
| Speedwell | 100 | Speedwell | 100 |
| Wheat (Spring) | 15 | Wheat (Spring) | 10 |
| Wheat (Winter) | 15 | Wheat (Winter) | 10 |
| Wild buckwheat | 10 | Wild buckwheat | — |
| Wild mustard | 100 | Wild mustard | 80 |
| Wild oat (2) | 10 | Wild oat (2) | 10 |
| Windgrass | 5 | Windgrass | 5 |
| Winter Barley | 10 | Winter Barley | 10 |

What is claimed is:

1. A compound Formulae I

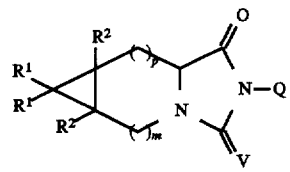

wherein

Q is

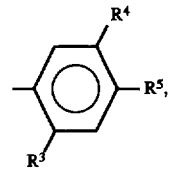   Q-1

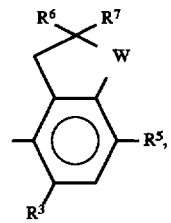   Q-2

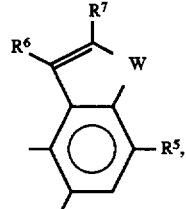   Q-3

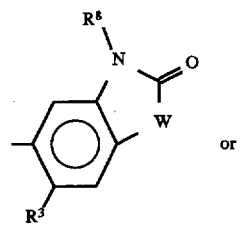   Q-4 or

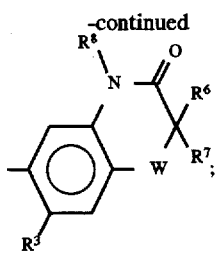

Q-5

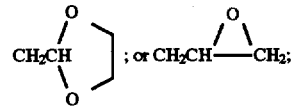

$R^1$ is independently hydrogen; halogen or $C_1$–$C_3$ alkyl;

$R^2$ is independently hydrogen; fluorine; chlorine; or bromine;

V is O or S;

m is 1 or 2;

p is 0 or 1 provided that when m is 2, then p is 0;

W is O or S;

$R^3$ is halogen;

$R^4$ is H; $C_1$–$C_8$ alkyl; $C_1$–$C_8$ haloalkyl; halogen; OH; $OR^9$; SH; $S(O)_nR^9$; $COR^9$; $CO_2R^9$; $C(O)SR^9$; $C(O)NR^{11}R^{12}$; CHO; $CR^{11}$=$NOR^{18}$; CH=$CR^{19}CO_2R^9$; $CH_2CHR^{19}CO_2R^9$; $CO_2N$=$CR^{13}R^{14}$; $NO_2$; CN; $NHSO_2R^{15}$; $NHSO_2NHR^{15}$; $NR^9R^{20}$; $NH_2$ or phenyl optionally substituted with $R^{21}$;

n is 0, 1 or 2;

$R^5$ is $C_1$–$C_2$ alkyl; $C_1$–$C_2$ haloalkyl; $OCH_3$; $SCH_3$; $OCHF_2$; halogen; CN or $NO_2$;

$R^6$ is H; $C_1$–$C_3$ alkyl or halogen;

$R^7$ is H; $C_1$–$C_3$ alkyl; halogen; $C_1$–$C_3$ haloalkyl; cyclopropyl; vinyl; $C_2$ alkynyl; CN; $C(O)R^{20}$; $CO_2R^{20}$; $C(O)NR^{20}R^{22}$; $CR^{16}R^{17}CN$; $CR^{16}R^{17}C(O)R^{20}$; $CR^{16}R^{17}CO_2R^{20}$; $CR^{16}R^{17}C(O)NR^{20}R^{22}$; $CHR^{16}OH$; $CHR^{16}OC(O)R^{20}$ or $OCHR^{16}OC(O)NR^{20}R^{22}$; or when Q is Q-2, $R^6$ and $R^7$ can be taken together with the carbon to which they are attached to form C=O;

$R^8$ is H; $C_1$–$C_6$ alkyl; $C_1$–$C_6$ haloalkyl; $C_2$–$C_6$ alkoxyalkyl; $C_3$–$C_6$ alkenyl; $C_3$–$C_6$ alkynyl; $C_4$–$C_7$ cycloalkylalkyl;

$R^9$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ alkoxyalkoxyalkyl; $C_4$–$C_8$ cycloalkylalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenyloxyalkyl; $C_4$–$C_8$ haloalkynyloxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with halogen, $C_1$–$C_3$ alkyl or $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkylcarbonyl; benzyl optionally substituted with halogen, $C_1$–$C_3$ alkyl or $C_1$–$C_3$ haloalkyl; $CHR^{16}COR^{10}$; $CHR^{16}P(O)(OR^{10})_2$; $CHR^{16}P(S)(OR^{10})_2$; $P(O)(OR^{10})_2$; $P(S)(OR^{10})_2$; $CHR^{16}C(O)NR^{11}R^{12}$; $CHR^{16}C(O)NH_2$; $CHR^{16}CO_2R^{10}$; $CO_2R^{10}$; $SO_2R^{10}$; phenyl optionally substituted with $R^{21}$;

$CH_2CH\begin{array}{c}O\\|\\O\end{array}$ ; or $CH_2CH$—$CH_2$ ;

$R^{10}$ is $C_1$–$C_6$ alkyl; $C_1$–$C_6$ haloalkyl; $C_3$–$C_6$ alkenyl or $C_3$–$C_6$ alkynyl;

$R^{11}$ and $R^{13}$ are independently H or $C_1$–$C_4$ alkyl;

$R^{12}$ and $R^{14}$ are independently $C_1$–$C_4$ alkyl or phenyl optionally substituted with halogen, $C_1$–$C_3$ alkyl or $C_1$–$C_3$ haloalkyl; or $R^{11}$ and $R^{12}$ are taken together along with the nitrogen to which they are attached to form a piperidinyl, pyrrolidinyl or morpholinyl ring, each ring optionally substituted with $C_1$–$C_3$ alkyl, phenyl or benzyl; or $R^{13}$ and $R^{14}$ are taken together with the carbon to which they are attached to form $C_3$–$C_8$ cycloalkyl;

$R^{15}$ is $C_1$–$C_4$ alkyl or $C_1$–$C_4$ haloalkyl;

$R^{16}$ and $R^{17}$ are independently H or $C_1$–$C_5$ alkyl;

$R^{18}$ is H, $C_1$–$C_6$ alkyl, $C_3$–$C_6$ alkenyl or $C_3$–$C_6$ alkynyl;

$R^{19}$ and $R^{24}$ are independently H, $C_1$–$C_4$ alkyl or halogen; or $R^9$ and $R^{19}$ are taken together as $C_2$–$C_3$ alkylene;

$R^{20}$, $R^{21}$, and $R^{25}$ are independently H or $C_1$–$C_4$ alkyl;

$R^{22}$ is $C_1$–$C_2$ alkyl; $C_1$–$C_2$ haloalkyl; $OCH_3$; $SCH_3$; $OCHF_2$; or CN and their corresponding N-oxides and agriculturally-suitable salts.

2. A compound according to claim 1 wherein $R^1$ is hydrogen or halogen;

$R^2$ is hydrogen; chlorine; or fluorine;

$R^4$ is H; $C_1$–$C_8$ alkyl; $C_1$–$C_8$ haloalkyl; halogen; OH; $OR^9$; SH; $S(O)_nR^9$; $COR^9$; $CO_2R^9$; $C(O)SR^9$; $C(O)NR^{11}R^{12}$; CHO; CH=$CHCO_2R^9$; $CO_2N$=$CR^{13}R^{14}$; $NO_2$; CN; $NHSO_2R^{15}$; or $NHSO_2NHR^{15}$.

3. A compound according to claim 2 wherein $R^2$ is hydrogen or fluorine; and $R^9$ is $C_1$–$C_4$ alkyl; $C_3$–$C_4$ alkenyl; $C_3$–$C_4$ alkynyl; $C_2$–$C_4$ alkoxyalkyl; $C_1$–$C_4$ haloalkyl; $C_3$–$C_4$ haloalkenyl or $C_3$–$C_4$ haloalkynyl.

4. A compound according to claim 3 wherein

Q is Q-1 or Q-5;

$R^1$ and $R^2$ are each hydrogen; and $R^5$ is halogen; CN; or $NO_2$.

5. A compound according to claim 4 selected from the group:

(±)-2-[4-chloro-2-fluoro-5-(2-propynyloxy)phenyl]tetrahydrocyclopropa[3,4]-pyrrolo[1,2-c]imidazole-1,3(2H,3aH)-dione and (±)-2-[4-chloro-2-fluoro-5-[(1-methyl-2-propynyl)oxy]phenyl]tetrahydrocyclopropa[3,4]-pyrrolo[1,2-c]imidazole-1,3(2H,3aH)-dione.

6. An herbicidal composition comprising an herbicidally effective amount of a compound according to claim 1 and an agriculturally suitable carrier.

7. A method for controlling the growth of undesired vegetation comprising applying to the undesired vegetation or to the locus to be protected an herbicidally effective amount of a compound according to claim 1.

* * * * *